(12) United States Patent
Barr et al.

(10) Patent No.: US 7,247,704 B2
(45) Date of Patent: Jul. 24, 2007

(54) MULTIFUNCTIONAL PROTEASE INHIBITORS AND THEIR USE IN TREATMENT OF DISEASE

(75) Inventors: Philip J. Barr, Oakland, CA (US); Helen L. Gibson, Oakland, CA (US); Philip A. Pemberton, San Mateo, CA (US)

(73) Assignee: Arriva Pharmaceuticals, Inc., Alameda, CA (US)

( * ) Notice: Subject to any disclaimer, the term of this patent is extended or adjusted under 35 U.S.C. 154(b) by 0 days.

(21) Appl. No.: 10/025,514

(22) Filed: Dec. 18, 2001

(65) Prior Publication Data

US 2003/0073217 A1    Apr. 17, 2003

Related U.S. Application Data

(60) Provisional application No. 60/331,966, filed on Nov. 20, 2001, provisional application No. 60/256,699, filed on Dec. 18, 2000.

(51) Int. Cl.
*C07K 1/00* (2006.01)
*A61K 38/48* (2006.01)
*A61K 38/00* (2006.01)
*C07H 21/04* (2006.01)
*C12N 15/09* (2006.01)

(52) U.S. Cl. .................. 530/350; 424/94.64; 514/12; 536/23.4; 435/69.2; 435/226

(58) Field of Classification Search ................ 530/350; 536/23.4; 514/12; 435/69.2; 424/94.64
See application file for complete search history.

(56) References Cited

U.S. PATENT DOCUMENTS

| | | | |
|---|---|---|---|
| 4,522,811 A | 6/1985 | Eppstein et al. |
| 4,732,973 A | 3/1988 | Barr et al. |
| 4,746,648 A | 5/1988 | Wagnon et al. |
| 4,752,576 A | 6/1988 | Brake et al. |
| 4,760,130 A | 7/1988 | Thompson et al. |
| 4,845,076 A | 7/1989 | Heinzel et al. |
| 4,870,008 A | 9/1989 | Brake |
| 4,873,316 A | 10/1989 | Meade et al. |
| 5,008,242 A | 4/1991 | Lezdey et al. |
| 5,093,316 A | 3/1992 | Lezdey et al. |
| 5,217,951 A | 6/1993 | Lezdey et al. |
| 5,290,762 A | 3/1994 | Lezdey et al. |
| 5,328,470 A | 7/1994 | Nabel et al. |
| 5,464,822 A | 11/1995 | Christophers et al. |
| 5,595,885 A | 1/1997 | Stetler-Stevenson et al. |
| 5,633,227 A | 5/1997 | Muller et al. |
| 5,643,752 A | 7/1997 | Hawkins et al. |
| 5,780,440 A | 7/1998 | Lezdey et al. |
| 5,849,691 A | 12/1998 | Majer et al. |
| 5,851,983 A | 12/1998 | Sugiyama et al. |
| 5,871,956 A | 2/1999 | Bandyopadhyay et al. |
| 5,900,400 A | 5/1999 | Thompson et al. |
| 5,914,392 A | 6/1999 | Hawkins et al. |
| 5,985,309 A | 11/1999 | Edwards et al. |
| 6,017,880 A | 1/2000 | Eisenberg et al. |
| 6,068,994 A | 5/2000 | Barr |
| 6,124,257 A | 9/2000 | Lezdey et al. |
| 6,131,566 A | 10/2000 | Ashurst et al. |
| 6,136,295 A | 10/2000 | Edwards et al. |
| 6,143,277 A | 11/2000 | Ashurst et al. |
| 6,174,859 B1 | 1/2001 | Lezdey et al. |
| RE37,053 E | 2/2001 | Hanes et al. |
| 6,253,762 B1 | 7/2001 | Britto |
| 6,254,854 B1 | 7/2001 | Edwards et al. |
| 6,291,662 B1 | 9/2001 | Bandyopadhyay et al. |

FOREIGN PATENT DOCUMENTS

| | | |
|---|---|---|
| AU | B-13288/88 | 9/1988 |
| EP | 0 073 657 A1 | 3/1983 |
| EP | 0 073 657 B1 | 3/1983 |
| EP | 0 264 166 A1 | 4/1988 |
| EP | 0 283 932 | 9/1988 |
| EP | 0 404 750 B1 | 12/1990 |
| EP | 0 648 838 A1 | 4/1995 |
| JP | 63-267294 | 6/1991 |
| WO | WO 86/02100 A1 | 4/1986 |
| WO | WO 86/03519 A1 | 6/1986 |
| WO | WO 92/10575 * | 6/1992 |
| WO | WO 98/51788 | 11/1998 |

OTHER PUBLICATIONS

Urwin P. E. et al., Enhanced transgenic plant resistance to nemathodes by dual proteinase inhibitor constructs, Planta, 1998, 204, 472-479.*
Carrell R. W. et al., Alpha1-Antitrypsin Deficiency - A Model for Conformational Diseases, N. Engl. J. Med., 2002, 346, 45-53.*
Crystal, R.G. et al. (1989). "The Alpha$_1$-Antitrypsin Gene and Its Mutations. Clinical Consequences and Strategies for Therapy," *Chest* 95(1):196-208.
Jeppsson, J.O. and Laurell, C.B. (1988). "The Amino Acid Substitutions of Human α$_1$Antitrypsin M$_3$, X and Z," *FEBS Lett.* 231(2):327-330.

(Continued)

*Primary Examiner*—Rebecca E. Prouty
*Assistant Examiner*—Malgorzata A. Walicka
(74) *Attorney, Agent, or Firm*—Heller Ehrman LLP

(57) ABSTRACT

Fusion proteins of protease inhibitors are provided, in particular fusion proteins of alpha 1-antitrypsin (AAT) and a second protease inhibitor, such as secretory leukocyte protease inhibitor (SLPI) or tissue inhibitor of metalloproteases (TIMP). Polynucleotides encoding the fusion proteins, vectors comprising such polynucleotides, and host cells containing such vectors are also provided. Methods of making the fusion proteins of the invention are also provide, as well as methods of using the fusion proteins, for example to inhibit protease activity in a biological sample or in the treatment of an individual suffering from, or at risk for, a disease or disorder involving unwanted protease activity.

26 Claims, 6 Drawing Sheets

OTHER PUBLICATIONS

Kwon, K.S. et al. (1994). "Single Amino Acid Substitutions of $\alpha_1$-Antitrypsin That Confer Enhancement in Thermal Stability," *J. Biol. Chem.* 269(13):9627-9631.

Luisetti, M. et al. (1990). "Alpha 1-Antitrypsin Variants Produced by Recombinant DNA: Differences in Elastase Inhibitory Activity and Resistance to Oxidant Agents," *Int. J. Tissue React.* 12(6):363-368.

Patterson, S.D. (1991). "Mammalian $\alpha_1$-Antitrypsins: Comparative Biochemistry and Genetics of the Major Plasma Serpin," *Comp. Biochem. Physiol.* 100B(3):439-454.

Agarwal, N. S. and Rich, D. H. (1986). "Inhibition of Cathepsin D by Substrate Analogues Containing Statine and by Analogues of Pepstatin," *J. Med. Chem.* 29:2519-2524.

Ausubel, F. M. et al. (2001). *Current Protocols in Molecular Biology*, John Wiley & Sons, Inc. 11 pages total (Table of Contents for vols. 1-4 only).

Aviles, F. X. (1993). *Innovations in Proteases and Their Inhibitors*, W. DeGruyter, Berlin, N.Y. total pages 5. (Table of Contents).

Baldwin, E. T. et al. (Jul. 1993). "Crystal Structures of Native and Inhibited Forms of Human Cathepsin D: Implications for Lysosomal Targeting and Drug Design," *Proc. Natl. Acad. Sci.* 90:6796-6800.

Banerji, J. et al. (Jul. 1983). "A Lymphocyte-Specific Cellular Enhancer is Located Downstream of the Joining Region in Immunoglobulin Heavy Chain Genes," *Cell* 33:729-740.

Barnes, P. J. (Feb. 2000). "Mechanisms in COPD: Differences From Asthma," *Chest* 117(2):10S-14S.

Barnes, P. J. (Jul. 2000). "Chronic Obstructive Pulmonary Disease," *Medical Progress* 343(4)269-280.

Barrett, A. J. et al. (1986). "Cysteine Proteinase Inhibitors of the Cystatin Superfamily," Chapter 18 *In Proteinase Inhibitors*. A. J. Barrett and G. Salvesen eds., Elsevier Science Publishers, pp. 515-568.

Beaucage, S. L. and Caruthers, M. H. (1981). "Deoxynucleoside Phosphoramidites-A New Class of Key Intermediates for Deoxypolynucleotide Synthesis," *Tetrahedron Letters* 22(20):1859-1862.

Bingle, L. and Tetley, T.D. (1996). "Secretory Leukoprotease Inhibitor: Partnering $\alpha_1$-Proteinase Inhibitor to Combat Pulmonary Inflammation," *Science Matters* 51:1273-1274.

Bode, W. and Huber, R. (1992). "Natural Protein Proteinase Inhibitors and Their Interaction with Proteinases," *Eur. J. Biochem.* 204:433-451.

Bode, W. and Huber, R. (1994). "Proteinase-Protein Inhibitor Interactions," *Fibrinolysis* 8 (Suppl. 1):161-171.

Bode, W. and Huber, R. (2000). "Structural Basis of The Endoproteinase-Protein Inhibitor Interaction," *Biochimica et Biophysica Acta* 1477:241-252.

Boone, T. C. et al. (Apr. 1990). "cDNA Cloning and Expression of a Metalloproteinase Inhibitor Related to Tissue Inhibitor of Metalloproteinases," *Proc. Natl. Acad. Sci.* 87:2800-2804.

Byrne, G. W. and Ruddle, F. H. (Jul. 1989). "Multiplex Gene Regulation: A Two-Tiered Approach to Transgene Regulation in Transgenic Mice," *Proc. Natl. Acad. Sci.* 86:5473-5477.

Calame, K. and Eaton, S. (1988). "Transcriptional Controlling Elements in the Immunoglobulin and T Cell Receptor Loci," *Adv. in Immunol.* 43:235-275.

Camper, S. A. and Tilghman, S. M. (1989). "Postnatal Repression of the $\alpha$-Fetoprotein Gene is Enhancer Independent," *Genes & Dev.* 3:537-546.

Carrell, R.W. et al. (Jul. 1982). "Structure and Variation of Human $\alpha_1$-Antitrypsin," *Nature* 298:329-334.

Cawston, T. E. (1995). "Proteinases and Inhibitors," *British Medical Bulletin* 51(2):385-401.

Chen, S. H et al. (Apr. 1994). "Gene Therapy for Brain Tumors: Regression of Experimental Gliomas by Adenovirus-Mediated Gene Transfer *In Vivo*," *Proc. Natl. Acad. Sci.* 91:3054-3057.

Coligan, J. E. et al. (1991). *Current Protocols in Immumology*, John Wiley & Sons, Inc. 10 pages total. (Table of Contents of vols. 1-3 only).

Collier, I. E. et al. (May 1988). "H-ras Oncogene-transformed Human Bronchial Epithelial Cells (TBE-1) Secrete a Single Metalloprotease Capable of Degrading Basement Membrane Collagen," *The J. of Biol. Chem.* 263(14):6579-6587.

Docherty, A. J. P. et al. (Nov. 1985). "Sequence of Human Tissue Inhibitor of Metalloproteinases and its Identity to Erythroid-Potentiating Activity," *Nature* 318:66-69.

Eckman, E.A. et al. (Aug. 1999). "*In Vitro* Transport of Active $\alpha_1$-Antitrypsin to the Apical Surface of Epithelia by Targeting the Polymeric Immunoglobulin Receptor," *Am. J. Respir. Cell Mol. Biol.* 21:246-252.

Edlund, T. et al. (Nov. 1985). "Cell-Specific Expression of the Rat Insulin Gene: Evidence for Role of Two Distinct 5' Flanking Elements," *Science* 230:912-916.

Edwards, D.A. et al. (Jun. 1997). "Large Porous Particles for Pulmonary Drug Delivery," *Science* 276:1868-1871.

Ferkol, T. et al. (Mar. 2000). "Transport of Bifunctional Proteins Across Respiratory Epithelial Cells Via the Polymeric Immunoglobulin Receptor," *Am. J. Respir. Crit. Care Med.* 161(3):944-951.

Fiers, W. et al. (May 1978). "Complete Nucleotide Sequence of SV40 DNA," *Nature* 273:113-120.

Francis, S. E. et al. (1994). "Molecular Characterization and Inhibition of a *Plasmodium falciparum* Aspartic Hemoglobinase," *The EMBO J.* 13(2):306-317.

Freshney, R. I., ed. (1987). *Animal Cell Culture: A Practical Approach*. IRL Press at Oxford University Press. pp. ix-xiv. (Table of Contents).

Gait, M. J. ed., (1984). *Oligonucleotide Synthesis: A Practical Approach*. IRL Press at Oxford University Press. pp. vii-xii., (Table of Contents).

Gasson, J. C. et al. (Jun. 1985). "Molecular Characterization and Expression of the Gene Encoding Human Erythroid-Potentiating Activity," *Nature* 315:768-771.

Goeddel, D. V. (1990). "Gene Expression Technology," *In Methods in Enzymology*, Academic Press, Inc. San Diego 185:v-ix. (Table of Contents).

Gottesman, S. (1990). "Minimizing Proteolysis in *Escherichia Coli*: Genetic Solutions," *Methods in Enzymology*, J. N. Abelson and M. I. Simon, eds., Academic Press, Inc. 185:118-129.

Guyene,. T. T. et al. (Dec. 1976). "Inhibition of Human Plasma Renin Activity by Pepstatin," *The J. of Clin. Endocrinol. and Metab.* 43(6):1301-1306.

Heinzel, R. et al. (1986). "Molecular Cloning and Expression of cDNA for Human Antileukoprotease from Cervix Uterus," *Eur. J. Biochem.* 160:61-67.

Hercz, A. (Apr. 1985). "Proteolytic Cleavages In $\alpha_1$-Antitrypsin and Microheterogeneity," *Biochem. and Biophys. Res. Comm.* 128(1):199-203.

Huang, W. et al. (1996). "Folding and Characterization of the Amino-Terminal Domain of Human Tissue Inhibitor of Metalloproteinases-1 (TIMP-1) Expressed at High Yield in *E. coli*," *FEBS Lett.* 384:155-161.

Huff, J. R. (Aug. 1991). "HIV Protease: A Novel Chemotherapeutic Target for AIDS," *J. of Med. Chem.* 34(8):2305-2314.

Jupp, R. A. (Jul. 1990). "The Selectivity of Statine-Based Inhibitors Against Various Human Aspartic Proteinases," *Biochem. J.* 265:871-878.

Lin, T. Y. and Williams, H. R. (Dec. 1979). "Inhibition of Cathepsin D by Synthetic Oligopeptides," *J. Biol. Chem.* 254(23):11875-11883.

Kessel, M. and Gruss, P. (Jul. 1990). "Murine Development Control Genes," *Science* 249:374-379.

Kubo, T. et al. (Dec. 1988). "Location of a Region of the Muscarinic Acetylcholine Receptor Involved in Selective Effector Coupling," *FEBS Lett.* 241(1,2):119-125.

Kurachi, K. et al. (Nov. 1981). "Cloning and Sequence of cDNA Coding for $\alpha_1$-Antitrypsin," *Proc. Natl. Acad. Sci.* 78(11):6826-6830.

Kurjan, J. and Herskowitz, I. (Oct. 1982). "Structure of a Yeast Pheromone Gene (MF$\alpha$): A Putative $\alpha$-Factor Precursor Contains Four Tandem Copies of Mature $\alpha$-Factor," *Cell* 30:933-943.

Matteucci, M. D. and Caruthers, M. H. (1981). "Synthesis of Deoxyoligonucleotides on a Polymer Support," *J. Am. Chem. Soc.* 103(11):3185-3191.

McElvaney, N. G. et al. (Oct. 1992). "Modulation of Airway Inflammation in Cystic Fibrosis: In Vivo Suppression of Interleukin-8 Levels on the Respiratory Epithelial Surface by Aerosolization of Recombinant Secretory Leukoprotease Inhibitor," *The J. of Clin. Inves.* 90:1296-1301.

Merrifield, R. B. (Jul. 1963). "Solid Phase Peptide Synthesis. I. The Synthesis of a Tetrapeptide," *J. Amer. Chem. Soc.* 85:2149-2154.

Metzger, D. et al. (Jul. 1988). "The Human Oestrogen Receptor Functions in Yeast," *Nature* 334:31-36.

Miller, J. H. and Calos, M. P., eds. (1987). "Gene Transfer Vectors for Mammalian Cells," *In Current Communications in Molecular Biology*, Cold Spring Harbor Laboratory. pp. vi-ix. (Table of Contents).

Morishima, H. et al. (May 1970). "The Structure of Pepstatin," *The J. of Antibiot.* 23(5):263-265.

Mullis, K. B. et al. (1994). *The Polymerase Chain Reaction.* Birkhäuser, Boston, pp. xv-xvii. (Table of Contents).

Murphy, G. et al., eds. (Aug. 1991). "The N-Terminal Domain of Tissue Inhibitor of Metalloproteinases Retains Metalloproteinase Inhibitory Activity," *Biochemistry* 30(33):8097-8102.

Murray, E. E. et al. (1989). "Codon Usage in Plant Genes," *Nucleic Acids Res.* 17(2):477-498.

Nakajima, K. and Powers, J. C. (May 1979). "Mapping the Extended Substrate Binding Site of Cathepsin G and Human Leukocyte Elastase: Studies with Peptide Substrates Related to the $\alpha_1$-Protease Inhibitor Reactive Site," *The J. of Biol. Chem.* 254(10):4027-4032.

Otlewski, J. et al. (1999). "Protein Inhibitors of Serine Proteinases," *Acta Biochimica Polonica* 46(3):531-565.

Pearson, W. R. and Lipman, D. J. (Apr. 1988). "Improved Tools for Biological Sequence Comparison," *Proc. Natl. Acad. Sci.* 85:2444-2448.

Pennington, M. W. et al. (1990). *Twenty-First European Peptide Symposium.* Gimet E. and Andrew D, eds. Escom; Leiden, Netherlands, pp. xvii-li. (Table of Contents).

Pinkert, C. A. et al. (1987). "An Albumin Enhancer Located 10 kb Upstream Functions Along with its Promoters to Direct Efficient, Liver-Specific Expression inTransgenic Mice," *Genes & Dev.* 1:268-276.

Potempa, J. et al. (Jun. 1994). "The Serpin Superfamily of Proteinase Inhibitors: Structure, Function, and Regulation," *The J. of Biol. Chem.* 269(23):15957-15960.

Queen, C. and Baltimore, D. (Jul. 1983). "Immunoglobulin Gene Transcription Is Activated by Downstream Sequence Elements," *Cell* 33:741-748.

Sambrook, J. et al. (1989). *Molecular Cloning: A Laboratory Manual 2nd ed.* Cold Spring Harbor Laboratory Press, vol. 1-3., pp. xi-xxxviii. (Table of Contents).

Scopes, R. K. (1982). *Protein Purification: Principles and Practice.* Springer-Verlag, N.Y. pp. xiv-xiii. (Table of Contents).

Smith, D. B. and Johnson, K.S. (1988). "Single-Step Purification of Polypeptides Expressed in *Escherichia coli* as Fusions with Glutathione S-Transferase," *Gene* 67:31-40.

Stevenson-Stetler, W. G. et al. (Aug. 1990). "Tissue Inhibitor of Metalloproteinases-2 (TIMP-2) mRNA Expression in Tumor Cell Lines and Human Tumor Tissues," *The J. of Biol. Chem.* 265(23):13933-13938.

Teshima, T. et al. (May 1982). "A New Class of Heterocyclic Serine Protease Inhibitors," *The J. of Biol. Chem.* 257(9):5085-5091.

Turk, V. and Bode, W. (Jul. 1991). "The Cystatins: Protein Inhibitors of Cysteine Proteinases," *FEBS Lett.* 285(2):213-219.

Umezawa, H. et al. (May 1970). "Pepstatin, A New Pepsin Inhibitor Produced By Actinomycetes," *The J. of Antibiot.* 23(5):259-262.

Vogelmeier, C. et al. (1990). "Aerosolization of Recombinant SLPI to Augment Antineutrophil Elastase Protection of Pulmonary Epithelium," *J. Appl. Physiol.* 69(5):1843-1848.

Wada, K. et al. (1992). "Codon Usage Tabulated from the GenBank Genetic Sequence Data," *Nucleic Acids Res.* 20:2111-2118.

Weir, D. M., eds. *Handbook of Experimental Immunology in Four Volumes*, L.A. Herzenberg and C. Blackwell co-eds., Blackwell Scientific Publications, Oxford, Total pages 27. (Table of Contents for vols. 1-4).

Wilde, C. G. et al. (1994). "Cloning and Characterization of Human Tissue Inhibitor of Metalloproteinases-3," *DNA and Cell Biol.* 13(7):711-718.

Wilhem, S. M. et al. (Oct. 1987). "Human Skin Fibroblast Stromelysin: Structure, Glycosylation, Substrate Specificity, and Differential Expression in Normal and Tumorigenic Cells," *Proc. Natl. Acad. Sci.* 84:6725-6729.

Willenbrock, F. et al. (1993). "The Activity of the Tissue Inhibitors of Metalloproteinases Is Regulated by C-Terminal Domain Interactions: A Kinetic Analysis of the Inhibition of Gelatinase A," *Biochemistry* 32(16):4330-4337.

Winoto, A. and Baltimore, D. (1989). "A Novel, Inducible and T Cell-Specific Enhancer Located at the 3' End of the T Cell Receptor $\alpha$ Locus," *The EMBO Journal* 8(3):729-733.

Woessner, F. J., Jr. (May 1991). "Matrix Metalloproteinases and Their Inhibitors in Connective Tissue Remodeling," *The FASEB J.* 5:2145-2154.

Abe, T. et al. (1991). "Expression of the Secretory Leukoprotease Inhibitor Gene in Epithelial Cells," *Journal of Clinical Investigation* 87:2207-2215.

Barnes, P.J. (1999). "Novel Approaches and Targets for Treatment of Chronic Obstructive Pulmonary Disease," *American Journal of Respiratory and Critical Care Medicine* 160(5):S72-S79.

Lee, G.F. et al. (1997). "Potent Bifunctional Anticoagulants: Kunitz Domain—Tissue Factor Fusion Proteins," *Biochemistry* 36(19):5607-5611.

Schasteen, C.S. et al. (1991). "Synthetic Peptide Inhibitors of Complement Serine Proteases—III. Significant Increase In Inhibitor Potency Provides Further Support For The Functional Equivalence Hypothesis," *Molecular Immunology* 28(1/2):17-26.

Urwin, P.E. et al. (1998). "Enhanced Transgenic Plant Resistance to Nematodes by Dual Proteinase Inhibitor Constructs," *Planta* 204:472-479.

Bottomley, S.P. et al., Protein Engineering, vol. 11, No. 12, pp. 1243-1247 (1998).

Brantly, M.L. et al., Chest, vol. 100, No. 3, pp. 703-708 (1991); abstract.

Chughtai, B. et al., Journal of Aerosol Medicine, vol. 17, No. 4, pp. 289-298 (2004).

Cox, D.W. et al., Hum. Genet., vol. 61, No. 2, pp. 123-126 (1982); abstract.

Curiel, D. et al., Am. J. Respir. Cell Mol. Biol., vol. 1, No. 6, pp. 471-477 (1989); abstract.

Djie, M.Z. et al., The Journal of Biological Chemistry, vol. 272, No. 26, pp. 16268-16273 (1997).

Dobé, J. et al., The Journal of Biological Chemistry, vol. 279, No. 10, pp. 9264-9269 (2004).

Dykes, D.D. et al., Crit. Rev. Clin. Lab Sci., vol. 20, No. 2, pp. 115-151 (1984); abstract.

Dykes, D.D. et al., Hum. Hered, vol. 34, No. 5, pp. 308-310, (1984); abstract.

Eisenberg, S. P. et al., The Journal of Biological Chemistry, American Society of Biolochemical Biologists, vol. 265, No. 14, pp. 7976-7981 (1990).

Faber, J.P. et al., Am. J. Hum. Genet., vol. 55, No. 6, pp. 1113-1121 (1994).

Gahne, B. et al., Anim. Genet., vol. 17, No. 2, pp. 135-157 (1986); abstract.

Gaillard, I. et al., DNA, vol. 8, No. 2, pp. 87-99 (1989).

Goodwin, R.L. et al., Mol. Biol. Evol., vol. 13, No. 2, pp. 346-358 (1996); abstract.

Hopkins, P.C.R. et al., The Journal of Biological Chemistry, vol. 270, No. 20, pp. 11866-11871 (1995).

Im, H. et al., Protein Science, vol. 9, pp. 1497-1502 (2000).

Im, H. et al., The Journal of Biological Chemistry, vol. 277, No. 47, pp. 46347-46354 (2002).

Jeppsson J.O. et al., J. Chromatogr., vol. 26, No. 327, pp. 173-177 (1985).

Kelley, R.F. et al., Blood, vol. 89, No. 9, pp. 3219-3227 (1997).

Lukacs, C.M. et al., Biochemistry, vol. 37, No. 10, pp. 3297-3304 (1998).

Marshall, C.J., Philos Trans. R. Soc. Lond. B. Biol. Sci., vol. 342, No. 1300, pp. 101-119 (1993); abstract.

Martin, D.M.A. et al., The Faseb Journal, vol. 9, pp. 852-859 (1995); abstract.

Okayama, H. et al. Am. J. Hum. Genet., vol. 48, No. 6, pp. 1154-1158 (1991).

Okayama, H. et al. Biochem. Biophys. Res. Commun., vol. 162, No. 3, pp. 1560-1570 (1989); abstract.

Plotnick, M.I. et al., The Journal of Biological Chemistry, vol. 277, No. 33, pp. 29927-29935 (2002).

Rudolphus, A., Histochemical Journal, vol. 26, pp. 817-824 (1994).

Salahuddin, P., Indian J. Biochem. Biophys., vol. 28, No. 3, pp. 164-167 (1991).

Schick, C. et al., Proc. Natl. Acad. Sci. USA, vol. 95, pp. 13465-13470 (1998).

Schulze, A.J., Eur. J. Biochem., vol. 202, No. 3, pp. 1147-1155 (1991); abstract.

Sesboue R. et al., Hum. Hered, vol. 34, No. 2, pp. 105-113 (1984); abstract.

Silverman, G.A. et al., The Journal of Biological Chemistry, vol. 276, No. 36, pp. 33293-33296 (2001); abstract.

Stetler, G. et al., Nucleic Acids Research, vol. 14, No. 20, pp. 7883-7896 (1986).

Tanaka, T. et al., The Journal of Biological Chemistry, vol. 259, No. 13, pp. 8063-8065 (1984).

Wolfson A. J. et al., Protein and Peptide Letters, vol. 3, No. 5, pp. 293-300 (1996).

Wright, C.D., The Journal of Pharmacology and Experimental Therapeutics, vol. 289, No. 2, pp. 1007-1014 (1999).

Xue, Y. et al., Structure, vol. 6, No. 5, pp. 627-636 (1998).

Yamasaki, M. et al., The Journal of Biological Chemistry, vol. 278, No. 37, pp. 35524-35530 (2003).

Yuasa, I. et al., Hum. Genet, vol. 67, No. 2, pp. 209-212 (1984); abstract.

Zhou, A. et al., The Journal of Biological Chemistry, vol. 276, No. 29, pp. 27541-27547 (2001).

Bingle L. et al., "Susceptibility of Lung Epithelium to Neutrophil Elastase: Protection by Native Inhibitors," *Mediators of Inflammation*, 6: 345-354 (1997).

\* cited by examiner

SEQUENCE LISTING

<160> NUMBER OF SEQ ID NOS: 33

<210> SEQ ID NO 1
<211> LENGTH: 1182
<212> TYPE: DNA
<213> ORGANISM: Homo sapiens

<400> SEQUENCE: 1

```
gaagaccctc aaggcgacgc cgctcaaaaa accgacacca gtcatcacga ccaagaccat      60
ccgactttta ataaaattac tccaaattta gccgaatttg cttttctttt gtatagacaa     120
ttagctcatc aaagtaattc tactaacatt ttttttagtc ctgtttctat tgccactgct     180
ttcgccatgt tgagtttagg tactaaagcc gatacccatg acgagatttt agaaggttta     240
aactttaatt tgaccgaaat cccagaagcc caaattcacg agggttttca agagttgttg     300
agaactttga atcaacctga ttctcaattg caattaacta ctggtaacgg tttattttg      360
tctgaaggtt taaaattggt tgacaaattc ctagaagacg tcaagaaact atatcatagt     420
gaggcttttta ccgttaattt tggtgatact gaggaagcta aaaagcaaat taatgattat     480
gttgagaaag gcacccaggg taagatcgtt gacctagtaa agaattaga tcgtgatacc     540
gtcttcgcac tagttaacta tattttttc aagggtaagt gggaacgtcc tttcgaggtt     600
aaagatactg aagaggaaga ttttcatgtt gatcaagtta ctactgtcaa agttccaatg     660
atgaaaagac tgggtatgtt caatattcaa cattgcaaaa aattaagttc ttgggtctta     720
ttaatgaagt atttaggtaa cgctactgct attttttttt taccagacga aggtaagctt     780
caacatttag agaatgagtt gactcatgac attattacta aattttagaa gaacgaggat     840
cgtcgtagcg cttctctgca cctgccaaag ttaagtatca ccggtactta cgacttaaaa     900
tctgttttag gccagttagg tattaccaaa gttttttcta acggtgccga tttgagtggt     960
gttactgaag aagctccatt aaaattgagt aaagctgttc acaaagccgt cttaactatt    1020
gatgaaaagg gtaccgaggc cgccggcgct atgttcctgg aagctattcc aatgagcatt    1080
ccaccagaag ttaaatttaa taaaccattc gtttttctga tgatcgagca gaacactaaa    1140
agcccattgt ttatgggtaa ggttgtcaac ccaactcaga ag                       1182
```

<210> SEQ ID NO 2
<211> LENGTH: 394
<212> TYPE: PRT
<213> ORGANISM: Homo sapiens

<400> SEQUENCE: 2

```
Glu Asp Pro Gln Gly Asp Ala Ala Gln Lys Thr Asp Thr Ser His His
  1               5                  10                  15

Asp Gln Asp His Pro Thr Phe Asn Lys Ile Thr Pro Asn Leu Ala Glu
             20                  25                  30

Phe Ala Phe Ser Leu Tyr Arg Gln Leu Ala His Gln Ser Asn Ser Thr
         35                  40                  45

Asn Ile Phe Phe Ser Pro Val Ser Ile Ala Thr Ala Phe Ala Met Leu
     50                  55                  60

Ser Leu Gly Thr Lys Ala Asp Thr His Asp Glu Ile Leu Glu Gly Leu
 65                  70                  75                  80

Asn Phe Asn Leu Thr Glu Ile Pro Glu Ala Gln Ile His Glu Gly Phe
                 85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160
```

```
Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 3
<211> LENGTH: 321
<212> TYPE: DNA
<213> ORGANISM: Homo sapiens

<400> SEQUENCE: 3
tctggaaagt ctttcaaggc cggtgtttgt ccaccaaaga agtccgctca atgtttgaga      60
tacaagaagc cagaatgtca atccgactgg caatgtccag gtaagaagag atgttgtcca     120
gacacttgtg gtatcaagtg tctagaccca gttgacaccc caaacccaac tagaagaaag     180
ccaggtaagt gtccagttac ttacggtcaa tgtttgatgt tgaacccacc aaacttctgt     240
gaaatggacg gtcaatgtaa gagagacttg aagtgttgta tgggtatgtg tggtaagtcc     300
tgtgtttccc cagtcaaggc c                                               321

<210> SEQ ID NO 4
<211> LENGTH: 107
<212> TYPE: PRT
<213> ORGANISM: Homo sapiens

<400> SEQUENCE: 4

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30
```

```
Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
 50                  55                  60

Pro Val Thr Tyr Gly Gln Cys Leu Met Leu Asn Pro Pro Asn Phe Cys
 65                  70                  75                  80

Glu Met Asp Gly Gln Cys Lys Arg Asp Leu Lys Cys Cys Met Gly Met
                 85                  90                  95

Cys Gly Lys Ser Cys Val Ser Pro Val Lys Ala
            100                 105
```

<210> SEQ ID NO 5
<211> LENGTH: 552
<212> TYPE: DNA
<213> ORGANISM: Homo sapiens

<400> SEQUENCE: 5

```
tgcacctgtg tcccacccca ccacagacg gccttctgca attccgacct cgtcatcagg      60
gccaagttcg tggggacacc agaagtcaac cagaccacct tataccagcg ttatgagatc    120
aagatgacca agatgtataa agggttccaa gccttagggg atgccgctga catccggttc    180
gtctacaccc ccgccatgga gagtgtctgc ggatacttcc acaggtccca caaccgcagc    240
gaggagtttc tcattgctgg aaaactgcag gatggactct tgcacatcac tacctgcagt    300
ttcgtggctc cctggaacag cctgagctta gctcagcgcc gggcttcac caagacctac    360
actgttggct gtgaggaatg cacagtgttt ccctgtttat ccatcccctg caaactgcag    420
agtggcactc attgcttgtg gacggaccag ctcctccaag gctctgaaaa gggcttccag    480
tcccgtcacc ttgcctgcct gcctcgggag ccagggctgt gcacctggca gtccctgcgg    540
tcccagatag cc                                                        552
```

<210> SEQ ID NO 6
<211> LENGTH: 184
<212> TYPE: PRT
<213> ORGANISM: Homo sapiens

<400> SEQUENCE: 6

```
Cys Thr Cys Val Pro Pro His Pro Gln Thr Ala Phe Cys Asn Ser Asp
 1               5                  10                  15

Leu Val Ile Arg Ala Lys Phe Val Gly Thr Pro Glu Val Asn Gln Thr
                 20                  25                  30

Thr Leu Tyr Gln Arg Tyr Glu Ile Lys Met Thr Lys Met Tyr Lys Gly
         35                  40                  45

Phe Gln Ala Leu Gly Asp Ala Ala Asp Ile Arg Phe Val Tyr Thr Pro
 50                  55                  60

Ala Met Glu Ser Val Cys Gly Tyr Phe His Arg Ser His Asn Arg Ser
 65                  70                  75                  80

Glu Glu Phe Leu Ile Ala Gly Lys Leu Gln Asp Gly Leu Leu His Ile
                 85                  90                  95

Thr Thr Cys Ser Phe Val Ala Pro Trp Asn Ser Leu Ser Leu Ala Gln
            100                 105                 110

Arg Arg Gly Phe Thr Lys Thr Tyr Thr Val Gly Cys Glu Glu Cys Thr
        115                 120                 125

Val Phe Pro Cys Leu Ser Ile Pro Cys Lys Leu Gln Ser Gly Thr His
130                 135                 140

Cys Leu Trp Thr Asp Gln Leu Leu Gln Gly Ser Glu Lys Gly Phe Gln
```

145                 150                 155                 160
Ser Arg His Leu Ala Cys Leu Pro Arg Glu Pro Gly Leu Cys Thr Trp
                    165                 170                 175

Gln Ser Leu Arg Ser Gln Ile Ala
            180

<210> SEQ ID NO 7
<211> LENGTH: 1525
<212> TYPE: DNA
<213> ORGANISM: Homo sapiens

<400> SEQUENCE: 7
tctagaccat gtctggaaag tctttcaagg ccggtgtttg tccaccaaag aagtccgctc      60
aatgtttgag atacaagaag ccagaatgtc aatccgactg caatgtcca ggtaagaaga      120 gatgttgtcc agacacttgt ggtatcaagt gtctagaccc agttgacacc ccaaacccaa      180
ctagaagaaa gccaggtaag tgtccagtta cttacggtca atgtttgatg ttgaacccac      240
caaacttctg tgaaatggac ggtcaatgta agagagactt gaagtgttgt atgggtatgt      300
gtggtaagtc ctgtgtttcc ccagtcaagg ccatggaaga ccctcaaggc gacgccgctc      360
aaaaaaccga caccagtcat cacgaccaag accatccgac ttttaataaa attactccaa      420
atttagccga atttgctttt tctttgtata gacaattagc tcatcaaagt aattctacta      480 acatttttttt tagtcctgtt tctattgcca ctgctttcgc catgttgagt ttaggtacta      540
aagccgatac ccatgacgag attttagaag gtttaaactt taatttgacc gaaatcccag      600
aagcccaaat tcacgagggt tttcaagagt tgttgagaac tttgaatcaa cctgattctc      660
aattgcaatt aactactggt aacggtttat ttttgtctga aggtttaaaa ttggttgaca      720
aattcctaga agacgtcaag aaactatatc atagtgaggc ttttaccgtt aattttggtg      780
atactgagga agctaaaaag caaattaatg attatgttga gaaaggcacc cagggtaaga      840
tcgttgacct agttaaagaa ttagatcgtg ataccgtctt cgcactagtt aactatattt      900
ttttcaaggg taagtgggaa cgtccttttcg aggttaaaga tactgaagag gaagattttc      960
atgttgatca agttactact gtcaaagttc aatgatgaa aagactgggt atgttcaata      1020
ttcaacattg caaaaaatta agttcttggg tcttattaat gaagtattta ggtaacgcta      1080
ctgctatttt ttttttacca gacgaaggta agcttcaaca tttagagaat gagttgactc      1140
atgacattat tactaaattt ttagagaacg aggatcgtcg tagcgcttct ctgcacctgc      1200
caaagttaag tatcaccggt acttacgact taaaatctgt tttaggccag ttaggtatta      1260
ccaaagtttt ttctaacggt gccgatttga gtggtgttac tgaagaagct ccattaaaat      1320
tgagtaaagc tgttcacaaa gccgtcttaa ctattgatga aaagggtacc gaggccgccg      1380
gcgctatgtt cctggaagct attccaatga gcattccacc agaagttaaa tttaataaac      1440 cattcgttttt tctgatgatc gagcagaaca ctaaaagccc attgtttatg ggtaaggttg      1500
tcaacccaac tcagaagtag tcgac                                            1525

<210> SEQ ID NO 8
<211> LENGTH: 503
<212> TYPE: PRT
<213> ORGANISM: Homo sapiens

<400> SEQUENCE: 8

Met Ser Gly Lys Ser Phe Lys Ala Gly Val Cys Pro Pro Lys Lys Ser
 1               5                  10                  15

-continued

```
Ala Gln Cys Leu Arg Tyr Lys Lys Pro Glu Cys Gln Ser Asp Trp Gln
             20                  25                  30

Cys Pro Gly Lys Lys Arg Cys Cys Pro Asp Thr Cys Gly Ile Lys Cys
             35                  40                  45

Leu Asp Pro Val Asp Thr Pro Asn Pro Thr Arg Arg Lys Pro Gly Lys
 50                  55                  60

Cys Pro Val Thr Tyr Gly Gln Cys Leu Met Leu Asn Pro Pro Asn Phe
 65                  70                  75                  80

Cys Glu Met Asp Gly Gln Cys Lys Arg Asp Leu Lys Cys Cys Met Gly
                 85                  90                  95

Met Cys Gly Lys Ser Cys Val Ser Pro Val Lys Ala Met Glu Asp Pro
                100                 105                 110

Gln Gly Asp Ala Ala Gln Lys Thr Asp Thr Ser His His Asp Gln Asp
                115                 120                 125

His Pro Thr Phe Asn Lys Ile Thr Pro Asn Leu Ala Glu Phe Ala Phe
130                 135                 140

Ser Leu Tyr Arg Gln Leu Ala His Gln Ser Asn Ser Thr Asn Ile Phe
145                 150                 155                 160

Phe Ser Pro Val Ser Ile Ala Thr Ala Phe Ala Met Leu Ser Leu Gly
                165                 170                 175

Thr Lys Ala Asp Thr His Asp Glu Ile Leu Glu Gly Leu Asn Phe Asn
                180                 185                 190

Leu Thr Glu Ile Pro Glu Ala Gln Ile His Glu Gly Phe Gln Glu Leu
                195                 200                 205

Leu Arg Thr Leu Asn Gln Pro Asp Ser Gln Leu Gln Leu Thr Thr Gly
    210                 215                 220

Asn Gly Leu Phe Leu Ser Glu Gly Leu Lys Leu Val Asp Lys Phe Leu
225                 230                 235                 240

Glu Asp Val Lys Lys Leu Tyr His Ser Glu Ala Phe Thr Val Asn Phe
                245                 250                 255

Gly Asp Thr Glu Glu Ala Lys Lys Gln Ile Asn Asp Tyr Val Glu Lys
                260                 265                 270

Gly Thr Gln Gly Lys Ile Val Asp Leu Val Lys Glu Leu Asp Arg Asp
                275                 280                 285

Thr Val Phe Ala Leu Val Asn Tyr Ile Phe Phe Lys Gly Lys Trp Glu
            290                 295                 300

Arg Pro Phe Glu Val Lys Asp Thr Glu Glu Asp Phe His Val Asp
305                 310                 315                 320

Gln Val Thr Thr Val Lys Val Pro Met Met Lys Arg Leu Gly Met Phe
                325                 330                 335

Asn Ile Gln His Cys Lys Lys Leu Ser Ser Trp Val Leu Leu Met Lys
                340                 345                 350

Tyr Leu Gly Asn Ala Thr Ala Ile Phe Phe Leu Pro Asp Glu Gly Lys
            355                 360                 365

Leu Gln His Leu Glu Asn Glu Leu Thr His Asp Ile Ile Thr Lys Phe
    370                 375                 380

Leu Glu Asn Glu Asp Arg Arg Ser Ala Ser Leu His Leu Pro Lys Leu
385                 390                 395                 400

Ser Ile Thr Gly Thr Tyr Asp Leu Lys Ser Val Leu Gly Gln Leu Gly
                405                 410                 415

Ile Thr Lys Val Phe Ser Asn Gly Ala Asp Leu Ser Gly Val Thr Glu
            420                 425                 430

Glu Ala Pro Leu Lys Leu Ser Lys Ala Val His Lys Ala Val Leu Thr
```

```
                435              440              445
Ile Asp Glu Lys Gly Thr Glu Ala Ala Gly Ala Met Phe Leu Glu Ala
    450              455              460

Ile Pro Met Ser Ile Pro Pro Glu Val Lys Phe Asn Lys Pro Phe Val
465              470              475              480

Phe Leu Met Ile Glu Gln Asn Thr Lys Ser Pro Leu Phe Met Gly Lys
            485              490              495

Val Val Asn Pro Thr Gln Lys
        500

<210> SEQ ID NO 9
<211> LENGTH: 1756
<212> TYPE: DNA
<213> ORGANISM: Homo sapiens

<400> SEQUENCE: 9
```

| | | | | |
|---|---|---|---|---|
| tctagaccat gtgcacctgt gtcccacccc acccacagac ggccttctgc aattccgacc | 60 |
| tcgtcatcag ggccaagttc gtggggacac cagaagtcaa ccagaccacc ttataccagc | 120 |
| gttatgagat caagatgacc aagatgtata aggggttcca agcctttaggg gatgccgctg | 180 |
| acatccggtt cgtctacacc cccgccatgg agagtgtctg cggatacttc cacaggtccc | 240 |
| acaaccgcag cgaggagttt ctcattgctg gaaaactgca ggatggactc ttgcacatca | 300 |
| ctacctgcag tttcgtggct ccctggaaca gcctgagctt agctcagcgc cggggcttca | 360 |
| ccaagaccta cactgttggc tgtgaggaat gcacagtgtt tccctgttta tccatcccct | 420 |
| gcaaactgca gagtggcact cattgcttgt ggacggacca gctcctccaa ggctctgaaa | 480 |
| agggcttcca gtcccgtcac cttgcctgcc tgcctcggga gccagggctg tgcacctggc | 540 |
| agtccctgcg gtcccagata gccatggaag accctcaagg cgacgccgct caaaaaaccg | 600 |
| acaccagtca tcacgaccaa gaccatccga ctttaataa aattactcca aatttagccg | 660 |
| aatttgcttt ttcttttgtat agacaattag ctcatcaaag taattctact aacatttttt | 720 |
| ttagtcctgt ttctattgcc actgctttcg ccatgttgag tttaggtact aaagccgata | 780 |
| cccatgacga gattttagaa ggtttaaact ttaatttgac cgaaatccca gaagcccaaa | 840 |
| ttcacgaggg ttttcaagag ttgttgagaa ctttgaatca acctgattct caattgcaat | 900 |
| taactactgg taacggttta ttttttgtctg aaggtttaaa attggttgac aaattcctag | 960 |
| aagacgtcaa gaaactatat catagtgagg cttttaccgt taattttggt gatactgagg | 1020 |
| aagctaaaaa gcaaattaat gattatgttg agaaaggcac ccagggtaag atcgttgacc | 1080 |
| tagttaaaga attagatcgt gataccgtct tcgcactagt taactatatt tttttcaagg | 1140 |
| gtaagtggga acgtcctttc gaggttaaag atactgaaga ggaagatttt catgttgatc | 1200 |
| aagttactac tgtcaaagtt ccaatgatga aaagactggg tatgttcaat attcaacatt | 1260 |
| gcaaaaaatt aagttcttgg gtcttattaa tgaagtattt aggtaacgct actgctattt | 1320 |
| ttttttttacc agacgaaggt aagcttcaac atttagagaa tgagttgact catgacatta | 1380 |
| ttactaaatt tttagagaac gaggatcgtc gtagcgcttc tctgcacctg ccaaagttaa | 1440 |
| gtatcaccgg tacttacgac ttaaaatctg ttttaggcca gttaggtatt accaaagttt | 1500 |
| tttctaacgg tgccgatttg agtggtgtta ctgaagaagc tccattaaaa ttgagtaaag | 1560 |
| ctgttcacaa agccgtctta actattgatg aaaagggtac cgaggccgcc ggcgctatgt | 1620 |
| tcctggaagc tattccaatg agcattccac cagaagttaa atttaataaa ccattcgttt | 1680 |
| ttctgatgat cgagcagaac actaaaagcc cattgtttat gggtaaggtt gtcaacccaa | 1740 | ctcagaagta gtcgac 1756

<210> SEQ ID NO 10
<211> LENGTH: 580
<212> TYPE: PRT
<213> ORGANISM: Homo sapiens

<400> SEQUENCE: 10

Met Cys Thr Cys Val Pro Pro His Pro Gln Thr Ala Phe Cys Asn Ser
1               5                   10                  15

Asp Leu Val Ile Arg Ala Lys Phe Val Gly Thr Pro Glu Val Asn Gln
            20                  25                  30

Thr Thr Leu Tyr Gln Arg Tyr Glu Ile Lys Met Thr Lys Met Tyr Lys
        35                  40                  45

Gly Phe Gln Ala Leu Gly Asp Ala Ala Asp Ile Arg Phe Val Tyr Thr
    50                  55                  60

Pro Ala Met Glu Ser Val Cys Gly Tyr Phe His Arg Ser His Asn Arg
65                  70                  75                  80

Ser Glu Glu Phe Leu Ile Ala Gly Lys Leu Gln Asp Gly Leu Leu His
                85                  90                  95

Ile Thr Thr Cys Ser Phe Val Ala Pro Trp Asn Ser Leu Ser Leu Ala
            100                 105                 110

Gln Arg Arg Gly Phe Thr Lys Thr Tyr Thr Val Gly Cys Glu Glu Cys
        115                 120                 125

Thr Val Phe Pro Cys Leu Ser Ile Pro Cys Lys Leu Gln Ser Gly Thr
    130                 135                 140

His Cys Leu Trp Thr Asp Gln Leu Leu Gln Gly Ser Glu Lys Gly Phe
145                 150                 155                 160

Gln Ser Arg His Leu Ala Cys Leu Pro Arg Glu Pro Gly Leu Cys Thr
                165                 170                 175

Trp Gln Ser Leu Arg Ser Gln Ile Ala Met Glu Asp Pro Gln Gly Asp
            180                 185                 190

Ala Ala Gln Lys Thr Asp Thr Ser His His Asp Gln Asp His Pro Thr
        195                 200                 205

Phe Asn Lys Ile Thr Pro Asn Leu Ala Glu Phe Ala Phe Ser Leu Tyr
    210                 215                 220

Arg Gln Leu Ala His Gln Ser Asn Ser Thr Asn Ile Phe Phe Ser Pro
225                 230                 235                 240

Val Ser Ile Ala Thr Ala Phe Ala Met Leu Ser Leu Gly Thr Lys Ala
                245                 250                 255

Asp Thr His Asp Glu Ile Leu Glu Gly Leu Asn Phe Asn Leu Thr Glu
            260                 265                 270

Ile Pro Glu Ala Gln Ile His Glu Gly Phe Gln Glu Leu Leu Arg Thr
        275                 280                 285

Leu Asn Gln Pro Asp Ser Gln Leu Gln Leu Thr Thr Gly Asn Gly Leu
    290                 295                 300

Phe Leu Ser Glu Gly Leu Lys Leu Val Asp Lys Phe Leu Glu Asp Val
305                 310                 315                 320

Lys Lys Leu Tyr His Ser Glu Ala Phe Thr Val Asn Phe Gly Asp Thr
                325                 330                 335

Glu Glu Ala Lys Lys Gln Ile Asn Asp Tyr Val Glu Lys Gly Thr Gln
            340                 345                 350

Gly Lys Ile Val Asp Leu Val Lys Glu Leu Asp Arg Asp Thr Val Phe
        355                 360                 365

-continued

```
Ala Leu Val Asn Tyr Ile Phe Phe Lys Gly Lys Trp Glu Arg Pro Phe
        370                 375                 380

Glu Val Lys Asp Thr Glu Glu Asp Phe His Val Asp Gln Val Thr
385                 390                 395                 400

Thr Val Lys Val Pro Met Met Lys Arg Leu Gly Met Phe Asn Ile Gln
                    405                 410                 415

His Cys Lys Lys Leu Ser Ser Trp Val Leu Leu Met Lys Tyr Leu Gly
                420                 425                 430

Asn Ala Thr Ala Ile Phe Phe Leu Pro Asp Glu Gly Lys Leu Gln His
            435                 440                 445

Leu Glu Asn Glu Leu Thr His Asp Ile Ile Thr Lys Phe Leu Glu Asn
        450                 455                 460

Glu Asp Arg Arg Ser Ala Ser Leu His Leu Pro Lys Leu Ser Ile Thr
465                 470                 475                 480

Gly Thr Tyr Asp Leu Lys Ser Val Leu Gly Gln Leu Gly Ile Thr Lys
                    485                 490                 495

Val Phe Ser Asn Gly Ala Asp Leu Ser Gly Val Thr Glu Glu Ala Pro
                500                 505                 510

Leu Lys Leu Ser Lys Ala Val His Lys Ala Val Leu Thr Ile Asp Glu
            515                 520                 525

Lys Gly Thr Glu Ala Ala Gly Ala Met Phe Leu Glu Ala Ile Pro Met
        530                 535                 540

Ser Ile Pro Pro Glu Val Lys Phe Asn Lys Pro Phe Val Phe Leu Met
545                 550                 555                 560

Ile Glu Gln Asn Thr Lys Ser Pro Leu Phe Met Gly Lys Val Val Asn
                    565                 570                 575

Pro Thr Gln Lys
            580

<210> SEQ ID NO 11
<211> LENGTH: 5
<212> TYPE: PRT
<213> ORGANISM: Homo sapiens

<400> SEQUENCE: 11

Gln Val Val Ala Gly
1               5

<210> SEQ ID NO 12
<211> LENGTH: 5
<212> TYPE: PRT
<213> ORGANISM: Bacteria (streptomyces)
<220> FEATURE:
<221> NAME/KEY: MOD_RES
<222> LOCATION: 1
<223> OTHER INFORMATION: Xaa= valine modified with N-terminal isovaleryl
      group
<220> FEATURE:
<221> NAME/KEY: MOD_RES
<222> LOCATION: 3, 5
<223> OTHER INFORMATION: Xaa= statin

<400> SEQUENCE: 12

Xaa Val Xaa Ala Xaa
1               5

<210> SEQ ID NO 13
<211> LENGTH: 1582
<212> TYPE: DNA
<213> ORGANISM: Homo sapiens
```

-continued

```
<400> SEQUENCE: 13
tctagaccat gtgcacctgt gtcccacccc acccacagac ggccttctgc aattccgacc      60
tcgtcatcag ggccaagttc gtggggacac cagaagtcaa ccagaccacc ttataccagc     120
gttatgagat caagatgacc aagatgtata aagggttcca agccttaggg gatgccgctg     180
acatccggtt cgtctacacc cccgccatgg agagtgtctg cggatacttc cacaggtccc     240
acaaccgcag cgaggagttt ctcattgctg aaaaactgca ggatggactc ttgcacatca     300
ctacctgcag tttcgtggct ccctggaaca gcctgagctt agctcagcgc cggggcttca     360
ccaagacgta tactgttggc tgtgaggaaa tggaagaccc tcaaggcgac gccgctcaaa     420
aaaccgacac cagtcatcac gaccaagacc atccgacttt taataaaatt actccaaatt     480
tagccgaatt tgcttttttct ttgtatagac aattagctca tcaaagtaat tctactaaca     540
ttttttttag tcctgtttct attgccactg ctttcgccat gttgagttta ggtactaaag     600
ccgataccca tgacgagatt ttagaaggtt taaactttaa tttgaccgaa atcccagaag     660
cccaaattca cgagggtttt caagagttgt tgagaacttt gaatcaacct gattctcaat     720
tgcaattaac tactggtaac ggtttatttt tgtctgaagg tttaaaattg gttgacaaat     780
tcctagaaga cgtcaagaaa ctatatcata gtgaggcttt taccgttaat tttggtgata     840
ctgaggaagc taaaaagcaa attaatgatt atgttgagaa aggcacccag ggtaagatcg     900
ttgacctagt taaagaatta gatcgtgata ccgtcttcgc actagttaac tatatttttt     960
tcaagggtaa gtgggaacgt cctttcgagg ttaaagatac tgaagaggaa gattttcatg    1020
ttgatcaagt tactactgtc aaagttccaa tgatgaaaag actgggtatg ttcaatattc    1080
aacattgcaa aaaattaagt tcttgggtct tattaatgaa gtatttaggt aacgctactg    1140 ctatttttt tttaccagac gaaggtaagc ttcaacattt agagaatgag ttgactcatg    1200
acattattac taaattttta gagaacgagg atcgtcgtag cgcttctctg cacctgccaa    1260
agttaagtat caccggtact tacgacttaa aatctgtttt aggccagtta ggtattacca    1320
aagttttttc taacggtgcc gatttgagtg gtgttactga agaagctcca ttaaaattga    1380
gtaaagctgt tcacaaagcc gtcttaacta ttgatgaaaa gggtaccgag gccgccggcg    1440
ctatgttcct ggaagctatt ccaatgagca ttccaccaga agttaaattt aataaaccat    1500
tcgtttttct gatgatcgag cagaacacta aaagcccatt gtttatgggt aaggttgtca    1560
acccaactca gaagtagtcg ac                                              1582
```

<210> SEQ ID NO 14
<211> LENGTH: 522
<212> TYPE: PRT
<213> ORGANISM: Homo sapiens

<400> SEQUENCE: 14

Met Cys Thr Cys Val Pro Pro His Pro Gln Thr Ala Phe Cys Asn Ser
1               5                   10                  15

Asp Leu Val Ile Arg Ala Lys Phe Val Gly Thr Pro Glu Val Asn Gln
            20                  25                  30

Thr Thr Leu Tyr Gln Arg Tyr Glu Ile Lys Met Thr Lys Met Tyr Lys
        35                  40                  45

Gly Phe Gln Ala Leu Gly Asp Ala Ala Asp Ile Arg Phe Val Tyr Thr
    50                  55                  60

Pro Ala Met Glu Ser Val Cys Gly Tyr Phe His Arg Ser His Asn Arg
65                  70                  75                  80

```
Ser Glu Glu Phe Leu Ile Ala Gly Lys Leu Gln Asp Gly Leu Leu His
                 85                  90                  95

Ile Thr Thr Cys Ser Phe Val Ala Pro Trp Asn Ser Leu Ser Leu Ala
            100                 105                 110

Gln Arg Arg Gly Phe Thr Lys Thr Tyr Thr Val Gly Cys Glu Glu Met
        115                 120                 125

Glu Asp Pro Gln Gly Asp Ala Ala Gln Lys Thr Asp Thr Ser His His
    130                 135                 140

Asp Gln Asp His Pro Thr Phe Asn Lys Ile Thr Pro Asn Leu Ala Glu
145                 150                 155                 160

Phe Ala Phe Ser Leu Tyr Arg Gln Leu Ala His Gln Ser Asn Ser Thr
                165                 170                 175

Asn Ile Phe Phe Ser Pro Val Ser Ile Ala Thr Ala Phe Ala Met Leu
                180                 185                 190

Ser Leu Gly Thr Lys Ala Asp Thr His Asp Glu Ile Leu Glu Gly Leu
            195                 200                 205

Asn Phe Asn Leu Thr Glu Ile Pro Glu Ala Gln Ile His Glu Gly Phe
        210                 215                 220

Gln Glu Leu Leu Arg Thr Leu Asn Gln Pro Asp Ser Gln Leu Gln Leu
225                 230                 235                 240

Thr Thr Gly Asn Gly Leu Phe Leu Ser Glu Gly Leu Lys Leu Val Asp
                245                 250                 255

Lys Phe Leu Glu Asp Val Lys Lys Leu Tyr His Ser Glu Ala Phe Thr
                260                 265                 270

Val Asn Phe Gly Asp Thr Glu Glu Ala Lys Lys Gln Ile Asn Asp Tyr
            275                 280                 285

Val Glu Lys Gly Thr Gln Gly Lys Ile Val Asp Leu Val Lys Glu Leu
        290                 295                 300

Asp Arg Asp Thr Val Phe Ala Leu Val Asn Tyr Ile Phe Phe Lys Gly
305                 310                 315                 320

Lys Trp Glu Arg Pro Phe Glu Val Lys Asp Thr Glu Glu Glu Asp Phe
                325                 330                 335

His Val Asp Gln Val Thr Thr Val Lys Val Pro Met Met Lys Arg Leu
            340                 345                 350

Gly Met Phe Asn Ile Gln His Cys Lys Lys Leu Ser Ser Trp Val Leu
        355                 360                 365

Leu Met Lys Tyr Leu Gly Asn Ala Thr Ala Ile Phe Phe Leu Pro Asp
    370                 375                 380

Glu Gly Lys Leu Gln His Leu Glu Asn Glu Leu Thr His Asp Ile Ile
385                 390                 395                 400

Thr Lys Phe Leu Glu Asn Glu Asp Arg Arg Ser Ala Ser Leu His Leu
                405                 410                 415

Pro Lys Leu Ser Ile Thr Gly Thr Tyr Asp Leu Lys Ser Val Leu Gly
            420                 425                 430

Gln Leu Gly Ile Thr Lys Val Phe Ser Asn Gly Ala Asp Leu Ser Gly
        435                 440                 445

Val Thr Glu Glu Ala Pro Leu Lys Leu Ser Lys Ala Val His Lys Ala
    450                 455                 460

Val Leu Thr Ile Asp Glu Lys Gly Thr Glu Ala Ala Gly Ala Met Phe
465                 470                 475                 480

Leu Glu Ala Ile Pro Met Ser Ile Pro Pro Glu Val Lys Phe Asn Lys
                485                 490                 495
```

-continued

```
Pro Phe Val Phe Leu Met Ile Glu Gln Asn Thr Lys Ser Pro Leu Phe
            500                 505                 510

Met Gly Lys Val Val Asn Pro Thr Gln Lys
        515                 520
```

<210> SEQ ID NO 15
<211> LENGTH: 1525
<212> TYPE: DNA
<213> ORGANISM: Homo sapiens

<400> SEQUENCE: 15

```
tctagaccat ggaagaccct caaggcgacg ccgctcaaaa aaccgacacc agtcatcacg      60
accaagacca tccgactttt aataaaatta ctccaaattt agccgaattt gcttttctt     120
tgtatagaca attagctcat caaagtaatt ctactaacat ttttttttagt cctgtttcta   180
ttgccactgc tttcgccatg ttgagtttag gtactaaagc cgatacccat gacgagattt    240
tagaaggttt aaactttaat ttgaccgaaa tcccagaagc ccaaattcac gagggttttc    300
aagagttgtt gagaactttg aatcaacctg attctcaatt gcaattaact actggtaacg   360
gtttattttt gtctgaaggt ttaaaattgg ttgacaaatt cctagaagac gtcaagaaac    420
tatatcatag tgaggctttt accgttaatt ttggtgatac tgaggaagct aaaaagcaaa   480
ttaatgatta tgttgagaaa ggcacccagg gtaagatcgt tgacctagtt aaagaattag    540
atcgtgatac cgtcttcgca ctagttaact atatttttt caagggtaag tgggaacgtc    600
ctttcgaggt taaagatact gaagaggaag attttcatgt tgatcaagtt actactgtca   660
aagttccaat gatgaaaaga ctgggtatgt tcaatattca acattgcaaa aaattaagtt    720
cttgggtctt attaatgaag tatttaggta acgctactgc tattttttt ttaccagacg    780
aaggtaagct tcaacattta gagaatgagt tgactcatga cattattact aaatttttag    840
agaacgagga tcgtcgtagc gcttctctgc acctgccaaa gttaagtatc accggtactt    900
acgacttaaa atctgtttta ggccagttag gtattaccaa agttttttct aacggtgccg    960
atttgagtgg tgttactgaa gaagctccat taaaattgag taaagctgtt cacaaagccg   1020
tcttaactat tgatgaaaag ggtaccgagg ccgccggcgc tatgttcctg gaagctattc   1080
caatgagcat tccaccagaa gttaaattta taaaccatt cgttttttctg atgatcgagc   1140
agaacactaa aagcccattg tttatgggta aggttgtcaa cccaactcag aagatgtccg   1200
gaaagtcttt caaggccggt gtttgtccac caaagaagtc cgctcaatgt ttgagataca   1260
agaagccaga atgtcaatcc gactggcaat gtccaggtaa gaagagatgt tgtccagaca   1320
cttgtggtat caagtgtcta gacccagtta caccccaaa cccaactaga gaaaagccag   1380
gtaagtgtcc agttacttac ggtcaatgtt tgatgttgaa cccaccaaac ttctgtgaaa   1440
tggacggtca atgtaagaga gacttgaagt gttgtatggg tatgtgtggt aagtcctgtg   1500
tttccccagt caaggcctag tcgac                                          1525
```

<210> SEQ ID NO 16
<211> LENGTH: 503
<212> TYPE: PRT
<213> ORGANISM: Homo sapiens

<400> SEQUENCE: 16

```
Met Glu Asp Pro Gln Gly Asp Ala Ala Gln Lys Thr Asp Thr Ser His
  1               5                  10                  15

His Asp Gln Asp His Pro Thr Phe Asn Lys Ile Thr Pro Asn Leu Ala
             20                  25                  30
```

-continued

```
Glu Phe Ala Phe Ser Leu Tyr Arg Gln Leu Ala His Gln Ser Asn Ser
         35                  40                  45

Thr Asn Ile Phe Phe Ser Pro Val Ser Ile Ala Thr Ala Phe Ala Met
     50                  55                  60

Leu Ser Leu Gly Thr Lys Ala Asp Thr His Asp Glu Ile Leu Glu Gly
 65                  70                  75                  80

Leu Asn Phe Asn Leu Thr Glu Ile Pro Glu Ala Gln Ile His Glu Gly
                 85                  90                  95

Phe Gln Glu Leu Leu Arg Thr Leu Asn Gln Pro Asp Ser Gln Leu Gln
             100                 105                 110

Leu Thr Thr Gly Asn Gly Leu Phe Leu Ser Glu Gly Leu Lys Leu Val
         115                 120                 125

Asp Lys Phe Leu Glu Asp Val Lys Lys Leu Tyr His Ser Glu Ala Phe
     130                 135                 140

Thr Val Asn Phe Gly Asp Thr Glu Glu Ala Lys Lys Gln Ile Asn Asp
145                 150                 155                 160

Tyr Val Glu Lys Gly Thr Gln Gly Lys Ile Val Asp Leu Val Lys Glu
                165                 170                 175

Leu Asp Arg Asp Thr Val Phe Ala Leu Val Asn Tyr Ile Phe Phe Lys
            180                 185                 190

Gly Lys Trp Glu Arg Pro Phe Glu Val Lys Asp Thr Glu Glu Glu Asp
        195                 200                 205

Phe His Val Asp Gln Val Thr Thr Val Lys Val Pro Met Met Lys Arg
    210                 215                 220

Leu Gly Met Phe Asn Ile Gln His Cys Lys Lys Leu Ser Ser Trp Val
225                 230                 235                 240

Leu Leu Met Lys Tyr Leu Gly Asn Ala Thr Ala Ile Phe Phe Leu Pro
                245                 250                 255

Asp Glu Gly Lys Leu Gln His Leu Glu Asn Glu Leu Thr His Asp Ile
            260                 265                 270

Ile Thr Lys Phe Leu Glu Asn Glu Asp Arg Arg Ser Ala Ser Leu His
        275                 280                 285

Leu Pro Lys Leu Ser Ile Thr Gly Thr Tyr Asp Leu Lys Ser Val Leu
    290                 295                 300

Gly Gln Leu Gly Ile Thr Lys Val Phe Ser Asn Gly Ala Asp Leu Ser
305                 310                 315                 320

Gly Val Thr Glu Glu Ala Pro Leu Lys Leu Ser Lys Ala Val His Lys
                325                 330                 335

Ala Val Leu Thr Ile Asp Glu Lys Gly Thr Glu Ala Ala Gly Ala Met
            340                 345                 350

Phe Leu Glu Ala Ile Pro Met Ser Ile Pro Pro Glu Val Lys Phe Asn
        355                 360                 365

Lys Pro Phe Val Phe Leu Met Ile Glu Gln Asn Thr Lys Ser Pro Leu
    370                 375                 380

Phe Met Gly Lys Val Val Asn Pro Thr Gln Lys Met Ser Gly Lys Ser
385                 390                 395                 400

Phe Lys Ala Gly Val Cys Pro Pro Lys Ser Ala Gln Cys Leu Arg
                405                 410                 415

Tyr Lys Lys Pro Glu Cys Gln Ser Asp Trp Gln Cys Pro Gly Lys Lys
            420                 425                 430

Arg Cys Cys Pro Asp Thr Cys Gly Ile Lys Cys Leu Asp Pro Val Asp
        435                 440                 445
```

```
Thr Pro Asn Pro Thr Arg Arg Lys Pro Gly Lys Cys Pro Val Thr Tyr
    450                 455                 460
Gly Gln Cys Leu Met Leu Asn Pro Pro Asn Phe Cys Glu Met Asp Gly
465                 470                 475                 480
Gln Cys Lys Arg Asp Leu Lys Cys Cys Met Gly Met Cys Gly Lys Ser
                485                 490                 495
Cys Val Ser Pro Val Lys Ala
            500

<210> SEQ ID NO 17
<211> LENGTH: 1756
<212> TYPE: DNA
<213> ORGANISM: Homo sapiens

<400> SEQUENCE: 17
tctagaccat ggaagaccct caaggcgacg ccgctcaaaa aaccgacacc agtcatcacg      60
accaagacca tccgactttt aataaaatta ctccaaattt agccgaattt gcttttcttt     120
tgtatagaca attagctcat caaagtaatt ctactaacat tttttttagt cctgtttcta     180
ttgccactgc tttcgccatg ttgagtttag tactaaagc cgataccat gacgagattt       240
tagaaggttt aaactttaat ttgaccgaaa tcccagaagc ccaaattcac gagggttttc     300
aagagttgtt gagaactttg aatcaacctg attctcaatt gcaattaact actggtaacg     360
gtttattttt gtctgaaggt ttaaaattgg ttgacaaatt cctagaagac gtcaagaaac     420
tatatcatag tgaggctttt accgttaatt ttggtgatac tgaggaagct aaaaagcaaa     480
ttaatgatta tgttgagaaa ggcacccagg gtaagatcgt tgacctagtt aaagaattag     540
atcgtgatac cgtcttcgca ctagttaact atatttttt caagggtaag tgggaacgtc      600
ctttcgaggt taaagatact gaagaggaag attttcatgt tgatcaagtt actactgtca     660
aagttccaat gatgaaaaga ctgggtatgt tcaatattca acattgcaaa aaattaagtt     720
cttgggtctt attaatgaag tatttaggta acgctactgc tatttttttt ttaccagacg     780
aaggtaagct tcaacattta gagaatgagt tgactcatga cattattact aaattttag      840
agaacgagga tcgtcgtagc gcttctctgc acctgccaaa gttaagtatc accggtactt     900
acgacttaaa atctgtttta ggccagttag gtattaccaa agttttttct aacggtaccg     960
atttgagtgg tgttactgaa gaagctccat taaaattgag taaagctgtt cacaaagccg    1020
tcttaactat tgatgaaaag ggtaccgagg ccgccggcgc tatgttcctg gaagctattc    1080
caatgagcat tccaccagaa gttaaattta ataaaccatt cgttttcctg atgatcgagc    1140
agaacactaa aagcccattg tttatgggta aggttgtcaa cccaactcag aagatgtgca    1200
cgtgtgtccc acccccaccca cagacggcct tctgcaattc cgacctcgtc atcagggcca    1260
agttcgtggg gacaccagaa gtcaaccaga ccaccttata ccagcgttat gagatcaaga    1320
tgaccaagat gtataaaggg ttccaagcct taggggatgc cgctgacatc cggttcgtct    1380
acaccccgc catggagagt gtctgcggat acttccacag gtcccacaac cgcagcgagg    1440
agtttctcat tgctgaaaaa ctgcaggatg gactcttgca catcactacc tgcagtttcg    1500
tggctccctg gaacagcctg agcttagctc agcgccgggg cttcaccaag acctacactg    1560
ttggctgtga ggaatgcaca gtgtttccct gtttatccat cccctgcaaa ctgcagagtg    1620
gcactcattg cttgtggacg gaccagctcc tccaaggctc tgaaaagggc ttccagtccc    1680
gtcaccttgc ctgcctgcct cgggagccag ggctgtgcac ctggcagtcc ctgcggtccc    1740
agatagccta gtcgac                                                    1756
```

<210> SEQ ID NO 18
<211> LENGTH: 580
<212> TYPE: PRT
<213> ORGANISM: Homo sapiens

<400> SEQUENCE: 18

```
Met Glu Asp Pro Gln Gly Asp Ala Ala Gln Lys Thr Asp Thr Ser His
  1               5                  10                  15

His Asp Gln Asp His Pro Thr Phe Asn Lys Ile Thr Pro Asn Leu Ala
             20                  25                  30

Glu Phe Ala Phe Ser Leu Tyr Arg Gln Leu Ala His Gln Ser Asn Ser
         35                  40                  45

Thr Asn Ile Phe Phe Ser Pro Val Ser Ile Ala Thr Ala Phe Ala Met
     50                  55                  60

Leu Ser Leu Gly Thr Lys Ala Asp Thr His Asp Glu Ile Leu Glu Gly
 65                  70                  75                  80

Leu Asn Phe Asn Leu Thr Glu Ile Pro Glu Ala Gln Ile His Glu Gly
                 85                  90                  95

Phe Gln Glu Leu Leu Arg Thr Leu Asn Gln Pro Asp Ser Gln Leu Gln
            100                 105                 110

Leu Thr Thr Gly Asn Gly Leu Phe Leu Ser Glu Gly Leu Lys Leu Val
        115                 120                 125

Asp Lys Phe Leu Glu Asp Val Lys Lys Leu Tyr His Ser Glu Ala Phe
130                 135                 140

Thr Val Asn Phe Gly Asp Thr Glu Glu Ala Lys Lys Gln Ile Asn Asp
145                 150                 155                 160

Tyr Val Glu Lys Gly Thr Gln Gly Lys Ile Val Asp Leu Val Lys Glu
                165                 170                 175

Leu Asp Arg Asp Thr Val Phe Ala Leu Val Asn Tyr Ile Phe Phe Lys
            180                 185                 190

Gly Lys Trp Glu Arg Pro Phe Glu Val Lys Asp Thr Glu Glu Glu Asp
        195                 200                 205

Phe His Val Asp Gln Val Thr Thr Val Lys Val Pro Met Met Lys Arg
    210                 215                 220

Leu Gly Met Phe Asn Ile Gln His Cys Lys Lys Leu Ser Ser Trp Val
225                 230                 235                 240

Leu Leu Met Lys Tyr Leu Gly Asn Ala Thr Ala Ile Phe Phe Leu Pro
                245                 250                 255

Asp Glu Gly Lys Leu Gln His Leu Glu Asn Glu Leu Thr His Asp Ile
            260                 265                 270

Ile Thr Lys Phe Leu Glu Asn Glu Asp Arg Arg Ser Ala Ser Leu His
        275                 280                 285

Leu Pro Lys Leu Ser Ile Thr Gly Thr Tyr Asp Leu Lys Ser Val Leu
    290                 295                 300

Gly Gln Leu Gly Ile Thr Lys Val Phe Ser Asn Gly Ala Asp Leu Ser
305                 310                 315                 320

Gly Val Thr Glu Glu Ala Pro Leu Lys Leu Ser Lys Ala Val His Lys
                325                 330                 335

Ala Val Leu Thr Ile Asp Glu Lys Gly Thr Glu Ala Ala Gly Ala Met
            340                 345                 350

Phe Leu Glu Ala Ile Pro Met Ser Ile Pro Pro Glu Val Lys Phe Asn
        355                 360                 365

Lys Pro Phe Val Phe Leu Met Ile Glu Gln Asn Thr Lys Ser Pro Leu
```

```
                370             375             380
Phe Met Gly Lys Val Val Asn Pro Thr Gln Lys Met Cys Thr Cys Val
385                 390                 395                 400

Pro Pro His Pro Gln Thr Ala Phe Cys Asn Ser Asp Leu Val Ile Arg
            405                 410                 415

Ala Lys Phe Val Gly Thr Pro Glu Val Asn Gln Thr Thr Leu Tyr Gln
                420                 425                 430

Arg Tyr Glu Ile Lys Met Thr Lys Met Tyr Lys Gly Phe Gln Ala Leu
            435                 440                 445

Gly Asp Ala Ala Asp Ile Arg Phe Val Tyr Thr Pro Ala Met Glu Ser
450                 455                 460

Val Cys Gly Tyr Phe His Arg Ser His Asn Arg Ser Glu Glu Phe Leu
465                 470                 475                 480

Ile Ala Gly Lys Leu Gln Asp Gly Leu Leu His Ile Thr Thr Cys Ser
                485                 490                 495

Phe Val Ala Pro Trp Asn Ser Leu Ser Leu Ala Gln Arg Arg Gly Phe
                500                 505                 510

Thr Lys Thr Tyr Thr Val Gly Cys Glu Glu Cys Thr Val Phe Pro Cys
            515                 520                 525

Leu Ser Ile Pro Cys Lys Leu Gln Ser Gly Thr His Cys Leu Trp Thr
530                 535                 540

Asp Gln Leu Leu Gln Gly Ser Glu Lys Gly Phe Gln Ser Arg His Leu
545                 550                 555                 560

Ala Cys Leu Pro Arg Glu Pro Gly Leu Cys Thr Trp Gln Ser Leu Arg
                565                 570                 575

Ser Gln Ile Ala
            580

<210> SEQ ID NO 19
<211> LENGTH: 1582
<212> TYPE: DNA
<213> ORGANISM: Homo sapiens

<400> SEQUENCE: 19
tctagaccat ggaagaccct caaggcgacg ccgctcaaaa aaccgacacc agtcatcacg      60
accaagacca tccgactttt aataaaatta ctccaaattt agccgaattt gcttttctt     120 tgtatagaca attagctcat caaagtaatt ctactaacat ttttttttagt cctgtttcta    180 ttgccactgc tttcgccatg ttgagtttag gtactaaagc cgatacccat gacgagattt    240
tagaaggttt aaactttaat ttgaccgaaa tcccagaagc ccaaattcac gagggttttc    300
aagagttgtt gagaactttg aatcaacctg attctcaatt gcaattaact actggtaacg    360
gtttattttt gtctgaaggt ttaaaattgg ttgacaaatt cctagaagac gtcaagaaac    420
tatatcatag tgaggctttt accgttaatt ttggtgatac tgaggaagct aaaaagcaaa    480
ttaatgatta tgttgagaaa ggcacccagg gtaagatcgt tgacctagtt aaagaattag    540
atcgtgatac cgtcttcgca ctagttaact atatttttttt caagggtaag tgggaacgtc    600
ctttcgaggt taaagatact gaagaggaag attttcatgt tgatcaagtt actactgtca    660
aagttccaat gatgaaaaga ctgggtatgt tcaatattca acattgcaaa aaattaagtt    720
cttgggtctt attaatgaag tatttaggta acgctactgc tatttttttt ttaccagacg    780
aaggtaagct tcaacattta gagaatgagt tgactcatga cattattact aaattttttag    840 agaacgagga tcgtcgtagc gcttctctgc acctgccaaa gttaagtatc accggtactt    900
```

-continued

```
acgacttaaa atctgtttta ggccagttag gtattaccaa agttttttct aacggtgccg      960
atttgagtgg tgttactgaa gaagctccat taaaattgag taaagctgtt cacaaagccg     1020
tcttaactat tgatgaaaag ggtaccgagg ccgccggcgc tatgttcctg gaagctattc     1080
caatgagcat tccaccagaa gttaaattta ataaaccatt cgttttcctg atgatcgagc     1140
agaacactaa aagcccattg tttatgggta aggttgtcaa cccaactcag aagatgtgca     1200
cgtgtgtccc accccaccca cagacggcct tctgcaattc cgacctcgtc atcagggcca     1260
agttcgtggg gacaccagaa gtcaaccaga ccaccttata ccagcgttat gagatcaaga     1320
tgaccaagat gtataaaggg ttccaagcct taggggatgc cgctgacatc cggttcgtct     1380 acaccccgc catggagagt gtctgcggat acttccacag gtcccacaac cgcagcgagg      1440
agtttctcat tgctggaaaa ctgcaggatg gactcttgca catcactacc tgcagtttcg     1500
tggctccctg gaacagcctg agcttagctc agcgccgggg cttcaccaag acctacactg     1560
ttggctgtga ggaatagtcg ac                                              1582
```

<210> SEQ ID NO 20
<211> LENGTH: 522
<212> TYPE: PRT
<213> ORGANISM: Homo sapiens

<400> SEQUENCE: 20

```
Met Glu Asp Pro Gln Gly Asp Ala Ala Gln Lys Thr Asp Thr Ser His
  1               5                  10                  15

His Asp Gln Asp His Pro Thr Phe Asn Lys Ile Thr Pro Asn Leu Ala
                 20                  25                  30

Glu Phe Ala Phe Ser Leu Tyr Arg Gln Leu Ala His Gln Ser Asn Ser
             35                  40                  45

Thr Asn Ile Phe Phe Ser Pro Val Ser Ile Ala Thr Ala Phe Ala Met
         50                  55                  60

Leu Ser Leu Gly Thr Lys Ala Asp Thr His Asp Glu Ile Leu Glu Gly
 65                  70                  75                  80

Leu Asn Phe Asn Leu Thr Glu Ile Pro Glu Ala Gln Ile His Glu Gly
                 85                  90                  95

Phe Gln Glu Leu Leu Arg Thr Leu Asn Gln Pro Asp Ser Gln Leu Gln
            100                 105                 110

Leu Thr Thr Gly Asn Gly Leu Phe Leu Ser Glu Gly Leu Lys Leu Val
        115                 120                 125

Asp Lys Phe Leu Glu Asp Val Lys Lys Leu Tyr His Ser Glu Ala Phe
    130                 135                 140

Thr Val Asn Phe Gly Asp Thr Glu Glu Ala Lys Lys Gln Ile Asn Asp
145                 150                 155                 160

Tyr Val Glu Lys Gly Thr Gln Gly Lys Ile Val Asp Leu Val Lys Glu
                165                 170                 175

Leu Asp Arg Asp Thr Val Phe Ala Leu Val Asn Tyr Ile Phe Phe Lys
            180                 185                 190

Gly Lys Trp Glu Arg Pro Phe Glu Val Lys Asp Thr Glu Glu Glu Asp
        195                 200                 205

Phe His Val Asp Gln Val Thr Thr Val Lys Val Pro Met Met Lys Arg
    210                 215                 220

Leu Gly Met Phe Asn Ile Gln His Cys Lys Lys Leu Ser Ser Trp Val
225                 230                 235                 240

Leu Leu Met Lys Tyr Leu Gly Asn Ala Thr Ala Ile Phe Phe Leu Pro
                245                 250                 255
```

Asp Glu Gly Lys Leu Gln His Leu Glu Asn Glu Leu Thr His Asp Ile
          260                 265                 270

Ile Thr Lys Phe Leu Glu Asn Glu Asp Arg Arg Ser Ala Ser Leu His
      275                 280                 285

Leu Pro Lys Leu Ser Ile Thr Gly Thr Tyr Asp Leu Lys Ser Val Leu
      290                 295                 300

Gly Gln Leu Gly Ile Thr Lys Val Phe Ser Asn Gly Ala Asp Leu Ser
305                 310                 315                 320

Gly Val Thr Glu Glu Ala Pro Leu Lys Leu Ser Lys Ala Val His Lys
              325                 330                 335

Ala Val Leu Thr Ile Asp Glu Lys Gly Thr Glu Ala Ala Gly Ala Met
              340                 345                 350

Phe Leu Glu Ala Ile Pro Met Ser Ile Pro Pro Glu Val Lys Phe Asn
          355                 360                 365

Lys Pro Phe Val Phe Leu Met Ile Glu Gln Asn Thr Lys Ser Pro Leu
      370                 375                 380

Phe Met Gly Lys Val Val Asn Pro Thr Gln Lys Met Cys Thr Cys Val
385                 390                 395                 400

Pro Pro His Pro Gln Thr Ala Phe Cys Asn Ser Asp Leu Val Ile Arg
              405                 410                 415

Ala Lys Phe Val Gly Thr Pro Glu Val Asn Gln Thr Thr Leu Tyr Gln
              420                 425                 430

Arg Tyr Glu Ile Lys Met Thr Lys Met Tyr Lys Gly Phe Gln Ala Leu
          435                 440                 445

Gly Asp Ala Ala Asp Ile Arg Phe Val Tyr Thr Pro Ala Met Glu Ser
450                 455                 460

Val Cys Gly Tyr Phe His Arg Ser His Asn Arg Ser Glu Glu Phe Leu
465                 470                 475                 480

Ile Ala Gly Lys Leu Gln Asp Gly Leu Leu His Ile Thr Thr Cys Ser
              485                 490                 495

Phe Val Ala Pro Trp Asn Ser Leu Ser Leu Ala Gln Arg Arg Gly Phe
          500                 505                 510

Thr Lys Thr Tyr Thr Val Gly Cys Glu Glu
      515                 520

<210> SEQ ID NO 21
<211> LENGTH: 397
<212> TYPE: DNA
<213> ORGANISM: Homo sapiens

<400> SEQUENCE: 21
tctagaccat gtgcacctgt gtcccacccc acccacagac ggccttctgc aattccgacc    60
tcgtcatcag ggccaagttc gtggggacac cagaagtcaa ccagaccacc ttataccagc   120
gttatgagat caagatgacc aagatgtata aagggttcca agcctaggg gatgccgctg    180 acatccggtt cgtctacacc cccgccatgg agagtgtctg cggatacttc cacaggtccc   240
acaaccgcag cgaggagttt ctcattgctg gaaaactgca ggatggactc ttgcacatca   300
ctacctgcag tttcgtggct ccctggaaca gcctgagctt agctcagcgc cggggcttca   360
ccaagacgta tactgttggc tgtgaggaat agtcgac                            397

<210> SEQ ID NO 22
<211> LENGTH: 127
<212> TYPE: PRT
<213> ORGANISM: Homo sapiens -continued

<400> SEQUENCE: 22

| Met | Cys | Thr | Cys | Val | Pro | Pro | His | Pro | Gln | Thr | Ala | Phe | Cys | Asn | Ser |
| 1 | | | | 5 | | | | | 10 | | | | | 15 | |

| Asp | Leu | Val | Ile | Arg | Ala | Lys | Phe | Val | Gly | Thr | Pro | Glu | Val | Asn | Gln |
| | | | 20 | | | | | 25 | | | | | 30 | | |

| Thr | Thr | Leu | Tyr | Gln | Arg | Tyr | Glu | Ile | Lys | Met | Thr | Lys | Met | Tyr | Lys |
| | | | 35 | | | | | 40 | | | | 45 | | | |

| Gly | Phe | Gln | Ala | Leu | Gly | Asp | Ala | Ala | Asp | Ile | Arg | Phe | Val | Tyr | Thr |
| | | 50 | | | | | 55 | | | | 60 | | | | |

| Pro | Ala | Met | Glu | Ser | Val | Cys | Gly | Tyr | Phe | His | Arg | Ser | His | Asn | Arg |
| 65 | | | | | 70 | | | | | 75 | | | | | 80 |

| Ser | Glu | Glu | Phe | Leu | Ile | Ala | Gly | Lys | Leu | Gln | Asp | Gly | Leu | Leu | His |
| | | | | 85 | | | | | 90 | | | | | 95 | |

| Ile | Thr | Thr | Cys | Ser | Phe | Val | Ala | Pro | Trp | Asn | Ser | Leu | Ser | Leu | Ala |
| | | | 100 | | | | | 105 | | | | | 110 | | |

| Gln | Arg | Arg | Gly | Phe | Thr | Lys | Thr | Tyr | Thr | Val | Gly | Cys | Glu | Glu |
| | | 115 | | | | | 120 | | | | | 125 | | |

<210> SEQ ID NO 23
<211> LENGTH: 400
<212> TYPE: DNA
<213> ORGANISM: Homo sapiens

<400> SEQUENCE: 23

```
tctagaccat gtgcacctgt gtcccacccc acccacagac ggccttctgc aattccgacc     60
tcgtcatcag ggccaagttc gtggggacac cagaagtcaa ccagaccacc ttataccagc    120
gttatgagat caagatgacc aagatgtata aagggttcca agcctaggg gatgccgctg     180
acatccggtt cgtctacacc cccgccatgg agagtgtctg cggatacttc acaggtccc    240
acaaccgcag cgaggagttt ctcattgctg gaaaactgca ggatggactc ttgcacatca    300
ctacctgcag tttcgtggct ccctggaaca gcctgagctt agctcagcgc cggggcttca    360
ccaagacgta tactgttggc tgtgaggaat gctagtcgac                           400
```

<210> SEQ ID NO 24
<211> LENGTH: 128
<212> TYPE: PRT
<213> ORGANISM: Homo sapiens

<400> SEQUENCE: 24

| Met | Cys | Thr | Cys | Val | Pro | Pro | His | Pro | Gln | Thr | Ala | Phe | Cys | Asn | Ser |
| 1 | | | | 5 | | | | | 10 | | | | | 15 | |

| Asp | Leu | Val | Ile | Arg | Ala | Lys | Phe | Val | Gly | Thr | Pro | Glu | Val | Asn | Gln |
| | | | 20 | | | | | 25 | | | | | 30 | | |

| Thr | Thr | Leu | Tyr | Gln | Arg | Tyr | Glu | Ile | Lys | Met | Thr | Lys | Met | Tyr | Lys |
| | | | 35 | | | | | 40 | | | | 45 | | | |

| Gly | Phe | Gln | Ala | Leu | Gly | Asp | Ala | Ala | Asp | Ile | Arg | Phe | Val | Tyr | Thr |
| | | 50 | | | | | 55 | | | | 60 | | | | |

| Pro | Ala | Met | Glu | Ser | Val | Cys | Gly | Tyr | Phe | His | Arg | Ser | His | Asn | Arg |
| 65 | | | | | 70 | | | | | 75 | | | | | 80 |

| Ser | Glu | Glu | Phe | Leu | Ile | Ala | Gly | Lys | Leu | Gln | Asp | Gly | Leu | Leu | His |
| | | | | 85 | | | | | 90 | | | | | 95 | |

| Ile | Thr | Thr | Cys | Ser | Phe | Val | Ala | Pro | Trp | Asn | Ser | Leu | Ser | Leu | Ala |
| | | | 100 | | | | | 105 | | | | | 110 | | |

| Gln | Arg | Arg | Gly | Phe | Thr | Lys | Thr | Tyr | Thr | Val | Gly | Cys | Glu | Glu | Cys |

```
              115                 120                 125

<210> SEQ ID NO 25
<211> LENGTH: 72
<212> TYPE: DNA
<213> ORGANISM: Homo sapiens

<400> SEQUENCE: 25
atgccgtctt ctgtctcgtg gggcatcctc ctgctggcag gcctgtgctg cctggtccct     60
gtctccctgg ct                                                        72

<210> SEQ ID NO 26
<211> LENGTH: 24
<212> TYPE: PRT
<213> ORGANISM: Homo sapiens

<400> SEQUENCE: 26

Met Pro Ser Ser Val Ser Trp Gly Ile Leu Leu Leu Ala Gly Leu Cys
 1               5                  10                  15

Cys Leu Val Pro Val Ser Leu Ala
            20

<210> SEQ ID NO 27
<211> LENGTH: 75
<212> TYPE: DNA
<213> ORGANISM: Homo sapiens

<400> SEQUENCE: 27
atgaagtcca gcggcctctt ccccttcctg gtgctgcttg ccctgggaac tctggcacct     60
tgggctgtgg aaggc                                                     75

<210> SEQ ID NO 28
<211> LENGTH: 25
<212> TYPE: PRT
<213> ORGANISM: Homo sapiens

<400> SEQUENCE: 28

Met Lys Ser Ser Gly Leu Phe Pro Phe Leu Val Leu Leu Ala Leu Gly
 1               5                  10                  15

Thr Leu Ala Pro Trp Ala Val Glu Gly
            20                  25

<210> SEQ ID NO 29
<211> LENGTH: 69
<212> TYPE: DNA
<213> ORGANISM: Homo sapiens

<400> SEQUENCE: 29
atggccccct ttgagcccct ggcttctggc atcctgttgt tgctgtggct gatagccccc     60
agcagggcc                                                            69

<210> SEQ ID NO 30
<211> LENGTH: 23
<212> TYPE: PRT
<213> ORGANISM: Homo sapiens

<400> SEQUENCE: 30

Met Ala Pro Phe Glu Pro Leu Ala Ser Gly Ile Leu Leu Leu Leu Trp
 1               5                  10                  15

Leu Ile Ala Pro Ser Arg Ala
            20
```

```
<210> SEQ ID NO 31
<211> LENGTH: 269
<212> TYPE: DNA
<213> ORGANISM: Homo sapiens

<400> SEQUENCE: 31
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240 tctctagata aaagagaggc tgaagcttg                                        269

<210> SEQ ID NO 32
<211> LENGTH: 89
<212> TYPE: PRT
<213> ORGANISM: Homo sapiens

<400> SEQUENCE: 32

Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Asp Lys Arg Glu Ala Glu Ala
                 85

<210> SEQ ID NO 33
<211> LENGTH: 4
<212> TYPE: PRT
<213> ORGANISM: Artificial sequence
<220> FEATURE:
<223> OTHER INFORMATION: Synthetic construct

<400> SEQUENCE: 33

Ala Ala Pro Val
  1
```

MULTIFUNCTIONAL PROTEASE INHIBITORS AND THEIR USE IN TREATMENT OF DISEASE

CROSS-REFERENCE TO RELATED APPLICATIONS

This application claims the benefit of the provisional patent application U.S. Ser. No. 60/256,699, filed Dec. 18, 2000, and provisional patent application Ser. No. 60/331, 966, filed Nov. 20, 2001 which are in addition hereby incorporated by reference in their entirety.

TECHNICAL FIELD

This invention relates to fusion proteins of protease inhibitors, and to methods of making and using these fusion proteins, pharmaceutical compositions and kits comprising these fusion proteins, and to polynucleotides encoding these fusion proteins.

BACKGROUND OF THE INVENTION

Protease/protease inhibitor imbalances are a common feature of chronic diseases of humans. Examples of diseases and pathological conditions in which an imbalance of proteases and their inhibitors is implicated include rheumatoid and other forms of arthritis, tumor metastasis, tumor angiogenesis, periodontal disease, corneal, epidermal, and gastric ulceration, osteoporosis, Paget's disease of bone, glomerulonephritis, atopic dermatitis, psoriasis, scleroderma, pressure atrophy of bone or tissues, cholesteatoma, nerve cell disorders, organ injury due to ischemia-reperfusion (including local sequelae of myocardial anoxia), malaria, chronic wound healing, Chagas disease, parasitic eye infection, viral infection (e.g. HIV, herpes), bacterial infection, Alzheimer's disease, hypertension, sepsis, acute leukemia, dystrophic epidermolysis bullosa, and muscular dystrophy.

In particular, protease/protease inhibitor imbalances are notable in a number of respiratory diseases. The classic and prototypic example of this is alpha 1-antitrypsin (AAT) deficiency, where low levels of AAT (also known as alpha 1-protease inhibitor) in the bloodstream, determined by genetic factors, lead to decreased levels of AAT in the lung. The consequence of this is a decreased inhibitory capacity towards the proteolytic enzyme neutrophil elastase. This compromised ability to control elastolytic activity, and the consequent degradation of lung elastin, leads inevitably to the early onset of pulmonary emphysema in many individuals with AAT-deficiency.

Other respiratory diseases where protease/protease inhibitor imbalances have been shown to have significant involvement in disease progression are asthma, chronic obstructive pulmonary disease (COPD), cystic fibrosis (CF), and respiratory distress syndrome. In asthma, the mast cell-derived proteases, tryptase and chymase, have been shown to be involved in the inflammatory response to allergenic stimuli. Similarly, the inhibition of airway hyperresponsiveness by AAT has implicated protease targets for AAT, such as neutrophil elastase, cathepsin G, and kallikrein as possible contributory factors in this condition.

Elevated levels of several matrix metalloproteases (MMPs) have been shown in human COPD, particularly in COPD induced by cigarette smoking. Although implicated in the degradation of lung collagen and elastin, the relative contributions of metalloproteases and elastase to the reduction of lung elasticity, and consequent development of pulmonary emphysema is not fully understood at the present time. Interestingly, transgenic mouse models for smoking-related emphysema have implicated the murine metalloelastase (equivalent to human MMP-12) as a critical factor in the development of smoking related COPD in this species.

Protease inhibitors are also implicated in the treatment of HIV. One of the major proteins coded for by HIV nucleic acid is a protease, and one of the most effective treatments of HIV to date is the use of protease inhibitors.

A full understanding of the equilibrium between the above proteases and their inhibitors is made even more complex by the findings that matrix metalloprotease inhibitors are capable of cleaving, and thereby inactivating AAT and, conversely, neutrophil elastase can inactivate endogenous tissue inhibitors of metalloproteases (TIMPs). A major pathogen of the lung, *Pseudomonas aeruginosa*, which colonizes the lungs of many individuals with CF, secretes a metalloelastase that degrades AAT, leading to much of the lung damage associated with CF.

The incidence of many diseases in which a protease/protease inhibitor imbalance is implicated is increasing; for example, the incidence of emphysema in the U.S. is up over 40% compared to 1982. While there have been advancements in the amelioration of these diseases, there are at present no completely satisfactory treatments. Hence there is a need for improved methods of treatment to reduce symptoms and/or to slow or halt disease progress. The present invention addresses these needs.

SUMMARY OF THE INVENTION

This invention provides fusion proteins of protease inhibitors, or functionally active portions of protease inhibitors, such as fusion proteins comprising alpha 1-antitrypsin (AAT) and a second protease inhibitor. In some embodiments the invention provides fusion proteins comprising AAT and secretory leukocyte protease inhibitor (SLPI), or AAT and a tissue inhibitor of metalloproteases (TIMP), as well as methods of making and using these fusion proteins. Such fusion proteins have the advantage that they provide a broad spectrum of protease inhibition in a single entity, which is useful in conditions where more than one protease is present, such as in many of the pathological conditions described above, and in tissue preparation, extraction, analysis, and other procedures where control of unwanted protease activity is desirable.

In one aspect, the invention features a fusion protein comprising AAT (including functionally active portions thereof) and another protease inhibitor (including functionally active portions thereof), polynucleotides encoding the fusion protein, vectors and host cells containing the polynucleotides, methods of producing the fusion protein, and pharmaceutical compositions that contain the fusion protein. In one aspect, the second protease inhibitor is a serine protease inhibitor, in another aspect the second protease inhibitor is a tissue inhibitor of metalloproteases, in a further aspect the second protease inhibitor is an inhibitor of cysteinyl proteases, and in still a further embodiment, the second protease inhibitor is an inhibitor of aspartyl proteases.

In another aspect, the invention features a fusion protein comprising AAT, or a functionally active portion thereof, fused to SLPI, or a functionally active portion thereof. Related to this aspect, the invention includes polynucleotides encoding a fusion protein of AAT and SLPI, or functionally active portions thereof, vectors and host cells containing such polynucleotides, methods of producing such fusion proteins, and pharmaceutical compositions containing such fusion proteins.

In yet another aspect, the invention features a fusion protein comprising AAT, or functionally active portion thereof, and TIMP, or a functionally active portion thereof. An embodiment of this aspect includes fusion proteins in which the TIMP portion is TIMP-1, or a functionally active portion thereof. Related to this aspect, the invention includes polynucleotides encoding such fusion proteins of AAT and TIMP, or functionally active portions thereof, vectors and host cells containing these polynucleotides, methods of producing the fusion proteins, and pharmaceutical compositions containing the fusion proteins.

In a further aspect, the invention features a fusion protein comprising amino acids from about 1 to about 394 of AAT, and amino acids from about 1 to about 107 of SLPI. In one embodiment of this aspect of the invention, the carboxy terminus of amino acids from about 1 to about 394 of AAT is joined to the amino terminus of amino acids from about 1 to about 107 of SLPI (i.e., the fusion protein comprises, from its amino to its carboxy termini, amino acids from about 1 to about 394 of AAT fused to amino acids from about 1 to about 107 of SLPI). In another embodiment the carboxy terminus of amino acids from about 1 to about 107 of SLPI is joined to the amino terminus of amino acids from about 1 to about 394 of AAT (i.e., the fusion protein comprises, from its amino to its carboxy termini, amino acids from about 1 to about 107 of SLPI fused to amino acids from about 1 to about 394 of AAT). In a related aspect, the invention features the polynucleotides that encode the above fusion proteins. Also included are vectors and host cells containing the polynucleotides that encode the fusion proteins, methods of producing the fusion proteins, and pharmaceutical compositions that contain the fusion proteins.

In a further aspect, the invention features a fusion protein comprising amino acids from about 1 to about 394 of alpha 1-antitrypsin; and amino acids from about 1 to about 184 of tissue inhibitor of metalloproteases-1. In one embodiment of this aspect of the invention, the carboxy terminus of amino acids from about 1 to about 394 of AAT is joined to the amino terminus of amino acids from about 1 to about 184 of tissue inhibitor of metalloproteases-1 (i.e., the fusion protein comprises, from its amino to its carboxy termini, amino acids from about 1 to about 394 of AAT fused to amino acids from about 1 to about 184 of tissue inhibitor of metalloproteases-1). In another embodiment the carboxy terminus of amino acids from about 1 to about 184 of tissue inhibitor of metalloproteases-1 is joined to the amino terminus of amino acids from about 1 to about 394 of AAT (i.e., the fusion protein comprises, from its amino to its carboxy termini, amino acids from about 1 to about 184 of tissue inhibitor of metalloproteases-1 fused to amino acids from about 1 to about 394 of AAT). In a related aspect, the invention features the polynucleotides that encode the above fusion proteins. Also included are vectors and host cells containing the polynucleotides that encode the fusion proteins, methods of producing the fusion proteins, and pharmaceutical compositions that contain the fusion proteins.

In yet a further aspect, the invention features a fusion protein comprising amino acids from about 1 to about 394 of alpha 1-antitrypsin; and amino acids from about 1 to about 126 of tissue inhibitor of metalloproteases-1. In one embodiment of this aspect of the invention, the carboxy terminus of amino acids from about 1 to about 394 of AAT is joined to the amino terminus of amino acids from about 1 to about 126 of tissue inhibitor of metalloproteases-1 (i.e., the fusion protein comprises, from its amino to its carboxy termini, amino acids from about 1 to about 394 of AAT fused to amino acids from about 1 to about 126 of tissue inhibitor of metalloproteases-1). In another embodiment the carboxy terminus of amino acids from about 1 to about 126 of tissue inhibitor of metalloproteases-1 is joined to the amino terminus of amino acids from about 1 to about 394 of AAT (i.e., the fusion protein comprises, from its amino to its carboxy termini, amino acids from about 1 to about 126 of tissue inhibitor of metalloproteases-1 fused to amino acids from about 1 to about 394 of AAT). In a related aspect, the invention features the polynucleotides that encode the above fusion proteins. Also included are vectors and host cells containing the polynucleotides that encode the fusion proteins, methods of producing the fusion proteins, and pharmaceutical compositions that contain the fusion proteins.

In still yet a further aspect, the invention features a fusion protein comprising amino acids from about 1 to about 394 of alpha 1-antitrypsin; and amino acids from about 1 to about 127 of tissue inhibitor of metalloproteases-1, wherein the alpha 1-antitrypsin polypeptide is covalently linked to the tissue inhibitor of metalloproteases-1 polypeptide through a disulfide bond between amino acid 127 of the tissue inhibitor of metalloproteases-1 polypeptide and a free cysteine residue of the alpha 1-antitrypsin polypeptide. In one embodiment of this aspect of the invention, the free cysteine residue of the alpha 1-antitrypsin polypeptide is at position 232 in SEQ ID NO: 2.

Also within the invention are methods of using the protease inhibitor fusion proteins of the invention, including for inhibition of protease activity in vitro (e.g., in a biological sample) or in vivo (e.g., in treating diseases and conditions where the disease or condition is associated with a protease/protease inhibitor imbalance and/or an inflammatory response involving protease activity). One embodiment of this aspect of the invention includes a method for inhibiting protease activity by contacting the protease with one of the fusion proteins of the invention. In a further embodiment, the protease activity is associated with a disorder selected from the group consisting of emphysema, asthma, chronic obstructive pulmonary disease, cystic fibrosis, otitis media, and otitis externa. In yet a further embodiment, the protease activity is associated with HIV infection. In one embodiment, the fusion protein is contacted with the protease by administering the fusion protein to an individual having the protease.

Another aspect of the methods of the invention is a method of treating an individual suffering from, or at risk for, a disease or disorder involving unwanted protease activity comprising administering to the individual an effective amount of a fusion protein of the invention. In one embodiment of this aspect, the individual suffers from emphysema. In another embodiment of this aspect of the invention, the individual suffers from asthma. In yet another embodiment of this aspect of the invention, the individual suffers from chronic obstructive pulmonary disease. In still yet another embodiment of this aspect of the invention, the individual suffers from cystic fibrosis. In still yet further another embodiment of this aspect of the invention, the individual suffers from otitis media or otitis externa.

Another aspect of the invention provides compositions and kits comprising the fusion proteins of the invention. In one embodiment of this aspect of the invention, the kits further comprise instructions for use of the fusion protein.

DETAILED DESCRIPTION OF THE INVENTION

Figure 1:
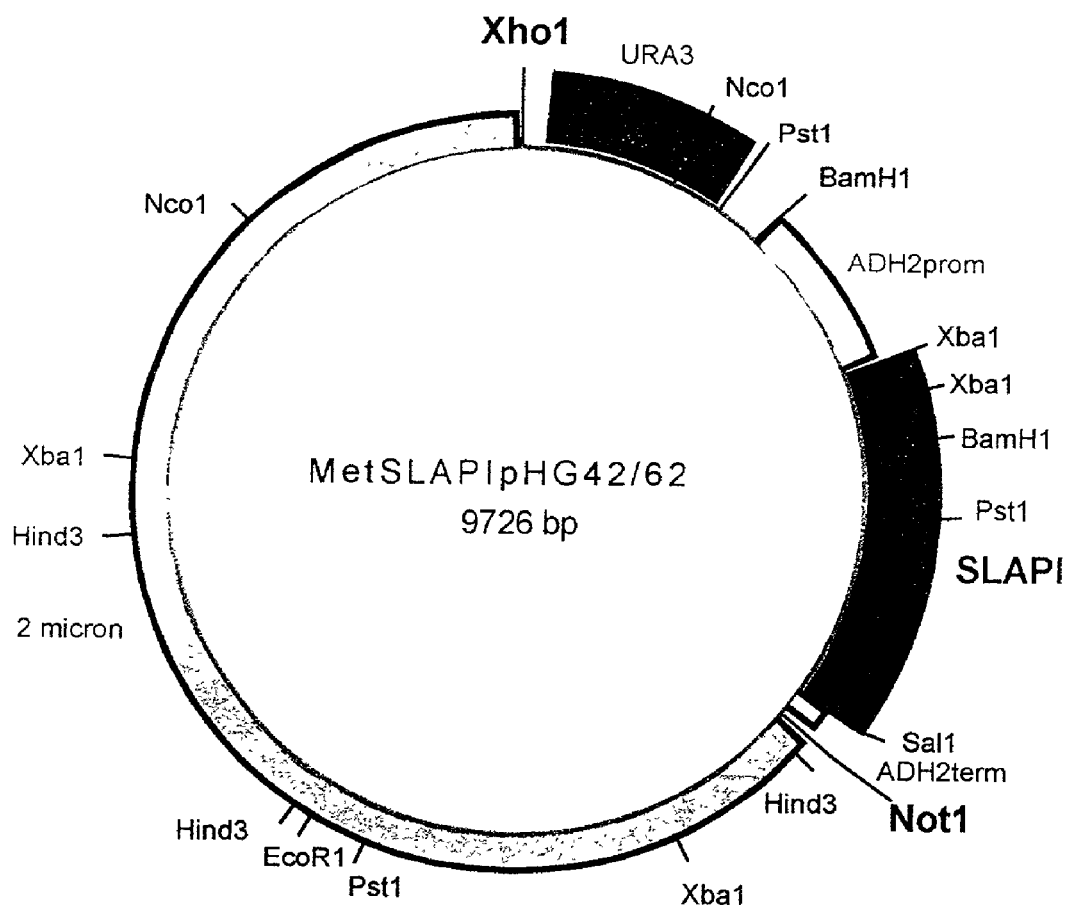
FIG. 1 is a schematic diagram of a yeast expression vector, pHG62, used to produce a SLPI/AAT fusion protein in the yeast *Saccharomyces cerevisiae*. The resulting expressed protein is designated SLAPI.

The present invention relates to fusion proteins of alpha 1-antitrypsin (AAT) and another protease inhibitor protein, and to methods of making and using such fusion proteins to inhibit proteases. The second protease inhibitor of the fusion proteins of the invention may be an inhibitor of serine proteases, an inhibitor of metalloproteases, an inhibitor of cysteine proteases, or an inhibitor of aspartate proteases. In one embodiment, the second protease inhibitor is secretory leukocyte protease inhibitor (SLPI). In another embodiment, the second protease inhibitor is a tissue inhibitor of metalloproteases (TIMP), preferably TIMP-1. The invention also includes the polynucleotides encoding these constructs, the vectors comprising the polynucleotides and host cells comprising the polynucleotides, as well as methods of producing the fusion proteins. The invention also includes methods of using the fusion proteins to inhibit proteases. The proteases may be present in vitro or they may be in an individual with a pathology.

I. Definitions

As used herein, a "polynucleotide" is a polymeric form of nucleotides of any length, which contain deoxyribonucleotides, ribonucleotides, and/or their analogs. The terms "polynucleotide" and "nucleotide" as used herein are used interchangeably. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudoruacil, 5-pentynyluracil and 2,6-diaminopurine. The use of uracil as a substitute for thymine in a deoxyribonucleic acid is also considered an analogous form of pyrimidine.

If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).

Further, any of the hydroxyl groups ordinarily present in the sugars may be replaced by phosphonate groups, phosphate groups, protected by standard protecting groups, or activated to prepare additional linkages to additional nucleotides, or may be conjugated to solid supports. The 5' and 3' terminal OH groups can be phosphorylated or substituted with amines or organic capping groups moieties of from 1 to 20 carbon atoms. Other hydroxyls may also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

As noted above, one or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1–20 C) optionally containing and ether (—O—) linkage, aryl, alkenyl, cycloalky, cycloalkenyl or araldyl. Not all linkages in a polynucleotide need be identical.

Although conventional sugars and bases will be used in applying the method of the invention, substitution of analogous forms of sugars, purines and pyrimidines can be advantageous in designing a final product, as can alternative backbone structures like a polyamide backbone.

The term "recombinant" polynucleotide (and by analogy, a "recombinant" polypeptide" produced by the expression of a recombinant polynucleotide) is one which is not naturally occurring or is made by the artificial combination of two otherwise separated segments of sequence by chemical synthesis means or the artificial manipulation of isolated segments of polynucleotides, e.g., by genetic engineering techniques. Thus, the term "recombinant" polynucleotide as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, carboxylation, phosphorylation, ubiquitination, pegylation or any other manipulation or modification, such as conjugation with a labeling component. Also included within the definition are, for example, polypeptides containing one or more analogs of an amino acid (including, for example, unnatural amino acids, etc.), as well as other modifications. Such modifications are well known; see, e.g., Molecular Cloning: A Laboratory Manual, 2nd ed., Vol. 1–3, ed. Sambrook, et al., Cold Spring Harbor Laboratory Press (1989) or Current Protocols in Molecular Biology, ed. F. Ausubel et al., Greene Publishing and Wiley-Interscience: New York (1987 and periodic updates).

A polynucleotide is said to "encode" a polypeptide if, in its native state or when manipulated by methods well known to those skilled in the art, it can be transcribed and/or translated to produce the polypeptide.

A "fusion protein" is a single polypeptide comprising regions from two or more different proteins. The regions normally exist in or as separate proteins and are brought together in the fusion protein. They may be linked together so that the amino acid sequence of one begins where the amino acid sequence of the other ends, or they may be linked via linker amino acids which are not normally a part of the constituent proteins. They may be linked in any manner, such as through amide bonds, disulfide bonds, etc. A fusion protein may contain more than one copy of any of its constituent proteins or regions. The constituent proteins or regions may include the entire amino acid sequences of the proteins or portions of the amino acid sequences. As is apparent from the definition of "protein," above, the protein may be in branched form; e.g., the side chain of one amino acid in one chain may be linked to the side chain of another, terminal amino acid in another chain by any of a variety of methods known to those of skill in the art (for example, disulfide bond formation). Alternatively, non-terminal amino acids of different chains may also be linked by intermolecular bonds between side chains (e.g., disulfide bonds) to form a branched protein.

A "cell line" or "cell culture" denotes cells grown or maintained in vitro. It is understood that the descendants of a cell may not be completely identical (either morphologically, genotypically, or phenotypically) to the parent cell.

As used herein, the term "vector" refers to a polynucleotide molecule capable of transporting another polynucleotide to which it has been linked and can include a plasmid, cosmid or viral vector. The term includes vectors that function primarily for insertion of a polynucleotide molecule into a cell, replication vectors that function primarily for the replication of polynucleotide, and expression vectors that function for transcription and/or translation of the DNA or RNA. Also included are vectors that provide more than one of the above functions. The vector can be capable of autonomous replication or it can integrate into a host DNA. Viral vectors include, e.g., replication defective retroviruses, adenoviruses and adeno-associated viruses.

A vector can include nucleic acid coding for the fusion protein of the invention in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein.

The recombinant expression vectors of the invention can be designed for expression of the fusion proteins of the invention in prokaryotic or eukaryotic cells. For example, polypeptides of the invention can be expressed in *E. coli*, insect cells (e.g., using baculovirus expression vectors), yeast cells, mammalian cells in culture, or in transgenic animals. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

A way to maximize recombinant protein expression in *E. coli* is to express the protein in host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The fusion protein expression vector can also be a yeast expression vector, examples of which are described herein, a vector for expression in insect cells, e.g., a baculovirus expression vector or a vector suitable for expression in mammalian cells in culture, or in transgenic animals. Methods of expressing proteins in yeast, such as *Saccharomyces cerevisiae, Pichia pastoris, Hansenula polymorpha*, and *Kluyveromyces lactis*, are well-known in the art.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

A "host cell" includes an individual cell or cell culture which can be or has been a recipient for vector(s) or for incorporation of polynucleotide molecules and/or proteins. A host cell can be any prokaryotic or eukaryotic cell. For example, fusion proteins of the invention can be expressed in bacterial cells such as *E. coli*, insect cells, yeast or mammalian cells (such as Chinese hamster ovary cells (CHO) or COS cells). Other suitable host cells are known to those skilled in the art. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A "signal sequence," also known as a "leader sequence," is a short amino acid sequence that directs newly synthesized secretory or membrane proteins to and through cellular membranes such as the endoplasmic reticulim. Signal sequences are typically in the N-terminal portion of a polypeptide and are cleaved after the polypeptide has crossed the membrane.

As used herein, "treatment" is an approach for obtaining beneficial or desired results, including clinical results. For purposes of this invention, beneficial or desired clinical results include, but are not limited to, alleviation of one or more symptoms, diminishment of extent of disease, stabilized (i.e., not worsening) state of disease, preventing spread (i.e., metastasis) of disease, preventing occurrence or recurrence of disease, delay or slowing of disease progression, amelioration or palliation of the disease state, and remission (whether partial or total), whether detectable or undetectable. "Treatment" can also mean prolonging survival as compared with expected survival if not receiving treatment.

An "effective amount" is an amount sufficient to effect beneficial or desired clinical results. An effective amount can be administered in one or more administrations. In terms of treatment, an "effective amount" of a fusion protein of the invention is an amount that is sufficient to palliate, ameliorate, stabilize, reverse or slow the progression of a protease-associated disease state. An "effective amount" may be of a fusion protein used alone or in conjunction with one or more agents used to treat a disease or disorder.

An "individual" is a vertebrate, preferably a mammal, more preferably a human. Mammals include, but are not limited to, farm animals, sport animals, primates, and pets.

"A," "an," and "the" include one or more.

"Comprising" means "including"

II. Fusion Proteins and their Construction

The practice of the present invention will employ, unless otherwise indicated, conventional techniques of molecular biology (including recombinant DNA techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al, eds., 1994); "Current Protocols in Immunology" (J. E. Coligan et al., eds., 1991).

These techniques are applicable to the production of the polynucleotides and polypeptides of the invention, and, as such, are to be considered when contemplating these inventive aspects. Particularly useful systems for individual aspects will be discussed below.

Fusion proteins of the invention are generally referred to by reference to the active components, e.g., a fusion protein of AAT and SLPI. It is understood that these references refer to various embodiments, such as fusion proteins comprising functionally active portions, etc.

Protein and nucleotides The compositions of the present invention include fusion proteins and the polynucleotides which code for these fusion proteins. The fusion proteins comprise AAT or a functionally active portion thereof and another protease inhibitor or a functionally active portion thereof.

A DNA sequence encoding human AAT (Table 1) and the amino acid sequence of human AAT (Table 2) are listed as SEQ ID NOS: 1 and 2, respectively. Functionally active portions of AAT and other protease inhibitors are known in the art and may be used in the fusion proteins of the invention. Further, assays for assessing activity of functionally active portions (whether alone or in the context of a larger sequence) are known. Human AAT is the preferred form for the invention, and the native amino acid sequence is the most preferred form. However, sequences from other species may be used.

TABLE 1

DNA sequence encoding human AAT

```
gaagaccctc aaggcgacgc cgctcaaaaa accgacacca   60
                     gtcatcacga ccaagaccat
ccgactttta ataaaattac tccaaattta gccgaatttg  120
                     cttttctttt gtatagacaa
ttagctcatc aaagtaattc tactaacatt ttttttagtc  180
                     ctgtttctat tgccactgct
ttcgccatgt tgagtttagg tactaaagcc gatacccatg  240
                     acgagatttt agaaggttta
aactttaatt tgaccgaaat cccagaagcc caaattcacg  300
                     agggttttca agagttgttg
agaactttga atcaacctga ttctcaattg caattaacta  360
                     ctggtaacgg tttatttttg
tctgaaggtt taaaattggt tgacaaattc ctagaagacg  420
                     tcaagaaact atatcatagt
gaggctttta ccgttaattt tggtgatact gaggaagcta  480
                     aaaagcaaat taatgattat
gttgagaaag gcacccaggg taagatcgtt gacctagtta  540
                     aagaattaga tcgtgatacc
gtcttcgcac tagttaacta tatttttttc aagggtaagt  600
                     gggaacgtcc tttcgaggtt
aaagatactg aagaggaaga ttttcatgtt gatcaagtta  660
                     ctactgtcaa agttccaatg
atgaaaagac tgggtatgtt caatattcaa cattgcaaaa  720
                     aattaagttc ttgggtctta
ttaatgaagt atttaggtaa cgctactgct atttttttt   780
                     taccagacga aggtaagctt
caacatttag agaatgagtt gactcatgac attattacta  840
                     aattttttaga gaacgaggat
cgtcgtagcg cttctctgca cctgccaaag ttaagtatca  900
                     ccggtactta cgacttaaaa
tctgttttag gccagttagg tattaccaaa gttttttcta  960
                     acggtgccga tttgagtggt
gttactgaag aagctccatt aaaattgagt aaagctgttc 1020
                     acaaagccgt cttaactatt
gatgaaaagg gtaccgaggc cgccggcgct atgttcctgg 1080
                     aagctattcc aatgagcatt
ccaccagaag ttaaatttaa taaaccattc gttttttctga 1140
                     tgatcgagca gaacactaaa
agcccattgt ttatgggtaa ggttgtcaac ccaactcaga 1182
                                           ag
```

TABLE 2

Amino acid sequence of human AAT

```
Glu Asp Pro Gln Gly Asp Ala Ala Gln Lys Thr Asp
 1              5                   10
Thr Ser His His Asp Gln Asp His Pro Thr Phe Asn
          15                  20
```

TABLE 2-continued

Amino acid sequence of human AAT

```
Lys Ile Thr Pro Asn Leu Ala Glu Phe Ala Phe Ser
 25              30                  35
Leu Tyr Arg Gln Leu Ala His Gln Ser Asn Ser Thr
             40                  45
Asn Ile Phe Phe Ser Pro Val Ser Ile Ala Thr Ala
 50              55                          60
Phe Ala Met Leu Ser Leu Gly Thr Lys Ala Asp Thr
                 65                  70
His Asp Glu Ile Leu Glu Gly Leu Asn Phe Asn Leu
         75                  80
Thr Glu Ile Pro Glu Ala Gln Ile His Glu Gly Phe
 85              90                          95
Gln Glu Leu Leu Arg Thr Leu Asn Gln Pro Asp Ser
             100                 105
Gln Leu Gln Leu Thr Thr Gly Asn Gly Leu Phe Leu
         110                 115                 120
Ser Glu Gly Leu Lys Leu Val Asp Lys Phe Leu Glu
                 125                 130
Asp Val Lys Lys Leu Tyr His Ser Glu Ala Phe Thr
             135                 140
Val Asn Phe Gly Asp Thr Glu Glu Ala Lys Lys Gln
 145             150                 155
Ile Asn Asp Tyr Val Glu Lys Gly Thr Gln Gly Lys
                 160                 165
Ile Val Asp Leu Val Lys Glu Leu Asp Arg Asp Thr
 170                 175                     180
Val Phe Ala Leu Val Asn Tyr Ile Phe Phe Lys Gly
                 185                 190
Lys Trp Glu Arg Pro Phe Glu Val Lys Asp Thr Glu
             195                 200
Glu Glu Asp Phe His Val Asp Gln Val Thr Thr Val
 205                 210                     215
Lys Val Pro Met Met Lys Arg Leu Gly Met Phe Asn
                 220                 225
Ile Gln His Cys Lys Lys Leu Ser Ser Trp Val Leu
         230                 235                 240
Leu Met Lys Tyr Leu Gly Asn Ala Thr Ala Ile Phe
                 245                 250
Phe Leu Pro Asp Glu Gly Lys Leu Gln His Leu Glu
                 255                 260
Asn Glu Leu Thr His Asp Ile Ile Thr Lys Phe Leu
 265                 270                     275
Glu Asn Glu Asp Arg Arg Ser Ala Ser Leu His Leu
                 280                 285
Pro Lys Leu Ser Ile Thr Gly Thr Tyr Asp Leu Lys
 290                 295                     300
Ser Val Leu Gly Gln Leu Gly Ile Thr Lys Val Phe
                 305                 310
Ser Asn Gly Ala Asp Leu Ser Gly Val Thr Glu Glu
                 315                 320
```

TABLE 2-continued

Amino acid sequence of human AAT

Ala Pro Leu Lys Leu Ser Lys Ala Val His Lys Ala
325                     330                     335

Val Leu Thr Ile Asp Glu Lys Gly Thr Glu Ala Ala
            340                 345

Gly Ala Met Phe Leu Glu Ala Ile Pro Met Ser Ile
350                 355                     360

Pro Pro Glu Val Lys Phe Asn Lys Pro Phe Val Phe
                365             370

Leu Met Ile Glu Gln Asn Thr Lys Ser Pro Leu Phe
            375             380

Met Gly Lys Val Val Asn Pro Thr Gln Lys
385                 390

Many protease inhibitors besides AAT have been described in the art, and any protease inhibitor (or functionally active portion) for which the amino acid sequence is known may be used as the partner to AAT in the invention. (See, e.g., Aviles, F., ed, Innovations in proteases and their inhibitors, W.deGruyter, Berlin, N.Y., 1993; Barrett, A. J., and Salvesen, G, eds, Proteinase Inhibitors, Elsevier, Amsterdam, 1986; Bode, W., and Huber, R., Natural protein proteinase inhibitors and their interaction with proteinases, Eur. J. Biochem. 204:433–451, 1992; Bode, W., and Huber, R., Proteinase-protein inhibitor interactions, Fibrinolysis 8, Suppl. 1: 161–171, 1994, all of which are incorporated herein by reference).

It will be readily understood by those of skill in the art that the native sequence is not necessarily required for a protein to be functionally active. For example, a portion of the protein may be used which retains the desired functionality; in the case of the proteins of the invention, this is generally a domain or domains of the protein which are capable of inhibiting one or more proteases. Any such sequence may be used, and any additional sequence may be provided, as long as there is requisite functionality. The functionality need not be as high as the native protein, and thus in some instances may be reduced, the same, or even enhanced as compared to the native protein, and it is understood that the functionality is generally assessed in the context of the fusion protein.

In addition, it is well-understood in the art that amino acid changes, including substitutions, deletions, insertions, post-translational modifications, and the use of amino acid analogs, may be made in the native protein or a portion of the native protein without abolishing or significantly reducing the biological or immunological activity of the protein. Single amino acids may be substituted for others with the same charge or hydrophobicity. Other amino acids may be substituted with amino acids of differing charge or hydrophobicity without significantly altering the function of the protein. It is also contemplated to use variants which enhance the function of the protein as compared to native, or wild type, protein. In addition to substitutions, entire portions of the protein may be deleted without abolishing or significantly affecting the basic biological function of the protein, or extra amino acids inserted without abolishing or significantly affecting the function. Such changes are similar to changes that occur by evolution, and the degree of similarity of two proteins which differ in amino acid sequence can be determined by a method of quantitative analysis such as that described by Pearson and Lipman (Pearson, W. R., and Lipman, D. J., Proc. Natl. Acad. Sci. USA 85:2444–2448, 1998), which compares the homology of amino acid sequences as well as the substitutions of amino acids known to occur frequently in evolutionary families of proteins sharing a conserved function.

In the present invention, a "functionally active portion" of a protease inhibitor is a protein that inhibits a protease and that has an amino acid sequence either identical to, or differing in at least one amino acid from, the native form of the protein or a portion of the native form. If the amino acid sequence is different from the native form, the functionally active portion nonetheless has greater similarity to the native sequence or a portion thereof, for example, as defined by the above comparison algorithm of Pearson and Lipman, or other such comparison accepted in the art, than to the amino acid sequence of any other natural polypeptide from the same species. For example, a functionally active portion of AAT is a polypeptide which inhibits neutrophil elastase, cathepsin G, and/or kallikrein, and which has an amino acid sequence which is either identical to the native AAT sequence or a portion thereof or which is more similar to the native AAT sequence or a portion thereof than it is to any other native human protein, for example, as calculated by the algorithm of Pearson and Lipman. Such functionally active portions of a native protein are often referred to as "analogs" of the protein (e.g., "SLPI analogs"), and the two terms are used synonymously herein.

A fusion protein that comprises a functionally active portion of a protease inhibitor may contain additional sequences. For example, additions to the polypeptide chain at the C- or N-terminus may by useful to facilitate purification by, for example, targeting the protein for extracellular secretion (see, for example, U.S. Pat. No. 4,870,008); such additions are generally cleaved after they have performed their signaling function, thus being a part of the DNA for the protein but not a part of the final protein. Such additions, as well as others, such as a sequence between the protease inhibitor polypeptides of the fusion protein, can be included in the invention.

Each class of proteases has its own class of protease inhibitors. Thus, there are serine protease inhibitors, metalloprotease inhibitors, cysteine protease inhibitors, and aspartate protease inhibitors. All known naturally occurring protease inhibitors are proteins, except for some secreted by microorganisms. This invention encompasses the protein protease inhibitors. As with the proteases themselves, the inhibitors contain highly conserved regions and often have a great deal of homology from member to member within a class.

The serine protease inhibitors include canonical inhibitors, non-canonical inhibitors, and serpins (see, for example, Otlewski, J., Krowarsch, D., and Apostoluk, W., Protein inhibitors of serine proteases, Acta Biochim Polonica, 46:531–565, 1999). Canonical inhibitors bind to the protease in the substrate binding site, and their mechanism of inhibition resembles that of an ideal substrate. Non-canonical inhibitors contain an inhibitory N-terminus which binds to the protease forming a parallel β-pleated sheet. Serpins, the major protease inhibitors in plasma, bind in a manner similar to canonical inhibitors, but their mechanism of action involves the cleavage of a single peptide bond. The serpins are a superfamily of inhibitors, consisting of a single chain with a conserved domain of 370–390 residues (see Potemka, J., Korzus, E, and Travis, J., The serpin superfamily of proteinase inhibitors: structure function, and regulation, J. Biol. Chem. 269:15957–15960, 1994).

Both AAT and SLPI are serine protease inhibitors. AAT has been studied extensively, and the amino acid sequence of the protein was reported by Carrell et al. (*Nature* 298: 329–334, 1982). The protein has been produced by recombinant methods in yeast; see, e.g., Brake et al., U.S. Pat. No. 4,752,576. The major physiological protease targets of AAT include neutrophil elastase, cathepsin G, mast cell chymase, and kallikrein. Functionally active portions of AAT may also be used in the present invention, for example, those described in U.S. Pat. Nos. 6,068,994 and 4,732,973, and in A. Hercz, Proteolytic cleavages in alpha-one antitrypsin and microheterogeneity, Biochem. Biophys. Res. Comm. 128: 199–203, 1985.

The DNA and amino acid sequences of human SLPI were reported by Heinzel et al. (*Eur. J. Biochem.* 160: 61–67, 1987), and are shown in SEQ ID NO: 3 and SEQ ID NO: 4, respectively (see Tables 3 and 4). Also, several patents describe SLPI, its nucleic acid, and/or functionally active portions of SLPI (see, e.g., U.S. Pat. Nos. 4,760,130; 5,464,822; 4,845,076; 5,633,227; 5,851,983; 5,871,956; 5,900,400; 6,017,880; and 6,291,662), any of which may be used in the invention. By using such functionally active portions, one may adjust the inhibitory activity of the molecule to be more focussed on one or another of the proteases the native molecule inhibits. Major protease targets of SLPI are neutrophil elastase, mast cell chymase and tryptase, and chymotrypsin.

TABLE 3

DNA sequence of human SLPI

```
tctggaaagt ctttcaaggc cggtgtttgt ccaccaaaga     60
                                agtccgctca atgtttgaga tacaagaagc cagaatgtca atccgactgg caatgtccag    120
                                gtaagaagag atgttgtcca gacacttgtg gtatcaagtg tctagaccca gttgacaccc    180
                                caaacccaac tagaagaaag ccaggtaagt gtccagttac ttacggtcaa tgtttgatgt    240
                                tgaacccacc aaacttctgt gaaatggacg gtcaatgtaa gagagacttg aagtgttgta    300
                                tgggtatgtg tggtaagtcc tgtgtttccc cagtcaaggc c                        321
```

TABLE 4

Amino acid sequence of human SLPI

```
Ser Gly Lys Ser Phe Lys Ala Gly Val Cys Pro Pro
1               5                   10

Lys Lys Ser Ala Gln Cys Leu Arg Tyr Lys Lys Pro
            15              20

Glu Cys Gln Ser Asp Trp Gln Cys Pro Gly Lys Lys
25              30              35

Arg Cys Cys Pro Asp Thr Cys Gly Ile Lys Cys Leu
            40              45

Asp Pro Val Asp Thr Pro Asn Pro Thr Arg Arg Lys
        50              55                  60

Pro Gly Lys Cys Pro Val Thr Tyr Gly Gln Cys Leu
                65              70

Met Leu Asn Pro Pro Asn Phe Cys Glu Met Asp Gly
        75              80
```

TABLE 4-continued

Amino acid sequence of human SLPI

```
Gln Cys Lys Arg Asp Leu Lys Cys Cys Met Gly Met
85                  90                  95

Cys Gly Lys Ser Cys Val Ser Pro Val Lys Ala
            100                 105
```

In the fusion proteins of the present invention, the AAT-containing sequence may be joined C-terminally to the N-terminus of the second protease inhibitor (or functionally active portion), such as SLPI, or SLPI may be fused C-terminally to the N-terminus of AAT. The fusion of the two proteins of the fusion protein may be by means of a simple peptide bond, or there may be one or more additional amino acids which comprise the fusion linkage between the two proteins of the fusion protein. In a preferred embodiment, there is a methionine between the AAT and the SLPI. There may be additional sequence(s) in one or more locations of the fusion proteins of the invention. Further, it is understood that the relative orientation of each protease inhibitor component (e.g., AAT and second protease inhibitor) encompasses general orientation with respect to C terminus/N terminus, and this encompasses direct linkage of components as well as additional sequence(s) linking components.

In one embodiment of the invention, AAT or a functionally active portion thereof is linked to a metalloprotease inhibitor, or a functionally active portion thereof. Of the metalloproteases, the matrix metalloproteases (MMPs) have been found to be particularly important in a number of normal and pathological conditions. The MMPs, which comprise the collagenases, gelatinases, and stromelysin, have similar structures, with a propeptide, an amino terminal domain, a fibronectin-like domain, a zinc-binding domain, and a C-terminal domain. In addition, some members incorporate a transmembrane domain and a α2V collagen-like domain. The MMPs are inhibited by the tissue inhibitors of matrix metalloproteases, or TIMPs, which are present in all connective tissue. There are four known human TIMPs, referred to as TIMP-1, TIMP-2, TIMP-3, and TIMP-4, which share sequence homology to a consensus sequence. All of these TIMPs (including functionally active fragments, variants, etc.) are encompassed within the invention. TIMP-1 is 43% homologous to the consensus sequence, TIMP-2 is 62% homologous, TIMP-3 is 56% homologous, and TIMP-4 is 61% homologous. The amino acid and nucleotide sequences of all four human TIMPs have been characterized: TIMP-1 (Docherty et al., *Nature* 318: 66–69, 1985), the DNA and amino acid sequences of which are shown in SEQ ID NOs: 5 and 6, respectively (see Tables 5 and 6); TIMP-2 (Boone et al., *Proc. Natl. Acad. Sci.* 87:2800–2804), TIMP-3 (Wilde et al., *DNA Cell Biol.* 13: 711–718); TIMP-4 (Hawkins et al., U.S. Pat. No. 5,643,752). The TIMPs are considered a single class based on their amino acid sequence homology, the fact that each contains 12 cysteines and six disulfide bonds, their ability to inhibit metalloproteases, and the presence of the VIRAK motif which interacts with the metal ion in a metalloprotease. There are both differences and overlap in the protease inhibitory activities of the TIMPs. TIMP-1 inhibits activated interstitial collagenase, the 92 kDa Type IV collagenase, and stromelysin, TIMP-2 inhibits gelatinases A and B as well as the 72 kDA Type IV collagenase, TIMP-3 inhibits collagenase 1, stromelysin, and gelatinases A and B. TIMP-4 appears to inhibit gelatinase and collagenase.

TABLE 5

DNA sequence of human TEMP-1

```
tgcacctgtg tcccacccca cccacagacg gccttctgca     60
                      attccgacct cgtcatcagg gccaagttcg tggggacacc agaagtcaac cagaccacct    120
                      tataccagag ttatgagatc aagatgacca agatgtataa agggttccaa gccttagggg    180
                      atgccgctga catccggttc gtctacaccc ccgccatgga gagtgtctgc ggatacttcc    240
                      acaggtccca caaccgcagc gaggagtttc tcattgctgg aaaactgcag gatggactct    300
                      tgcacatcac tacctgcagt ttcgtggctc cctggaacag cctgagctta gctcagcgcc    360
                      ggggcttcac caagacctac actgttggct gtgaggaatg cacagtgttt ccctgtttat    420
                      ccatccctg caaactgcag agtggcactc attgcttgtg gacggaccag ctcctccaag    480
                      gctctgaaaa gggcttccag tcccgtcacc ttgcctgcct gcctcgggag ccagggctgt    540
                      gcacctggca gtccctgcgg tcccagatag cc                                  552
```

TABLE 6

Amino acid sequence of human TIMP-1

Cys Thr Cys Val Pro Pro His Pro Gln Thr Ala Phe
 1                5                   10

Cys Asn Ser Asp Leu Val Ile Arg Ala Lys Phe Val
              15                  20

Gly Thr Pro Glu Val Asn Gln Thr Thr Leu Tyr Gln
 25                  30                     35

Arg Tyr Glu Ile Lys Met Thr Lys Met Tyr Lys Gly
                 40                  45

Phe Gln Ala Leu Gly Asp Ala Ala Asp Ile Arg Phe
 50                  55                       60

Val Tyr Thr Pro Ala Met Glu Ser Val Cys Gly Tyr
                 65                          70

Phe His Arg Ser His Asn Arg Ser Glu Glu Phe Leu
             75                  80

Ile Ala Gly Lys Leu Gln Asp Gly Leu Leu His Ile
 85                  90                       95

Thr Thr Cys Ser Phe Val Ala Pro Trp Asn Ser Leu
                100                 105

Ser Leu Ala Gln Arg Arg Gly Phe Thr Lys Thr Tyr
110                 115                     120

Thr Val Gly Cys Glu Glu Cys Thr Val Phe Pro Cys
                125                         130

Leu Ser Ile Pro Cys Lys Leu Gln Ser Gly Thr His
                135                 140

Cys Leu Trp Thr Asp Gln Leu Leu Gln Gly Ser Glu
145                 150                     155

Lys Gly Phe Gln Ser Arg His Leu Ala Cys Leu Pro
                160                         165

Arg Glu Pro Gly Leu Cys Thr Trp Gln Ser Leu Arg
                170                 175         180

Ser Gln Ile Ala

The complete structure of a TIMP is not necessarily a requirement for metalloprotease inhibition. For example, functionally active portions of TIMP-2 (often referred to as "TIMP-2 analogs") have been prepared that retain their inhibitory activity toward metalloproteases (see Willenbrock et al., Biochemisty 32: 4330–4337, 1993). A partial sequence of TIMP-1 that contains only the first three loops of the molecule is capable of inhibiting matrix metalloproteases. (Note: the words "metalloprotease" and "metalloproteinase" are synonymous and both are used when referring to these enzymes in the literature; for consistency we will use only "metalloprotease" herein). The N-terminus of the TIMP molecule is where the inhibitory activity is found, and the inhibitory mechanisms appear to involve several specific amino acid sequences. (see, for example, Murphy, G. Houbrechts, A., Cockett, M. I., Williamson, R. A., O'Shea, M., and Docherty, AJP, The N-terminal domain of TIMP retains metalloprotease activity. *Biochemistry* 30: 8097–8102, 1991; Woessner, J., Matrix metalloproteases and their inhibitors in connective tissue remodeling. *FASEB J* 5: 2145–2154, 1991, and EPA publication #0648838 A1, Tissue inhibitor of metalloprotease type three (TIMP-3), Silbiger and Koski). One preferred N-terminal fragment of TIMP-1 for construction of some embodiments of the present invention is the first 126 N-terminal amino acids of the native form. In making constructs this fragment is often used with an initial methionine, and thus contains 127 amino acids (the initial methionine plus the N-terminal 1–126 amino acids of TIMP-1); this fragment is referred to as N-TIMP 1–127 (see SEQ ID NO: 22 and Table 30). Another preferred N-terminal fragment of TIMP-1 for construction of other embodiments of the present invention is the first 127 N-terminal amino acids of the native form. Amino acid 127 of this fragment is a free cysteine, and is thus available to participate in disulfide bond formation, which is one manner of constructing the fusion proteins of the invention. In making constructs this fragment is often used with an initial methionine, and thus contains 128 amino acids (the initial methionine plus the N-terminal 1–127 amino acids of TIMP-1); this fragments is referred to as N-TIMP 1–128 (see SEQ ID NO: 24 and Table 32).

In the AAT-TIMP fusion proteins of the present invention, AAT may be linked C-terminally to the N-terminus of TIMP, or TIMP may be fused C-terminally to the N-terminus of AAT. The fusion of the two proteins of the fusion protein may be by means of a simple peptide bond, or there may be one or more additional amino acids which comprise the fusion linkage between the two proteins of the fusion protein.

Cysteine proteases are inhibited by the cystatins, stefins, and kininogens. The cystatins and stefins consist of an α-helix surrounded by a five-stranded antiparallel β-pleated sheet, forming a wedge that is complementary to the active site of the protease. At one end of the β-pleated sheet is a highly conserved β-hairpin loop with the sequence QVVAG (SEQ ID. NO: 11)(see Barrett et al., in Proteinase inhibitors (Barret, A. J. and Salvesen, G., eds) pp. 515–569, Elsevier, Amsterdam, 1986, and Turk, V., and Bode, W., FEBS Lett. 285:213–219, 1991. One embodiment of the present invention is AAT or a functionally active portion thereof linked to a cystatin, stefin, or kininogen or functionally active portion thereof.

Aspartyl proteases include the HIV aspartyl protease, renin (involved in hypertension), pepsin, cathepsin D (implicated in tumor metastasis), and aspartyl hemoglobinases (from the malarial parasite).

The HIV protease cleaves polyprotein precursors to the functional proteins of the virion core in the final stages of viral maturation. Its inhibition has been a major target for HIV and AIDS treatment (Huof, J. R., "HIV protease: a novel chemotherapeutic target for AIDS," *J. Med. Chem.* 34:2305–2314). Several HIV protease inhibitors, including ritonavir, Crixivan, and saquinavir, have been approved by the FDA for HIV treatment. Cathepsin D is a lysosomal protein which normally is involved in the degradation of intracellular or phagocytosed proteins. However, it has been implicated in a number of diseases. For example, cathepsin D may degrade the extracellular matrix and promote the escape of cancer cells in metastasis and invasion of new tissues, and also appears to be an agent in pathological brain changes such as those seen in Alzheimer's disease. Elevated levels of cathepsin D have been observed in cerebrospinal fluid of Alzheimer's patients, and it is associated with the cleavage of the amyloid-β-protein precursor. The malarial parasite aspartyl proteases, Plasmepsins I and II, are highly homologous with human cathepsin D, and are essential in the breakdown of hemoglobin to products which the parasite uses for nutrition. Inhibitors of these proteases kill the parasite in cell culture of infected human erythrocytes. Renin is an enzyme originating in the kidney which converts angiotensinogen to angiotensin, a crucial event in the renin-angiotensin modulation of blood pressure, ultimately resulting in the production of angiotensin II which is a powerful vasoconstrictor. Hence, inhibitors of renin have long been considered as candidates for the control of hypertension.

The most well-known of the natural aspartyl protease inhibitors is pepstatin, a peptide originally isolated from a culture of streptomyces, with the formula isovaleryl-L-valyl-L-valyl-statyl-L-alanyl-statin, (SEQ ID NO: 12) in which "statin" is the unusual amino acid (3S,4S)-4-amino-3-hydroxy-6-methyl-heptanoic acid. Pepstatin is active against pepsin, cathepsin D, and renin. In addition to pepstatin, many protease inhibitors targeted at the various aspartyl proteases have been designed and produced, often based on the structure of pepstatin (see U.S. Pat. No. 4,746,648; Umezawa, H, et al., Pepstatin, a new pepsin inhibitor produced by Actinomycetes. *J Antibiot* (Tokyo) 23:259–62, 1970; Morishima, H., et al., The structure of pepstatin. *J Antibiot* (Tokyo) 23:263–5, 1970; Lin, Ty and Williams, H R., Inhibition of cathepsin D by synthetic oligopeptides. *J. Biol. Chem.* 254:11875–83, 1979; Jupp, R A, et al., The selectivity of statin-based inhibitors against various human aspartic proteinases, *Biochem. J.* 265:871–8, 1990; Agarwal, N S and Rich, D H, Inhibition of cathepsin D by substrate analogues containing statine and by analogues of pepstatin, *J. Med. Chem.* 29:2519–24, 1986; Baldwin, E T, et al., Crystal structures of native and inhibited forms of human cathepsin D: implications for lysosomal targeting and drug design. *Proc. Natl. Acad. Sci., USA* 90: 6796–800, 1993; Francis, S E et al., Molecular characterization and inhibition of a Plasmodium falciparum aspartyl hemoglobinase, *EMBO J* 13: 306–17, 1994). One embodiment of the present invention is AAT or a functionally active portion thereof linked to an aspartyl protease inhibitor, such as pepstatin, or a functionally active portion thereof.

Production of the fusion proteins, polynucleotides, and host cells of the invention. Ordinarily, production of the fusion proteins of the present invention is accomplished by constructing the appropriate polynucleotide (generally DNA) sequence and expressing it in recombinant cell culture. Alternatively, however the polypeptides of this invention may be synthesized according to other known methods. Techniques for synthesis of polypeptides are described, for example, in Merrifield, J. Amer. Chem. Soc. 85:2149–2156, 1963. Polypeptide chains containing protease-inhibiting domains may be joined by a peptide bond, or by links between amino acid side chains, e.g., disulfide bonds, by methods well-known to those of skill in the art.

The recombinant fusion proteins are produced by an expression vector or plasmid comprising DNA segments that direct the synthesis of the fusion protein, also in accordance with the present invention. Such polynucleotides include RNA, cDNA, genomic DNA, synthetic forms, and mixed polymers, both sense and antisense strands. Such polynucleotides can be chemically or biochemically modified and can contain non-natural or derivatized nucleotide bases. The sequence encoding the fusion polypeptide can be interrupted by introns. The polynucleotide sequences of this invention are of a length sufficient to encode such a fusion polypeptide and, if necessary, any vector sequences. The sequences are usually several hundred nucleotides or nucleotide base pairs in length and may be several kilobases long. In other embodiments in which joining of protease inhibitors is via one or more disulfide bonds, the polynucleotides encoding the polypeptide chains of the individual inhibitors may be expressed separately, generally by being in separate vectors.

The present invention also encompasses methods for producing the fusion proteins, and pharmaceutical compositions containing the fusion proteins.

Techniques for polynucleotide manipulation, including the construction of polynucleotides capable of encoding and expressing the fusion polypeptides of the present invention, are well known and are described generally, for example, in Sambrook et al., op. cit., or Ausubel et al., op. cit. Reagents useful in applying such techniques, such as restriction enzymes and the like, are widely known in the art and commercially available.

The recombinant polynucleotide sequences used to produce fusion polypeptides of the present invention (or used to produce antisense sequences) may be derived from natural or synthetic sequences. To construct the fusion proteins by recombinant methods, the appropriate polynucleotide sequences are operably linked. A polynucleotide sequence is "operably linked" when it is in a functional relationship with another polynucleotide sequence. For instance, a promoter is operably linked to a coding sequence if the promoter affects its transcription or expression. Generally, operably linked means that the DNA sequences being linked are contiguous and, where necessary to join two polypeptide coding regions, contiguous and in reading frame. Sequences coding for signal peptides (i.e., leader sequences) may also be added to the recombinant polynucleotide sequences, so that the polypeptide chain produced is routed to the appropriate intracellular or extracellular space for further manipulation, e.g., extraction and purification. The signal peptides from, for example, AAT (SEQ ID NOS:25 and 26, see Tables 7 and 8, for DNA and amino acid sequences, respectively ), SLPI (SEQ ID NOS:27 and 28, see Tables 9 and 10, for DNA and amino acid sequences, respectively) TIMP-1 (SEQ ID NOS: 29 and 30, see Tables 11 and 12, for DNA and amino acid sequences, respectively), α-factor signal (yeast) (SEQ ID NOS:31 and 32, see Tables 13 and 14, for DNA and amino acid sequences, respectively), human serum albumin signal, or other proteins can be used to signal the secretion of these proteins from various cell lines, using methods known in the art.

TABLE 7

DNA for leader sequence for human AAT (Kurachi, K. et al, 1981, Proc Natl. Acad. Sci 78, p.6826.)

ATGCCGTCTTCTGTCTCGTGGGGCATCCTCCTGCTGGCAGGCCTGTG 60
CTGCCTGGTCCCT

GTCTCCCTGGCT 73

TABLE 8

Amino acid sequence of leader sequence for human AAT (Kurachi, K. et al, 1981, Proc Natl. Acad. Sci 78, p.6826.)

MPSSVSWGILLLAGLCCLVPVSLA 24

TABLE 9

DNA for leader sequence for human SLPI (Heinzel, R. et al., 1986, Eur. J. Biochem. 160,p. 61.)

ATGAAGTCCAGCGGCCTCTTCCCCTTCCTGGTGCTGCTTGCCCTGGG 60
AACTCTGGCACCT

TGGGCTGTGGAAGGC 75

TABLE 10

Amino acid sequence of leader sequence for human SLPI (Heinzel, R. et al., 1986, Eur. J. Biochem. 160,p. 61.)

MKSSGLFPFLVLLALGTLAPWAVEG 25

TABLE 11

DNA for leader sequence for human TIMP-1 (Docherty, AJ et al, 1985, Nature 318, p. 66)

ATGGCCCCCTTTGAGCCCCTGGCTTCTGGCATCCTGTTGTTGCTGTG 60
GCTGATAGCCCCC

AGCAGGGCC 70

TABLE 12

Amino acid seguende of leader sequence for human TIMP-1 (Docherty, AJ et al, 1985, Nature 318, p. 66)

MAPFEPLAS-GILLLLWLIAPSRA 23

TABLE 13

DNA fof leader sequence for alpha factor from S. cervisiae (Kurjan,J. and Herskowitz,I., 1982, Cell 30, p. 933)

ATGAGATTTCCTTCAATTTTTACTGCAGTTTTATTCGCAGCATCCTC 60
CGCATTAGCTGCT

CCAGTCAACACTACAACAGAAGATGAAACGGCACAAATTCCGGCTGA 120
AGCTGTCATCGGT

TACTCAGATTTAGAAGGGGATTTCGATGTTGCTGTTTTGCCATTTTC 180
CAACAGCACAAAT

AACGGGTTATTGTTTATAAATACTACTATTGCCAGCATTGCTGCTAA 240
AGAAGAAGGGGTA

TCTCTAGATAAAAGAGAGGCTGAAGCTTG 269

TABLE 14

Amino acid sequence of leader sequence for alpha factor from S.cervisiae (Kurjan, J. and Herskowitz,I., 1982, Cell 30, p. 933)

MRFPSIFTAVLFAASSALAAPVNTTTEDETAQIPAEAVIGYSDLEGD 60
FDVAVLPFSNSTN

NGLLFINTTIASIAAKEEGVSLDKREAEA 89

The polynucleotide sequences given for the constituent proteins of the fusion proteins of the present invention represent only one example of the polynucleotide sequences that may be used in the present invention. Because the genetic code is degenerate, more than one codon may be used to code for a given amino acid, and there will be many different DNA sequences which code for the same polypeptide sequence. The use of non-naturally-occurring codons in the nucleotide sequences coding for the desired fusion proteins may be advantageous in that different codons, which may be preferred by different prokaryotic or eukaryotic hosts (see Murray, E. E., Nuc. Acids Res. 17:477–508, 1989), may be used to modify the expression of the fusion protein in a variety of desirable ways. These include increasing the rate of expression of the fusion protein, or producing RNA transcripts having a longer half-life than those produced from DNA containing the naturally-occurring codons.

The polynucleotides of the present invention are optionally produced by chemical synthesis, e.g., by the phosphoramidite method described by Beaucage and Carruthers (Tetra, Letts. 22:1859–1862, 1981) or the triester method according to Matteucci et al. (J. Am. Chem. Soc. 103:3185, 1981). Chemical synthesis may be performed on commercial automated oligonucleotide synthesizers.

Large amounts of the polynucleotides of the present invention may be produced by replication in a suitable host cell, whether bacterial, yeast, such as *Saccaromyces cerevisiae*, insect, amphibian, avian, mammalian or other cells and expression systems. The natural or synthetic polynucleotide (such as DNA) fragments coding for a desired fragment will be incorporated into recombinant polynucleotide constructs, typically DNA constructs.

These constructs are introduced into prokaryotic or eukaryotic cells where they replicate. Usually the constructs are suitable for autonomous replication in a unicellular host, such as yeast or bacteria. A preferred host cell for the present invention is yeast, for example *Saccharomyces cerevisiae, Pichia pastoris, Hansenula polymorpha*, and *Kluyveromy-* ces lactis. The constructs also can be introduced to and integrated within the genome of a cultured insect, mammalian, plant or other eukaryotic cell lines. Suitable methods for these purposes are well known in the art and have been described, e.g., in Sambrook et al. (1989) or Ausubel et al. (1987 and periodic updates).

Polynucleotide constructs prepared for introduction into a prokaryotic or eukaryotic host typically comprise a replication system recognized by the host, including the intended DNA fragment encoding the desired polypeptide, and preferably also include transcription and translational initiation regulatory sequences operably linked to the polypeptide encoding segment. Expression vectors include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors are prepared by means of standard recombinant techniques well known in the art and discussed, for example, in Sambrook et al. (1989) or Ausubel et al. (1987).

Appropriate promoter and other necessary vector sequences are selected to function in the host. Examples of functional combinations of cell lines and expression vectors are described in Sambrook et al., 1989 or Ausubel et al., 1987); see also, e.g., Metzger et al., Nature 334:31–36, 1988. Many useful vectors are known in the art and are commercially available. For use in prokaryotic hosts, promoters include but are not limited to the trp, lac and phage promoters, tRNA promoters and glycolytic enzyme promoters. Useful yeast promoters include but are not limited to the promoter regions for metallothionein, 3-phosphoglycerate kinase or other glycolytic enzymes such as enolase or glyceraldehyde-3-phosphate dehydrogenase, and enzymes responsible for maltose and galactose utilization. A preferred promoter and terminator in yeast is ADH2. Other suitable vectors and promoters for use in yeast expression are further described in Hitzeman et al. EP 73,657A. Appropriate nonnative mammalian promoters include but are not limited to the early and late promoters from SV40 (Fiers et al. Nature 273:113, 1978) or promoters derived from murine molony leukemia virus, mouse mammary tumor virus, avian sarcoma viruses, adenovirus II, bovine papilloma virus and polyoma virus. In addition, the construct can be joined to an amplifiable gene (e.g., DHFR) so that multiple copies of the gene are made.

Such expression vectors can replicate autonomously. Alternatively, the expression vector can replicate by being inserted into the genome of the host cell, by methods well known in the art.

Expression and cloning vectors generally include a selectable marker, which encodes a polypeptide necessary for the survival or growth of its host cells. This gene's presence ensures the growth of only host cells expressing the marker. Typical selection genes encode polypeptides that (a) confer resistance to antibiotics or other toxic substances, e.g. ampicillin, neomycin, methotrexate, etc.; (b) complement auxotrophic deficiencies; or (c) supply critical nutrients not available from complex media. The choice of the proper selectable marker depends on the host cell. A preferred marker in yeast host cells is the URA3 gene, which provides a selectable marker in the yeast 2 micron plasmid for autonomous replication in yeast. Appropriate markers for different hosts are well known in the art.

One of skill in the art will recognize that there are a number of types of host cell, both prokaryotic and eukaryotic, that will be suitable for expression of the fusion proteins of the present invention. The most commonly used prokaryotic hosts are strains of *E. coli*, although other prokaryotes, such as *Bacillus subtilis* or Pseudomonas, may also be used. Mammalian or other eukaryotic host cells, such as those of yeast, filamentous fungi, plant, insect, amphibian or avian species, may also be useful for production of the polypeptides of the present invention, as well as the COS, CHO and HeLa cells lines and myeloma cell lines. The preferred host cell type for the present invention is yeast, such as *Saccharomyces cerevisiae, Pichia pastoris, Hansenula polymorpha*, and *Kluyveromyces lactis*. Each type of host cells requires that the recombinant protein gene be operably linked to appropriate expression control sequence. Such control sequences include a promoter such as the T7, trp, or lambda promoters, a ribosome binding site and preferably a transcription termination signal, for *E. coli*, or a promoter and preferably an enhancer derived from immunoglobulin genes, SV40, cytomegalovirus, etc., and a polyadenylation sequence, for eukaryotic cells, and may include splice donor and acceptor sequences.

Vectors with the polynucleotides of interest can be transcribed in vitro, and the resulting RNA are introduced into host cells by well known methods (e.g. by injection). See, T. Kubo et al., *FEBS Lett.* 241:119, 1988. Alternately, the vectors can be introduced directly into host cells by methods well known in the art, which vary depending on the type of cellular host. These methods include but are not limited to electroporation; transfection employing lithium acetate, which is the preferred method, or calcium chloride, rubidium chloride calcium phosphate, DEAE-dextran, or other substances; microprojectile bombardment; lipofection; and infection (where the vector is an infectious agent, such as a retroviral genome). See generally, Sambrook et al. (1989) and Ausubel et al. (1987). The so-transformed cells are also meant to include the progeny of such cells.

The invention as claimed does not call for a purified protein, and purification need be carried out only to the level of purity appropriate for the desired use of the proteins. Standard purification techniques, well-known in the art, may be used to purify the proteins after expression, including affinity columns, ammonium sulfate precipitation, column chromatography, gel electrophoresis and the like. Such techniques are described in, for example, R. Scopes, "Protein Purification", Springer-Verlag, N.Y. (1982).

Assay of the fusion proteins. The activities of the protease inhibitors may be assessed by means known in the art for each of the individual protease inhibitors; in general, one assays the activity of the appropriate protease in the presence and in the absence of the inhibitor. See, e.g., Barrett, Alan J., ed. Proteolytic enzymes: serine and cysteine peptidases. *Meth Enz* Vol. 244, San Diego, Academic Press, 1994.

Preferred assay methods determine AAT activity by inhibition of porcine pancreatic elastase in a microtiter plate format, or by inhibition of human neutrophil elastase, SLPI tryptase-inhibiting activity by HPLC-based methods, and matrix metalloprotease activities, as described in Examples.

For SLPI, an assay is commonly based on the ability of the substance to inhibit a serine protease, preferably leukocyte or pancreatic elastase. The inhibitor is mixed with a known concentration of protease and the residual enzyme activity is assessed by its ability to hydrolyze methoxysuccinyl-alanyl-alanyl-prolyl-valine-p-nitroanilide, as described by T. Teshima et al., *J. Biol. Chem.* 257: 5085–91, 1982, and K. Nakajima et al., *J. Biol. Chem* 254:4027–32, 1979. The dissociation constant, Ki, of the complex formed from the interaction of the inhibitor with leukocyte or porcine pancreatic elastase may be obtained by standard kinetic methods. In addition, AAT, SLPI and the fusion proteins of the present invention may be assayed for their abilities to inhibit airway hyperresponsiveness in an animal model (e.g. allergen-challenged sheep).

Assays for the TIMPs have been described in U.S. Pat. Nos. 5,595,885 and 5,643,752 and EP Nos. 0404750B1 and 0648838A1. These assays involve the inhibition of a collagenase or a gelatinase by the TIMP, usually by assessing the collagenase or gelatinase activity by its ability to digest a gelatin, which can be, for example, $^{14}$C labeled (see Collier et al, *J. Biol. Chem.*, 263: 6579–81,1988; and Wilhelm et al., *Proc. Natl. Acad. Sci. USA* 84: 6725–6729, 1987). In addition, AAT, the TIMPs, and the fusion proteins of the present invention may be assayed for the inhibition of development of emphysema in murine models. Such assays may include standard laboratory strains of mice, or transgenically modified mice that are treated with cigarette smoke over extended periods.

Aspartyl protease inhibitors are assayed according to the protease of interest. HIV-1 protease inhibition may be assayed by the method described essentially by M. W. Pennington et al., Peptides 1990, Gimet, E. and Andrew, D., eds, Escom; Leiden, Netherlands, (1990). Pepstatin-like inhibitors may be assayed by the method of Guyene, T T, et al., Inhibition of human plasma renin activity by pepstatin, J. Clin. Endocrinol. Metab., 43:1301–6, 1976, described in U.S. Pat. No. 4,746,648. For inhibitors of cathepsin D and plasmepsins, the assay method described in U.S. Pat. No. 5,849,691 may be used.

III. Pharmaceutical Compositions

The proteins of the invention, fragments thereof, as well nucleic acids of the invention (also referred to herein as "active compounds") can be incorporated into pharmaceutical compositions. Such compositions typically include the protein or nucleic acid and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compounds of the invention also can be formulated into a slow-release (e.g., sustained delivery) formulation, for example a formulation that allows release of the compound over days, weeks or months, using slow-release formulations known in the art for delivery of proteinaceous compounds are known in the art. Furthermore, the compounds of the invention can be formulated to protect them from protease degradation.

For administration by inhalation, the compounds are delivered in the form of an aerosol spray from pressured container or dispenser that contains a suitable propellant, e.g., a gas such as carbon dioxide. Alternatively, the compounds are delivered using a CFC-free metered dose inhaler, or a nebulizer. Dry proteins in carriers such as mannitol, sucrose, or lactose may be delivered in a spray to the lower airway epithelia, which are permeable to proteins up to about MW 20 kDa. Particles of approximately one micron in diameter may be delivered to the distal alveolar surface via dry powder inhalers, such as those designed by Inhale, Dura, and other manufacturers known to those of skill in the art. Ultrasonic nebulizers may be used to deliver solutions, with or without liposomes. Large porous particles are also an effective method for pulmonary delivery using dry powder. Further discussion of pulmonary delivery of drugs maybe found in McElvaney, et al., *J. Clin Invest.* 90:1296–1301, 1992, and Vogelmeier et al., *J. Appl. Physiol.* 69:1843–1848, 1990, and Edwards et al., Large porous particles for pulmonary drug delivery, *Science* 276: 1868–1871, 1997, and U.S. Pat. Nos. 6,254,854; RE37,053; 6,136,295; 5,985,309; 6,253,762; 6,143,277; and 6,131,566.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

It is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, inhalation, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

IV. Compositions and Kits of the Invention

The invention also provides compositions and kits used in the methods described herein. Generally, the compositions of the invention for use in inhibiting proteases comprise an effective amount of a fusion protein comprising AAT and another protease inhibitor or functionally active portions thereof. The compositions are generally in a suitable medium, although they can be in lyophilized form. Suitable media for in vitro use include, but are not limited to, aqueous media (such as pure water or buffers). Compositions intended for in vivo use in the inhibition of proteases and/or treatment of pathological conditions or disease will generally be provided with a pharmaceutically acceptable excipient or carrier, and may be in various formulations, depending on the route of administration, dosage, stability, and other factors well-known in the art. The compositions may be any fusion protein, polynucleotide, vector, host cell, transformed cell, reaction mixture and/or intermediate described herein, as well as any combination. For example, one embodiment of a composition of the present invention is a fusion protein comprising AAT or a functionally active portion thereof and SLPI or a functionally active portion thereof, together with a suitable excipient or carrier for administration to a human being.

The invention also provides kits for carrying out the methods of the invention. Accordingly, a variety of kits are provided in suitable packaging. The kits may be used for any one or more of the uses described herein, including in vitro and in vivo uses, including: application to biological samples (e.g., tissue or organ samples, cultures, blood, plasma, serum, urine, saliva, sputum, and the like) to inhibit protease activity in the sample and thereby stabilize protein proteins in the sample, treatment of individuals at risk for, or suffering from, a disease or disorder associated with an imbalance of proteases and protease inhibitors (e.g., asthma, chronic obstructive pulmonary disease, emphysema, and otitis media and otitis externa). Kits for in vitro methods may also include the appropriate components to facilitate the desired reactions of the methods, for example, buffers, enzymes, substrates, cofactors, and other necessary reagents. Such components may be in lyophilized form. Kits for in vivo administration may also include the appropriate components to facilitate administration by a particular route, e.g. inhalation, intravenous administration, topical administration, subcutaneous administration, intramuscular administration, intraarticular administration, oral administration, intraocular administration and oral administration.

The kits of the invention may optionally include a set of instructions, generally written instructions, although electronic storage media (e.g. magnetic diskette or optical disk) containing instructions are also acceptable, relating to the use of components of the methods of the present invention for the intended protease inhibition, whether in vitro or in vivo. The instructions included with the kit generally include information as to reagents (whether included or not in the kit) necessary for practicing the methods of the presentation invention, instructions on how to use the kit, appropriate reaction conditions and/or appropriate administration conditions, dosage where appropriate, stability, storage, interpretation of results, precautionary measures if appropriate, and the like.

The component(s) of the kit may be packaged in any convenient, appropriate packaging. The components may be packaged separately, or in one or multiple combinations.

One or more compositions in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The relative amounts of the various components in the kits can be varied widely to provide for concentrations of the reagents, excipients, and/or other components that substantially optimize the reactions that need to occur to practice the methods disclosed herein and/or to further optimize the protease inhibition desired.

V. Methods of Invention

Due to their protease inhibiting activity, the fusion proteins of the invention can be used to inhibit the activity of one or more proteases, either in vitro or in vivo. Methods of using the protease inhibitor fusion proteins of the invention in vitro can be applied, for example, to biological samples as a means to inhibit protease activity in the sample and thereby stabilize proteins in the sample. Methods of using the protease inhibitor fusion proteins of the invention in vivo can be applied, for example, to the treatment of individuals suffering from, or at risk for, a disease or disorder associated with an imbalance of proteases and protease inhibitors, e.g., asthma, chronic obstructive pulmonary disease, emphysema, and otitis media and otitis externa.

The invention generally provides a method for inhibiting protease activity comprising contacting the protease with a fusion protein of the invention such that the activity of the protease is inhibited. A protease can be contacted with the fusion protein in vitro by, for example, adding the fusion protein to a sample (e.g., a biological sample) or culture (e.g., cell culture) in vitro. Nonlimiting examples of samples include biological fluids such as blood, plasma, serum, urine, saliva, sputum and the like, tissue samples and cellular cultures. A protease can be contacted with the fusion protein in vivo in an individual by, for example, administering the fusion protein to the individual by an appropriate route to deliver the fusion protein to the site of protease. Nonlimiting examples of appropriate routes of administration include inhalation, intravenous administration, topical administration, subcutaneous administration, intramuscular administration, intraarticular administration, oral administration, intraocular administration and oral administration. The invention generally provides a method of treating an individual suffering from, or at risk for, a disease or disorder involving unwanted protease activity comprising administering to the individual an effective amount of a fusion protein of the invention.

The present invention provides for both prophylactic and therapeutic methods of treating a subject at risk of (or susceptible to) a disorder or having a disorder associated with an imbalance of proteases and protease inhibitors. With regards to both prophylactic and therapeutic methods of treatment, such treatments may be specifically tailored or modified, based on knowledge obtained from the field of pharmacogenomics. The compositions of the present invention are useful in treating a number of diseases where more than one protease is involved in the disease process. In addition, some proteases destroy protease inhibitors, e.g., metalloproteases are known to destroy alpha 1-antitrypsin. Thus, a fusion protein containing two different inhibitors may be especially potent because the inhibitors not only serve to inhibit proteases involved in the disease process, but also serve to protect each other from proteases that would otherwise destroy them.

The amount of the compositions of the present invention, as well as the route of delivery, will depend on the recipient and the condition being treated, and may be determined without undue experiment by one of skill in the art. Specific conditions lend themselves to particular forms of administration, as discussed below, but these are exemplary only.

The compositions of the present invention find particular use in respiratory diseases, such as chronic obstructive pulmonary disease (COPD), cystic fibrosis (CF), asthma, and emphysema. For treatment of such diseases, a fusion protein of the invention preferably is administered directly to the lung via inhalation therapy. A global strategy for protease inhibition provided by the present invention provides significant therapeutic benefits for the treatment of both the airway hyperresponsiveness and the chronic airways remodeling components of asthma, retardation of the development of pulmonary emphysema induced by cigarette smoking, and reduction in exacerbations of CF induced by *P. aeruginosa* infection. Several protease inhibitors, with complementary inhibition spectra, are included in the fusion proteins of the present invention. These include alpha 1-antitrypsin (AAT), tissue inhibitors of metalloprotease (TIMPs), and secretory leukocyte protease inhibitor (SLPI). A fusion protein of AAT and SLPI (including functionally active portions thereof) can be used to inhibit mast cell tryptase and chymase, and neutrophil elastase, cathepsin G and kallikrein for the treatment of asthma, and a fusion protein of AAT and a TIMP can be used to inhibit matrix metalloproteases and neutrophil elastase and cathepsin G for the treatment of COPD and CF. Particularly advantageous in diseases of the lungs and airways is the fact that the compositions of the invention are subject to direct pulmonary delivery, thus directly targeting the affected tissue, as discussed above.

The compositions of the present invention find additional use in the treatment of dermatological diseases such as atopic dermatitis, eczema and psoriasis, in inflammatory responses to viral infection, such as to herpes virus types I and II, and varicella zoster virus, and in treatment of infections of the ear (e.g., otitis media and otitis externa). In these diseases, elevated levels of neutrophil elastase, and mast cell derived proteases have been identified. Similarly, in chronic bacterial infection of the middle ear (chronic otitis media), proteases have been identified that can inhibited by serine protease inhibitors, and by metalloprotease inhibitors. A fusion protein of AAT with a TIMP would be particularly advantageous in this condition, leading to decreased sequelae of the inflammatory response, and inhibition of bacterial metalloproteases. For treatment of dermatological conditions, a fusion protein of the invention preferably is administered topically to an individual.

The compositions of the present invention may also be useful in HIV infections, where an aspartyl protease is a major protein coded for by the viral nucleic acid, and where protease inhibitors have been found to be especially powerful in treatment of the disease. Furthermore, host cell serine proteases are involved in cleavage of the HIV envelope (env) gene product, and both SLPI and AAT have been shown to inhibit HIV replication when administered individually in in vitro assay systems. Accordingly, the invention provides a method for inhibiting HIV protease activity by contacting the HIV protease with a fusion protein of the invention. Furthermore, the invention provides methods for inhibiting HIV replication in an individual, or of decreasing HIV infectivity in an individual, or of prolonging survival of an HIV-infected individual, by administering to the individual a fusion protein of the invention, such as a SLPI/AAT fusion protein.

The compositions of the present invention may also be useful in the treatment of a number of other conditions. For the treatment of dermatitis, psoriasis, herpes infection, corneal or epidermal ulceration, chronic non-healing wounds, and sepsis, administration may be systemic, by the methods described above, or topical, using a suitable carrier. Otitis media may be treated by oral or intramuscular administration, or by ear canal instillation. For treatment of rheumatoid arthritis and osteoarthritis, the administration may be local or systemic, or the fusion proteins of the present invention may be injected directly into the affected joint(s), or applied in combination with a penetrating agent by patch applied over the affected area. In the treatment of periodontal disease, administration of a penetrating treatment may be by means of gel, toothpaste, mouthwash, spray, or lozenge, in order to slow or halt the destruction of connective tissue. For treatment of tumor metastasis and tumor angiogenesis, the fusion proteins of the present invention may be delivered intraarterially in an amount sufficient to prevent the tumor-produced proteases from destroying surrounding connective tissue, allowing angiogenesis or metastasis. Other conditions, such as gastric ulceration, osteoporosis, Paget's disease of bone, glomerulonephritis, scleroderma, pressure atrophy of bone or tissues, cholesteatoma, nerve cell disorders, ischemia-reperfusion injury of organs (including local sequelae of myocardial anoxia), malaria, Chagas disease, parasitic eye infection, viral infection (e.g. HIV, herpes), bacterial infection, Alzheimer's disease, hypertension, acute leukemia, dystrophic epidermolysis bullosa, and muscular dystrophy, may be treated by methods known in the art for the treatment of each pathological condition.

Other diseases or conditions that may be treated according to the methods of the invention using a fusion protein of the invention include viral infections, such as herpes infections, as well as inflammatory responses to viral infections, such as inflammatory responses to herpes infection. The fusion proteins of the invention also can be used in the treatment of inflammation in general, whether resulting from a viral infection or other cause.

For the treatment of conditions in which an excess of protease inhibitors is implicated, such as corneal or diabetic ulcers, or lesions produced by infectious microorganisms, antisense molecules to the protease inhibitors may be administered directly to the site of the lesion by means of irrigation, salves, or other appropriate means.

The compositions of the present invention are useful in vitro, in any application where broad spectrum protection against proteases is desired, for example, during preparation and analysis of biological samples or during protein purification from tissue sources. In these and other procedures a number of proteases are released and/or activated, and a broad-spectrum protease inhibitor such as the fusion proteins of the present invention can be used to prevent the proteolysis of the protein of interest in the mixture. Because the specificity of the fusion proteins can be tailored to proteases alone, and to particular classes of proteases, it is possible to specifically inhibit proteolysis by tissue- or organ-specific proteases without affecting other proteins of interest. In addition, the components of the fusion proteins of the present invention can serve to protect each other from proteolytic digestion, thus multiplying the duration of effectiveness for the inhibitors.

This invention is further illustrated by the following examples, which should not be construed as limiting. The contents of all references, patents and published patent applications cited throughout this application are incorporated herein by reference in their entirety.

EXAMPLES

Example 1

Construction of SLPI/AAT and TIMP-1/AAT Fusion Proteins

A fusion protein comprising amino acids 1–107 of human SLPI fused to amino acids 1–394 of human AAT was constructed and referred to as SLAPI. The nucleotide sequence which was used in the construction of the SLAPI fusion protein is shown in SEQ ID NO: 7 (see Table 15), in which nucleotides 1–6 represent an XbaI restriction site, nucleotides 6–8 represent a ribosome binding site, nucleotides 9–11 represent an initiation codon, nucleotides 12–332 represent the SLPI coding sequence, nucleotides 333–335 represent a linking codon encoding a linking methionine residue, nucleotides 336–1517 represent the AAT coding sequence, nucleotides 1518–1520 represent a stop codon, and nucleotides 1520–1525 represent a SalI restriction site. The amino acid sequence of the SLAPI fusion protein is shown in SEQ ID NO: 8 (see Table 16), in which amino acid 1 represents an initiator methionine residue, amino acids 2–108 correspond to amino acids 1–107 of human SLPI, amino acid 109 represents a linker methionine residue and amino acids 110–503 correspond to amino acids 1–394 of human AAT.

TABLE 15

| DNA sequence used in the construction of SLAPI |
|---|
| tctagaccat gtctggaaag tctttcaagg ccggtgtttg 60 tccaccaaag aagtccgctc |
| aatgtttgag atacaagaag ccagaatgtc aatccgactg 120 gcaatgtcca ggtaagaaga |
| gatgttgtcc agacacttgt ggtatcaagt gtctagaccc 180 agttgacacc ccaaacccaa |
| ctagaagaaa gccaggtaag tgtccagtta cttacggtca 240 atgtttgatg ttgaacccac |
| caaacttctg tgaaatggac ggtcaatgta agagagactt 300 gaagtgttgt atgggtatgt |
| gtggtaagtc ctgtgtttcc ccagtcaagg ccatggaaga 360 ccctcaaggc gacgccgctc |
| aaaaaaccga caccagtcat cacgaccaag accatccgac 420 tttaataaa attactccaa |
| atttagccga atttgctttt tctttgtata gacaattagc 480 tcatcaaagt aattctacta |
| acatttttt tagtcctgtt tctattgcca ctgcttccgc 540 catgttgagt ttaggtacta |
| aagccgatac ccatgacgag attttagaag gtttaaactt 600 taatttgacc gaaatcccag |
| aagcccaaat tcacgagggt tttcaagagt tgttgagaac 660 tttgaatcaa cctgattctc |
| aattgcaatt aactactggt aacggtttat ttttgtctga 720 aggtttaaaa ttggttgaca |
| aattcctaga agacgtcaag aaactatatc atagtgaggc 780 ttttaccgtt aattttggtg |

TABLE 15-continued

| DNA sequence used in the construction of SLAPI |
|---|
| atactgagga agctaaaaag caaattaatg attatgttga 840 gaaaggcacc cagggtaaga |
| tcgttgacct agttaaagaa ttagatcgta ataccgtctt 900 cgcactagtt aactatattt |
| ttttcaaggg taagtgggaa cgtcctttcg aggttaaaga 960 tactgaagag gaagattttc |
| atgttgatca agttactact gtcaaagttc caatgatgaa 1020 aagactgggt atgttcaata |
| ttcaacattg caaaaaatta agttcttggg tcttattaat 1080 gaagtattta ggtaacgcta |
| ctgctatttt ttttttacca gacgaaggta agcttcaaca 1140 tttagagaat gagttgactc |
| atgacattat tactaaattt ttagagaacg aggatcgtcg 1200 tagcgcttct ctgcacctgc |
| caaagttaag tatcaccggt acttacgact taaaatctgt 1260 tttaggccag ttaggtatta |
| ccaaagtttt ttctaacggt gccgatttga gtggtgttac 1320 tgaagaagct ccattaaaat |
| tgagtaaagc tgttcacaaa gccgtcttaa ctattgatga 1380 aaagggtacc gaggccgccg |
| gcgctatgtt cctggaagct attccaatga gcattccacc 1440 agaagttaaa tttaataaac |
| cattcgtttt tctgatgatc gagcagaaca ctaaaagccc 1500 attgtttatg ggtaaggttg |
| tcaacccaac tcagaagtag tcgac 1525 |

TABLE 16

| Amino acid sequence of SLAPI |
|---|
| Met Ser Gly Lys Ser Phe Lys Ala Gly Val Cys Pro Pro Lys Lys Ser<br>1        5              10              15 |
| Ala Gln Cys Leu Arg Tyr Lys Lys Pro Glu Cys Gln Ser Asp Trp Gln<br>        20              25              30 |
| Cys Pro Gly Lys Lys Arg Cys Cys Pro Asp Thr Cys Gly Ile Lys Cys<br>            35          40              45 |
| Leu Asp Pro Val Asp Thr Pro Asn Pro Thr Arg Arg Lys Pro Gly Lys<br>        50              55              60 |
| Cys Pro Val Thr Tyr Gly Gln Cys Leu Met Leu Asn Pro Pro Asn Phe<br>65              70              75              80 |
| Cys Glu Met Asp Gly Gln Cys Lys Arg Asp Leu Lys Cys Cys Met Gly<br>                85              90              95 |
| Met Cys Gly Lys Ser Cys Val Ser Pro Val Lys Ala Met Glu Asp Pro<br>            100             105             110 |
| Gln Gly Asp Ala Ala Gln Lys Thr Asp Thr Ser His His Asp Gln Asp<br>            115             120             125 |

TABLE 16-continued

Amino acid sequence of SLAPI

His Pro Thr Phe Asn Lys Ile Thr Pro Asn Leu Ala Glu Phe Ala Phe
    130             135             140

Ser Leu Tyr Arg Gln Leu Ala His Gln Ser Asn Ser Thr Asn Ile Phe
145             150             155             160

Phe Ser Pro Val Ser Ile Ala Thr Ala Phe Ala Met Leu Ser Leu Gly
            165             170             175

Thr Lys Ala Asp Thr His Asp Glu Ile Leu Glu Gly Leu Asn Phe Asn
            180             185             190

Leu Thr Glu Ile Pro Glu Ala Gln Ile His Glu Gly Phe Gln Glu Leu
        195             200             205

Leu Arg Thr Leu Asn Gln Pro Asp Ser Gln Leu Gln Leu Thr Thr Gly
        210             215             220

Asn Gly Leu Phe Leu Ser Glu Gly Leu Lys Leu Val Asp Lys Phe Leu
225             230             235             240

Glu Asp Val Lys Lys Leu Tyr His Ser Glu Ala Phe Thr Val Asn Phe
            245             250             255

Gly Asp Thr Glu Glu Ala Lys Lys Gln Ile Asn Asp Tyr Val Glu Lys
            260             265             270

Gly Thr Gln Gly Lys Ile Val Asp Leu Val Lys Glu Leu Asp Arg Asp
        275             280             285

Thr Val Phe Ala Leu Val Asn Tyr Ile Phe Phe Lys Gly Lys Trp Glu
        290             295             300

Arg Pro Phe Glu Val Lys Asp Thr Glu Glu Glu Asp Phe His Val Asp
305             310             315             320

Gln Val Thr Thr Val Lys Val Pro Met Met Lys Arg Leu Gly Met Phe
            325             330             335

Asn Ile Gln His Cys Lys Lys Leu Ser Ser Trp Val Leu Leu Met Lys
            340             345             350

Tyr Leu Gly Asn Ala Thr Ala Ile Phe Phe Leu Pro Asp Glu Gly Lys
        355             360             365

Leu Gln His Leu Glu Asn Glu Leu Thr His Asp Ile Ile Thr Lys Phe
        370             375             380

Leu Glu Asn Glu Asp Arg Arg Ser Ala Ser Leu His Leu Pro Lys Leu
385             390             395             400

Ser Ile Thr Gly Thr Tyr Asp Leu Lys Ser Val Leu Gly Gln Leu Gly
            405             410             415

Ile Thr Lys Val Phe Ser Asn Gly Ala Asp Leu Ser Gly Val Thr Glu
            420             425             430

Glu Ala Pro Leu Lys Leu Ser Lys Ala Val His Lys Ala Val Leu Thr
        435             440             445

Ile Asp Glu Lys Gly Thr Glu Ala Ala Gly Ala Met Phe Leu Glu Ala
450             455             460

Ile Pro Met Ser Ile Pro Pro Glu Val Lys Phe Asn Lys Pro Phe Val
465             470             475             480

Phe Leu Met Ile Glu Gln Asn Thr Lys Ser Pro Leu Phe Met Gly Lys
            485             490             495

Val Val Asn Pro Thr Gln Lys
            500

A fusion protein comprising amino acids 1–184 of human TIMP-1 fused to amino acids 1–394 of human AAT was constructed and referred to as TAPI. The nucleotide sequence which was used in the construction of the TAPI fusion protein is shown in SEQ ID NO: 9 (see Table 17), in which nucleotides 1–6 represent an XbaI restriction site, nucleotides 6–8 represent a ribosome binding site, nucleotides 9–11 represent an initiation codon, nucleotides 12–563 represent the TIMP-1 coding sequence, nucleotides 564–566 represent a linking codon encoding a linking methionine residue, nucleotides 567–1748 represent the AAT coding sequence, nucleotides 1749–1751 represent a stop codon, and nucleotides 1751–1756 represent a SalI restriction site. The amino acid sequence of the TAPI fusion protein is shown in SEQ ID NO: 10 (see Table 18), in which amino acid 1 represents an initiator methionine residue, amino acids 2–185 correspond to amino acids 1–184 of human TIMP-1, amino acid 186 represents a linker methionine residue and amino acids 187–580 correspond to amino acids 1–394 of human AAT.

TABLE 17

DNA sequence used in the construction of TAPI

```
tctagaccat gtgcacctgt gtcccacccc acccacagac ggccttctgc aattccgacc   60
tcgtcatcag ggccaagttc gtggggacac cagaagtcaa ccagaccacc ttataccagc  120
gttatgagat caagatgacc aagatgtata aagggttcca agccttaggg gatgccgctg  180
acatccggtt cgtctacacc cccgccatgg agagtgtctg cggatacttc cacaggtccc  240
acaaccgcag cgaggagttt ctcattgctg gaaaactgca ggatggactc ttgcacatca  300
ctacctgcag tttcgtggct ccctggaaca gcctgagctt agctcagcgc cggggcttca  360
ccaagaccta cactgttggc tgtgaggaat gcacagtgtt tccctgttta tccatcccct  420
gcaaactgca gagtggcact cattgcttgt ggacggacca gctcctccaa ggctctgaaa  480
agggcttcca gtcccgtcac cttgcctgcc tgcctcggga gccagggctg tgcacctggc  540
agtccctgcg gtcccagata gccatggaag accctcaagg cgacgccgct caaaaaaccg  600
acaccagtca tcacgaccaa gaccatccga cttttaataa aattactcca aatttagccg  660
aatttgcttt ttctttgtat agacaattag ctcatcaaag taattctact aacattttt   720
ttagtcctgt ttctattgcc actgctttcg ccatgttgag tttaggtact aaagccgata  780
cccatgacga gattttagaa ggtttaaact ttaatttgac cgaaatccca gaagcccaaa  840
ttcacgaggg ttttcaagag ttgttgagaa ctttgaatca acctgattct caattgcaat  900
taactactgg taacggttta ttttttgtctg aaggtttaaa attggttgac aaattcctag  960
aagacgtcaa gaaactatat catagtgagg cttttaccgt taattttggt gatactgagg 1020
aagctaaaaa gcaaattaat gattatgttg agaaaggcac ccagggtaag atcgttgacc 1080
tagttaaaga attagatcgt gataccgtct tcgcactagt taactatatt ttttttcaagg 1140
gtaagtggga acgtcctttc gaggttaaag atactgaaga ggaagatttt catgttgatc 1200
aagttactac tgtcaaagtt ccaatgatga aaagactggg tatgttcaat attcaacatt 1260
gcaaaaaatt aagttcttgg gtcttattaa tgaagtattt aggtaacgct actgctattt 1320
ttttttttacc agacgaaggt aagcttcaac atttagagaa tgagttgact catgacatta 1380
ttactaaatt tttagagaac gaggatcgtc gtagcgcttc tctgcacctg ccaaagttaa 1440
gtatcaccgg tacttacgac ttaaaatctg ttttaggcca gttaggtatt accaaagttt 1500
tttctaacgg tgccgatttg agtggtgtta ctgaagaagc tccattaaaa ttgagtaaag 1560
ctgttcacaa agccgtctta actattgatg aaaagggtac cgaggccgcc ggcgctatgt 1620
tcctggaagc tattccaatg agcattccac cagaagttaa atttaataaa ccattcgttt 1680
ttctgatgat cgagcagaac actaaaagcc cattgtttat gggtaaggtt gtcaacccaa 1740
ctcagaagta gtcgac                                                 1756
```

TABLE 18

Amino acid sequence of TAPI

Met Cys Thr Cys Val Pro Pro His Pro Gln Thr Ala Phe Cys Asn Ser
1                5                10                    15

Asp Leu Val Ile Arg Ala Lys Phe Val Gly Thr Pro Glu Val Asn Gln
            20                25                30

Thr Thr Leu Tyr Gln Arg Tyr Glu Ile Lys Met Thr Lys Met Tyr Lys
            35                40                45

Gly Phe Gln Ala Leu Gly Asp Ala Asp Ile Arg Phe Val Tyr Thr
      50                55                60

Pro Ala Met Glu Ser Val Cys Gly Tyr Phe His Arg Ser His Asn Arg
65                70                    75                    80

Ser Glu Glu Phe Leu Ile Ala Gly Lys Leu Gln Asp Gly Leu Leu His
                  85                90                      95

Ile Thr Thr Cys Ser Phe Val Ala Pro Trp Asn Ser Leu Ser Leu Ala
              100                105              110

Gln Arg Arg Gly Phe Thr Lys Thr Tyr Thr Val Gly Cys Glu Glu Cys
          115                120                125

Thr Val Phe Pro Cys Leu Ser Ile Pro Cys Lys Leu Gln Ser Gly Thr
        130                135                140

His Cys Leu Trp Thr Asp Gln Leu Leu Gln Gly Ser Glu Lys Gly Phe
145                150                155                    160

Gln Ser Arg His Leu Ala Cys Leu Pro Arg Glu Pro Gly Leu Cys Thr
              165                170                175

Trp Gln Ser Leu Arg Ser Gln Ile Ala Met Glu Asp Pro Gln Gly Asp
            180                185                190

Ala Ala Gln Lys Thr Asp Thr Ser His His Asp Gln Asp His Pro Thr
            195                200                205

Phe Asn Lys Ile Thr Pro Asn Leu Ala Glu Phe Ala Phe Ser Leu Tyr
        210                215                220

Arg Gln Leu Ala His Gln Ser Asn Ser Thr Asn Ile Phe Phe Ser Pro
225                230                235                    240

Val Ser Ile Ala Thr Ala Phe Ala Met Leu Ser Leu Gly Thr Lys Ala
            245                250                255

Asp Thr His Asp Glu Ile Leu Glu Gly Leu Asn Phe Asn Leu Thr Glu
            260                265                270

Ile Pro Glu Ala Gln Ile His Glu Gly Phe Gln Glu Leu Leu Arg Thr
        275                280                285

Leu Asn Gln Pro Asp Ser Gln Leu Gln Leu Thr Thr Gly Asn Gly Leu
      290                295                300

Phe Leu Ser Glu Gly Leu Lys Leu Val Asp Lys Phe Leu Glu Asp Val
305                310                315                    320

Lys Lys Leu Tyr His Ser Glu Ala Phe Thr Val Asn Phe Gly Asp Thr
                325                330                335

Glu Glu Ala Lys Lys Gln Ile Asn Asp Tyr Val Glu Lys Gly Thr Gln
            340                345                350

Gly Lys Ile Val Asp Leu Val Lys Glu Leu Asp Arg Asp Thr Val Phe
        355                360                365

Ala Leu Val Asn Tyr Ile Phe Phe Lys Gly Lys Trp Glu Arg Pro Phe
      370                375                380

Glu Val Lys Asp Thr Glu Glu Glu Asp Phe His Val Asp Gln Val Thr
385                390                395                    400

Thr Val Lys Val Pro Met Met Lys Arg Leu Gly Met Phe Asn Ile Gln
            405                410                415

TABLE 18-continued

Amino acid sequence of TAPI

His Cys Lys Lys Leu Ser Ser Trp Val Leu Leu Met Lys Tyr Leu Gly
            420                 425                 430

Asn Ala Thr Ala Ile Phe Phe Leu Pro Asp Glu Gly Lys Leu Gln His
            435                 440                 445

Leu Glu Asn Glu Leu Thr His Asp Ile Ile Thr Lys Phe Leu Glu Asn
    450                 455                 460

Glu Asp Arg Arg Ser Ala Ser Leu His Leu Pro Lys Leu Ser Ile Thr
465                 470                 475                 480

Gly Thr Tyr Asp Leu Lys Ser Val Leu Gly Gln Leu Gly Ile Thr Lys
            485                 490                 495

Val Phe Ser Asn Gly Ala Asp Leu Ser Gly Val Thr Glu Glu Ala Pro
            500                 505                 510

Leu Lys Leu Ser Lys Ala Val His Lys Ala Val Leu Thr Ile Asp Glu
            515                 520                 525

Lys Gly Thr Glu Ala Ala Gly Ala Met Phe Leu Glu Ala Ile Pro Met
    530                 535                 540

Ser Ile Pro Pro Glu Val Lys Phe Asn Lys Pro Phe Val Phe Leu Met
545                 550                 555                 560

Ile Glu Gln Asn Thr Lys Ser Pro Leu Phe Met Gly Lys Val Val Asn
            565                 570                 575

Pro Thr Gln Lys
            580

Expression vectors were constructed as follows: pHG42, a vector for assembling the expression cassette for yeast expression was cloned by sequentially adding PCR cloned fragments of the *Saccharomyces cerevisiae* ADH2 promoter and terminator and the URA3 gene into pBluescript (pB1sc, Stratagene). Briefly, the ADH2 promoter was amplified with 5'-Xho and BamH1 sites, a 3'-Xba1 site and cloned into pB1sc cut with Xho1/Xba1. The ADH2 terminator was amplified with 5'-Xba1 and Sal1 sites, a 3'-Not1 site and cloned into the ADH2 promoter-containing pB1sc vector Xba1/Not1 to create pHG40. The URA3 gene was amplified with 5'-BamH1 and 3'-Xho1 sites, cloned into pHG40 to generate pHG42. Genes to be expressed were cloned into the Xba1/Sal1 sites 5'- to 3'- and the entire cassette removed as a Not1/Xho1 fragment for ligation into yeast expression vectors.

pHG62 is a yeast expression vector containing the entire *S. cerevisiae* 2 micron sequence cloned into pB1sc. The B form of 2 micron DNA was amplified by PCR from *S. cerevisiae* genomic DNA in 2 fragments as Not1/EcoR1 and EcoR1/Xho1 fragments using the unique EcoR1 site of 2 micron DNA. The entire 2 micron DNA vector was excised Not1/Xho1 for ligation and transformation yeast.

Coding sequences for the fusion proteins were constructed as follows.

Figure 3:
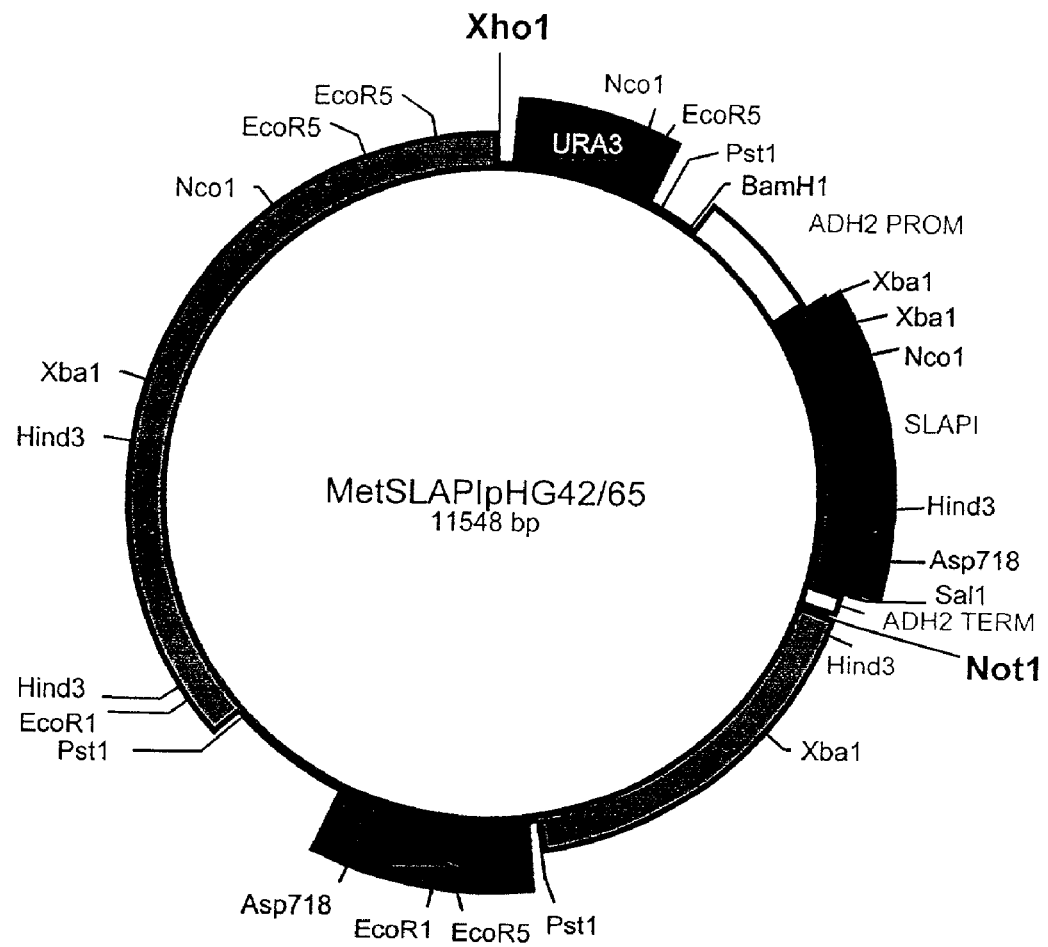
FIG. 3 is a schematic diagram of a yeast expression vector, pKC65, used to produce a SLPI/AAT fusion protein (SLAPI) in the yeast *Saccharomyces cerevisiae*.

SLAPI: A synthetic SLPI gene was chemically synthesized (Sigma Genosys) with yeast-preferred codons coding for the mature peptide, amino acids 1–107 and cloned into pUC19. PCR primers were designed with a 5'-Xba1 site and a 3'-Nco1 site to subclone SLPI as a fusion with AATyc2. A synthetic AAT gene (AATyc2) was chemically synthesized (Sigma Genosys) with yeast-preferred codons that encoded a methionine residue, and amino acids 1–394 of mature AAT, and cloned into pCR4TOPO. A three fragment ligation was assembled with pHG42 Xba1/Sal1 vector, DNA encoding SLPI as a Xba1 /Nco1 fragment and DNA encoding AATyc2 as a Nco1/Sal fragment and cloned into *E. coli* to create MetSLPI/MetAATyc2 pHG42. The Not1/Xho1 fragment of MetSLPI/MetAATyc2 pHG42 was cloned into pHG62 Not1/Xho1, pKC64 Not1/Xho1, or pKC65 Not1/Xho1. Other expression vectors which were used in the construction of SLAPI and other protease inhibitors were pKC64 and pKC 65, which are modified versions of pHG62 with the yeast LEU2 gene inserted at the novel Pst site of 2 micron DNA. A schematic diagram of the SLAPI in the pHG62 expression vector is shown in FIG. 1. A schematic diagram of the SLAPI in the pKC65 expression vector is shown in FIG. 3.

Figure 2:
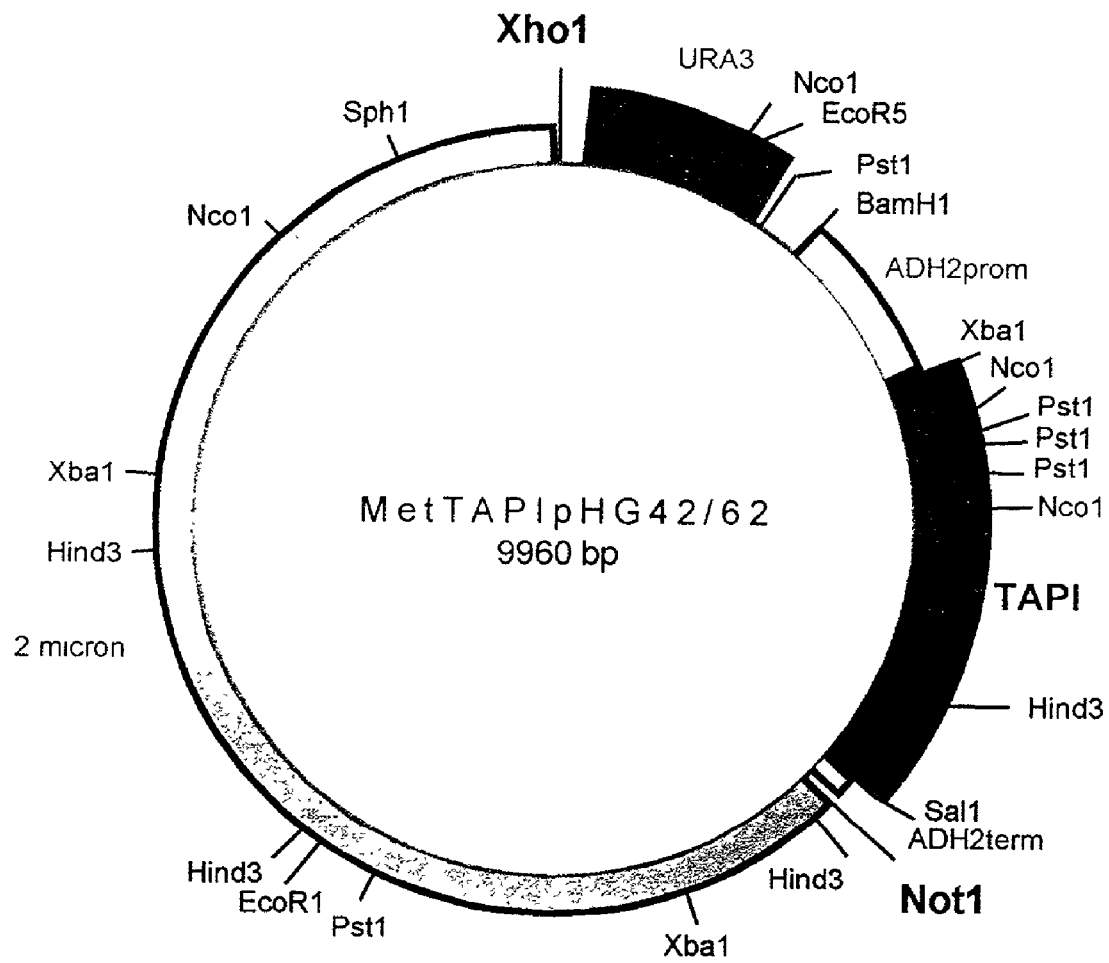
FIG. 2 is a schematic diagram of a yeast expression vector, pHG62, used to produce a TIMP-1/AAT fusion protein in the yeast *Saccharomyces cerevisiae*. The resulting expressed protein is designated TAPI.

TAPI: TIMP-1 cDNA (Docherty et al, 1985, Nature 318, 66) was cloned by PCR from human heart cDNA into pB1sc. A 5'-Xba1 site and 3'-Nco1 site were included to allow fusion of the mature peptide codons (1 –184) to the AATyc2 sequence (see SLAPI above). A three fragment ligation was assembled with pHG42 Xba1/Sal1 vector, DNA encoding TIMP-1 as a Xba1/Nco1 fragment and DNA encoding AATyc2 as a Nco1/Sal fragment and cloned into *E. coli* to create MetTIMP/MetAATyc2 pHG42. The Not1/Xho1 fragment of MetTIMP/MetAATyc2 pHG42 was cloned into pKC62 Not1/Xho1. Another expression vectors used with TAPI was pKC64 Not1/Xho1; pKC65 Not1/Xho1 is also used. A schematic diagram of the TAPI in the pHG62expression vector is shown in FIG. 2.

Example 2

Construction of N-TIMP/AAT Fusion Proteins (N-series)

The amino (NH₂ or N) terminal 126 amino acids of mature TIMP-1 have been demonstrated to contain the proteolytic inhibition domain. This domain has 6 cysteines and 3 disulfide bridges required for proper folding and activity whereas the full length molecule contains 12 cysteines and 6 disulfide bridges. To generate an active molecule with proper disulfide linkages, the N-terminal domain of TIMP has been fused to AAT to generate N-TAPI. rN-TAPI (reverse-N-TAPI) was constructed as described in the next Example. These molecules have a methionine initiation codon at aa 1 followed by the first 126 aa of human TIMP-1, another methionine followed by the 394 aa of mature human AAT (N-TAPI); or the reverse for rN-TAPI.

N-TAPI

N-TAPI is a fusion comprising amino acids 1–126 of human TIMP-1 fused to amino acids 1–394 of human AAT. The nucleotide sequence which was used in the construction of the N-TAPI fusion protein is shown in SEQ ID NO: 13 (see Table 19), in which nucleotides 1–6 represent an XbaI restriction site, nucleotides 6–8 represent a ribosome binding site, nucleotides 9–11 represent an initiation codon, nucleotides 12–389 represent the TIMP coding sequence, nucleotides 390–392 represent a linking codon encoding a linking methionine residue, nucleotides 393–1574 represent the AAT coding sequence, nucleotides 1575–1577 represent a stop codon and nucleotides 1577–1582 represent a SalI restriction site.

TABLE 19

| DNA sequence used in the construction of N-TAPI | |
|---|---|
| TCTAGACCATGTGCACCTGTGTCCCACCCCACCCACAGACGGCCTTCTGCAATTCCGACC | 60 |
| TCGTCATCAGGGCCAAGTTCGTGGGGACACCAGAAGTCAACCAGACCACCTTATACCAGC | 120 |
| GTTATGAGATCAAGATGACCAAGATGTATAAAGGGTTCCAAGCCTTAGGGGATGCCGCTG | 180 |
| ACATCCGGTTCGTCTACACCCCCGCCATGGAGAGTGTCTGCGGATACTTCCACAGGTCCC | 240 |
| ACAACCGCAGCGAGGAGTTTCTCATTGCTGGAAAACTGCAGGATGGACTCTTGCACATCA | 300 |
| CTACCTGCAGTTTCGTGGCTCCCTGGAACAGCCTGAGCTTAGCTCAGCGCCGGGCTTCA | 360 |
| CCAAGACGTATACTGTTGGCTGTGAGGAAATGGAAGACCCTCAAGGCGACGCCGCTCAAA | 420 |
| AAACCGACACCAGTCATCACGACCAAGACCATCCGACTTTTAATAAAATTACTCCAAATT | 480 |
| TAGCCGAATTTGCTTTTTCTTTGTATAGACAATTAGCTCATCAAAGTAATTCTACTAACA | 540 |
| TTTTTTTTAGTCCTGTTTCTATTGCCACTGCTTTCGCCATGTTGAGTTTAGGTACTAAAG | 600 |
| CCGATACCCATGACGAGATTTTAGAAGGTTTAAACTTTAATTTGACCGAAATCCCAGAAG | 660 |
| CCCAAATTCACGAGGGTTTTCAAGAGTTGTTGAGAACTTTGAATCAACCTGATTCTCAAT | 720 |
| TGCAATTAACTACTGGTAACGGTTTATTTTTGTCTGAAGGTTTAAAATTGGTTGACAAAT | 780 |
| TCCTAGAAGACGTCAAGAAACTATATCATAGTGAGGCTTTTACCGTTAATTTTGGTGATA | 840 |
| CTGAGGAAGCTAAAAAGCAAATTAATGATTATGTTGAGAAAGGCACCCAGGGTAAGATCG | 900 |
| TTGACCTAGTTAAAGAATTAGATCGTGATACCGTCTTCGCACTAGTTAACTATATTTTTT | 960 |
| TCAAGGGTAAGTGGGAACGTCCTTTCGAGGTTAAAGATACTGAAGAGGAAGATTTTCATG | 1020 |
| TTGATCAAGTTACTACTGTCAAAGTTCCAATGATGAAAAGACTGGGTATGTTCAATATTC | 1080 |
| AACATTGCAAAAAATTAAGTTCTTGGGTCTTATTAATGAAGTATTTAGGTAACGCTACTG | 1140 |
| CTATTTTTTTTTTACCAGACGAAGGTAAGCTTCAACATTTAGAGAATGAGTTGACTCATG | 1200 |
| ACATTATTACTAAATTTTTAGAGAACGAGGATCGTCGTAGCGCTTCTCTGCACCTGCCAA | 1260 |
| AGTTAAGTATCACCGGTACTTACGACTTAAAATCTGTTTTAGGCCAGTTAGGTATTACCA | 1320 |
| AAGTTTTTTCTAACGGTGCCGATTTGAGTGGTGTTACTGAAGAAGCTCCATTAAAATTGA | 1380 |
| GTAAAGCTGTTCACAAAGCCGTCTTAACTATTGATGAAAAGGGTACCGAGGCCGCCGGCG | 1440 |
| CTATGTTCCTGGAAGCTATTCCAATGAGCATTCCACCAGAAGTTAAATTTAATAAACCAT | 1500 |
| TCGTTTTTCTGATGATCGAGCAGAACACTAAAAGCCCATTGTTTATGGGTAAGGTTGTCA | 1560 |
| ACCCAACTCAGAAGTAGTCGAG | 1582 |

Expression vectors were as for the construction of SLAPI and TAPI, using the pKC64 Not1/Xho1 expression vector. Other vectors used in the construction of NTAPI are pHG62 and pKC65.

The coding sequences were constructed as follows. N-TIMP-1 was cloned from TIMP-1pB1sc. PCR primers were designed with a 5'-Xba1 site and 3'-BstZ17-1 site to subclone N-TIMP-1(1–127) as a fusion with AATyc2. A portion of AAT was cloned by PCR from AATyc2pCR4TOPO by PCR. PCR primers were designed with a 5'BstZ17-1 site and 3' of the unique Mfe1 site of AAT. A three fragment ligation was assembled with AATyc2pHG42 Xba1/Mfe1 vector, DNA encoding N-TIMP-1 as a Xba1/BstZ17-1 fragment and DNA encoding AATyc2 as a BstZ17-1/Mfe1 fragment and cloned into E. coli to create MetN-TIMP-1/MetAATyc2 pHG42. The Not1/Xho1 fragment of MetN-TIMP-1/MetAATyc2 pHG42 was cloned into pkC64 Not1/Xho1 or pHG62. The amino acid sequence of N-TAPI is shown in SEQ ID NO: 14 (see Table 20), in which amino acid 1 corresponds to an initiator methionine residue, amino acids 2–127 represent amino acids 1–126 of human TIMP-1, amino acid 128 is a linking methionine, and amino acids 129–522 represent amino acids 1–394 of human AAT.

TABLE 20

Amino acid sequence of N-TAPI

MCTCVPPHPQTAFCNSDLVIRAKFVGTPEVNQTTLYQRYEIKMTKMY 60
KGFQALGDAADIR

FVYTPAMESVCGYFHRSHNRSEEFLIAGKLQDGLLHITTCSFVAPWN 120
SLSLAQRRGFTKT

YTVGCEE-M-EDPQGDAAQKTDTSHHDQDHPTFNKITPNLAEFAFSL 180
YRQLAHQSNSTNI

FFSPVSIATAFAMLSLGTKADTHDEILEGLNFNLTEIPEAQIHEGFQ 238
ELLRTLNQPDSQL

QLTTGNGLFLSEGLKLVDKFLEDVKKLYHSEAFTVNFGDTEEAKKQI 298
NDYVEKGTQGKIV

DLVKELDRDTVFALVNYIFFKGKWERPFEVKDTEEEDFHVDQVTTVK 358
VPMMKRLGMFNIQ

HCKKLSSWVLLMKYLGNATAIFFLPDEGKLQHLENELTHDIITKFLE 418
NEDRRSASLHLPK

LSITGTYDLKSVLGQLGITKVFSNGADLSGVTEEAPLKLSKAVHKAV 478
LTIDEKGTEAAGA

MFLEAIPMSIPPEVKFNKPFVFLMIEQNTKSPLFMGKVVNPTQK 522

Example 3

Reverse Orientation Fusion Proteins

The r series of proteins, here rSLAPI, rTAPI, and rN-TAPI, are fusion proteins designed with AAT at the amino terminal end of the protein with either SLPI, TIMP, or N-TIMP-1 following at the carboxyl end of the protein, and a methionine inserted at the junction between the two proteins. Thus, following the initiation methionine at amino acid 1 there are the 394 amino acids of mature human AAT, another methionine and then 107 and 184 amino acids respectively for mature human SLPI and human TIMP-1, or amino acids 1–126 of N-TIMP-127.

Construction of rSLAPI rSLAPI, a fusion of AATyc2 plus SLPI (aa 1–107), is the reverse of SLAPI. The coding regions are fused with a novel BspE1 site inserted by PCR into the first 2 aa of SLPI as follows. A 3 piece ligation is assembled in AATyc2pHG42#3 Hindlll/Sal1 vector with Hindlll/BspE1 AAT fragment and BspE1/Sal1 SLPI fragment. The Not1/Xho1 fragment is ligated in to the yeast vector pKC64. pHG 62 or pKC65 are also used as expression vectors.

The DNA sequence used in the construction of r-SLAPI is shown in SEQ ID NO: 15 (Table 21), in which nucleotides 1–6 represent an XbaI restriction site, nucleotides 6–8 represent a ribosome binding site, nucleotides 9–11 represent an initiation codon, nucleotides 12–1193 represent the coding sequence for amino acids 1–394 of AAT, nucleotides 1194–1196 represent a linking codon encoding a linking methionine residue, nucleotides 1197–1517 represent the SLPI coding sequence, nucleotides 1578–1520 represent a stop codon and nucleotides 1520–1525 represent a SalI restriction site.

TABLE 21

DNA sequence used in the construction of rSLAPI

TCTAGACCATGGAAGACCCTCAAGGCGACGCCGCTCAAAAAACCG 60
ACACCAGTCATCACG

ACCAAGACCATCCGACTTTTAATAAAATTACTCCAAATTTAGCCG 120
AATTTGCTTTTTCTT

TGTATAGACAATTAGCTCATCAAAGTAATTCTACTAACATTTTTT 180
TTAGTCCTGTTTCTA

TTGCCACTGCTTTCGCCATGTTGAGTTTAGGTACTAAAGCCGATA 240
CCCATGACGAGATTT

TAGAAGGTTTAAACTTTAATTTGACCGAAATCCCAGAAGCCCAAA 300
TTCACGAGGGTTTTC

AAGAGTTGTTGAGAACTTTGAATCAACCTGATTCTCAATTGCAAT 360
TAACTACTGGTAACG

GTTTATTTTTGTCTGAAGGTTTAAAATTGGTTGACAAATTCCTAG 420
AAGACGTCAAGAAAC

TATATCATAGTGAGGCTTTTACCGTTAATTTTGGTGATACTGAGG 480
AAGCTAAAAAGCAAA

TTAATGATTATGTTGAGAAAGGCACCCAGGGTAAGATCGTTGACC 540
TAGTTAAAGAATTAG

ATCGTGATACCGTCTTCGCACTAGTTAACTATATTTTTTCAAGG 600
GTAAGTGGGAACGTC

CTTTCGAGGTTAAAGATACTGAAGAGGAAGATTTTCATGTTGATC 660
AAGTTACTACTGTCA

AAGTTCCAATGATGAAAAGACTGGGTATGTTCAATATTCAACATT 720
GCAAAAAATTAAGTT

CTTGGGTCTTATTAATGAAGTATTTAGGTAACGCTACTGCTATTT 780
TTTTTTTACCAGACG

AAGGTAAGCTTCAACATTTAGAGAATGAGTTGACTCATGACATTA 840
TTACTAAATTTTTAG

AGAACGAGGATCGTCGTAGCGCTTCTCTGCACCTGCCAAAGTTAA 900
GTATCACCGGTACTT

ACGACTTAAAATCTGTTTTAGGCCAGTTAGGTATTACCAAAGTTT 960
TTTCTAACGGTGCCG

ATTTGAGTGGTGTTACTGAAGAAGCTCCATTAAAAATTGAGTAAAG 1020
CTGTTCACAAAGCCG

TABLE 21-continued

DNA sequence used in the construction of rSLAPI

| | |
|---|---|
| TCTTAACTATTGATGAAAAGGGTACCGAGGCCGCCGGCGCTATGT | 1080 |
| TCCTGGAAGCTATTC | |
| CAATGAGCATTCCACCAGAAGTTAAATTTAATAAACCATTCGTTT | 1140 |
| TTCTGATGATCGAGC | |
| AGAACACTAAAAGCCCATTGTTTATGGGTAAGGTTGTCAACCCAA | 1200 |
| CTCAGAAGATGTCCG | |
| GAAAGTCTTTCAAGGCCGGTGTTTGTCCACCAAAGAAGTCCGCTC | 1260 |
| AATGTTTGAGATACA | |
| AGAAGCCAGAATGTCAATCCGACTGGCAATGTCCAGGTAAGAAGA | 1320 |
| GATGTTGTCCAGACA | |
| CTTGTGGTATCAAGTGTCTAGACCCAGTTGACACCCAAACCCAA | 1380 |
| CTAGAAGAAAGCCAG | |
| GTAAGTGTCCAGTTACTTACGGTCAATGTTTGATGTTGAACCCAC | 1440 |
| CAAACTTCTGTGAAA | |
| TGGACGGTCAATGTAAGAGAGACTTGAAGTGTTGTATGGGTATGT | 1500 |
| GTGGTAAGTCCTGTG | |
| TTTCCCCAGTCAAGGCCTAGTCGAC | 1525 |

The amino acid sequence for r-SLAPI is shown in SEQ ID NO: 16 (Table 22), in which in which amino acid 1 corresponds to an initiator methionine residue, amino acids 2–395 represent amino acids 1–394 of human AAT, amino acid 396 is a linking methionine, and amino acids 397–503 represent amino acids 1–107 of human AAT.

TABLE 22

Amino acid sequence of rSLAPI

| | |
|---|---|
| MEDPQGDAAQKTDTSHHDQDHPTFNKITPNLAEFAFSLYRQLAHQSN | 60 |
| STNIFFSPVSIAT | |
| AFAMLSLGTKADTHDEILEGLNFNLTEIPEAQIHEGFQELLRTLNQP | 120 |
| DSQLQLTTGNGLF | |
| LSEGLKLVDKFLEDVKKLYHSEAFTVNFGDTEEAKKQINDYVEKGTQ | 180 |
| GKIVDLVKELDRD | |
| TVFALVNYIFFKGKWERPFEVKDTEEEDFHVDQVTTVKVPMMKRLGM | 240 |
| FNIQHCKKLSSWV | |
| LLMKYLGNATAIFFLPDEGKLQHLENELTHDIITKFLENEDRRSASL | 300 |
| HLPKLSITGTYDL | |
| KSVLGQLGITKVFSNGADLSGVTEEAPLKLSKAVHKAVLTIDEKGTE | 360 |
| AAGAMFLEAIPMS | |
| IPPEVKFNKPFVFLMIEQNTKSPLFMGKVVNPTQK-M-SGKSFKAGV | 418 |
| CPPKKSAQCLRYK | |
| KPECQSDWQCPGKKRCCPDTCGIKCLDPVDTPNPTRRKPGKCPVTYG | 478 |
| QCLMLNPPNFCEM | |
| DGQCKRDLKCCMGMCGKSCVSPVKA | 503 |

Figure 4:
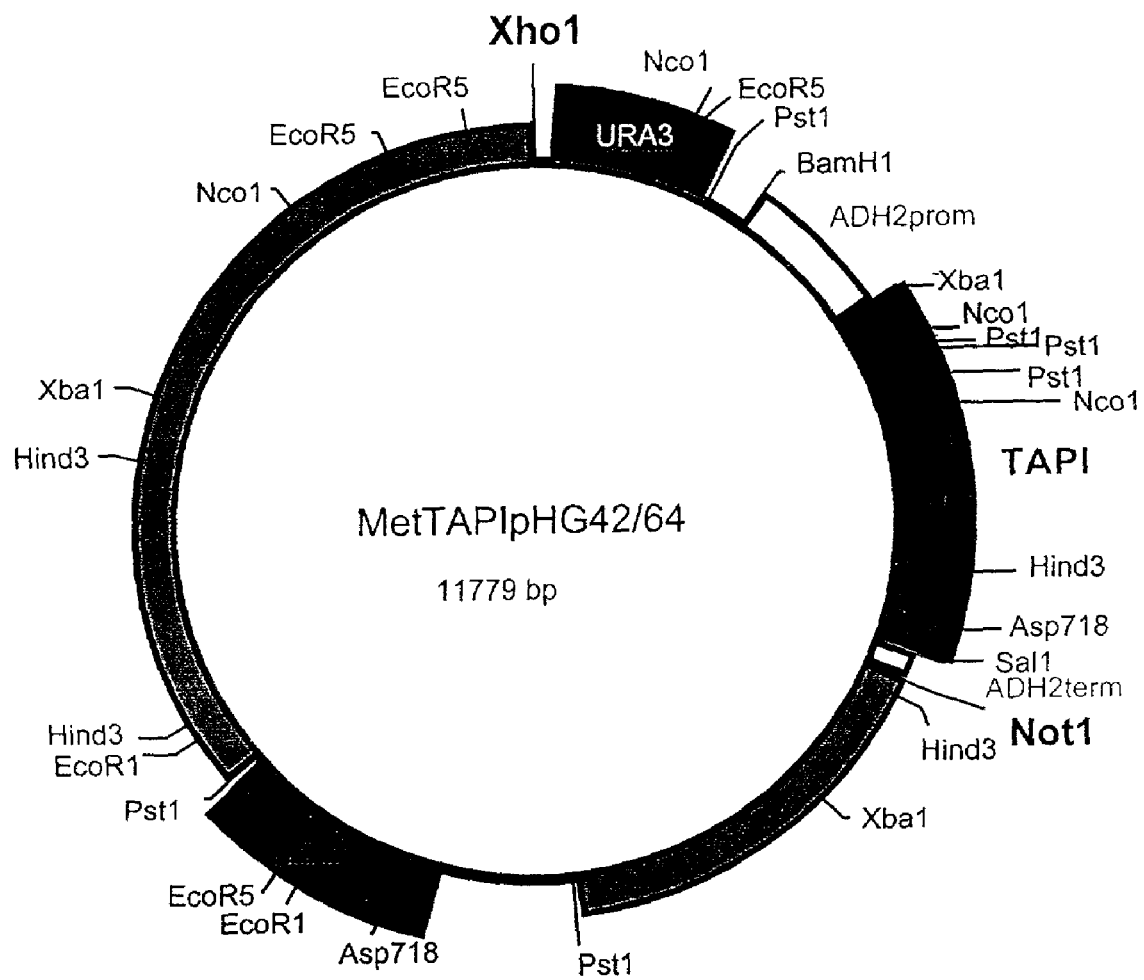
FIG. 4 is a schematic diagram of a yeast expression vector, pKC64, used to produce an AAT/TIMP-1 fusion protein in the yeast *Saccharomyces cerevisiae*. The resulting expressed protease inhibitor is designated reverse (r) TAPI.

Construction of rTAPI rTAPI, a fusion of AAT plus TIMP-1 (aa 1–184), is the reverse of TAPI. The coding regions were fused with a novel PmlI site inserted by PCR into the first 3 amino acids of TIMP-1 as follows. A 3 piece ligation was assembled with HindIII/SalI vector pB1sc, DNA encoding 3'AAT as a HindIII/PmlI fragment and DNA encoding TIMP-1 as a PmlI/SalI fragment. The 3'AAT/TIMP-1 fusion HindIII/SalI fragment was subcloned into AATyc2 pHG42 HindIII/SalI. rTAPI was expressed in the yeast vector pKC64 as a NotI/XhoI fragment as for r-SLAPI. A schematic diagram of the rTAPI expression vector pKC64 is shown in FIG. 4. Other vectors used for rTAPI are pHG62 and pKC65.

The DNA sequence which was used in the construction of r-TAPI is shown in SEQ ID NO: 17 (Table 23), in which nucleotides 1–6 represent an XbaI restriction site, nucleotides 6–8 represent a ribosome binding site, nucleotides 9–11 represent an initiation codon, nucleotides 12–1193 represent the coding sequence for amino acids 1–394 of human AAT, nucleotides 1194–1196 represent a codon encoding a linking methionine residue, nucleotides 1197–1748 represent codons for amino acids 1–184 of human TIMP-1, nucleotides 1749–1751 represent a stop codon and nucleotides 1751–1756 represent a SalI restriction site.

TABLE 23

DNA sequence used in the construction of rTAPI

| | |
|---|---|
| TCTAGACCATGGAAGACCCTCAAGGCGACGCCGCTCAAAAAACCG | 60 |
| ACACCAGTCATCACG | |
| ACCAAGACCATCCGACTTTTAATAAAATTACTCCAAATTTAGCCG | 120 |
| AATTTGCTTTTTCTT | |
| TGTATAGACAATTAGCTCATCAAAGTAATTCTACTAACATTTTTT | 180 |
| TTAGTCCTGTTTCTA | |
| TTGCCACTGCTTTCGCCATGTTGAGTTTAGGTACTAAAGCCGATA | 240 |
| CCCATGACGAGATTT | |
| TAGAAGGTTTAAACTTTAATTTGACCGAAATCCCAGAAGCCCAAA | 300 |
| TTCACGAGGGTTTTC | |
| AAGAGTTGTTGAGAACTTTGAATCAACCTGATTCTCAATTGCAAT | 360 |
| TAACTACTGGTAACG | |
| GTTTATTTTTGTCTGAAGGTTTAAAATTGGTTGACAAATTCCTAG | 420 |
| AAGACGTCAAGAAAC | |
| TATATCATAGTGAGGCTTTTACCGTTAATTTTGGTGATACTGAGG | 480 |
| AAGCTAAAAAGCAAA | |
| TTAATGATTATGTTGAGAAAGGCACCCAGGGTAAGATCGTTGACC | 540 |
| TAGTTAAAGAATTAG | |
| ATCGTGATACCGTCTTCGCACTAGTTAACTATATTTTTTTCAAGG | 600 |
| GTAAGTGGGAACGTC | |
| CTTTCGAGGTTAAAGATACTGAAGAGGAAGATTTTCATGTTGATC | 660 |
| AAGTTACTACTGTCA | |
| AAGTTCCAATGATGAAAAGACTGGGTATGTTCAATATTCAACATT | 720 |
| GCAAAAAATTAAGTT | |
| CTTGGGTCTTATTAATGAAGTATTTAGGTAACGCTACTGCTATTT | 780 |
| TTTTTTTACCAGACG | |
| AAGGTAAGCTTCAACATTTAGAGAATGAGTTGACTCATGACATTA | 840 |
| TTACTAAATTTTTAG | |
| AGAACGAGGATCGTCGTAGCGCTTCTCTGCACCTGCCAAAGTTAA | 900 |
| GTATCACCGGTACTT | |
| ACGACTTAAAATCTGTTTTAGGCCAGTTAGGTATTACCAAAGTTT | 960 |
| TTTCTAACGGTGCCG | |
| ATTTGAGTGGTGTTACTGAAGAAGCTCCATTAAAATTGAGTAAAG | 1020 |
| CTGTTCACAAAGCCG | |
| TCTTAACTATTGATGAAAAGGGTACCGAGGCCGCCGGCGCTATGT | 1080 |
| TCCTGGAAGCTATTC | |

TABLE 23-continued

DNA sequence used in the construction of rTAPI

CAATGAGCATTCCACCAGAAGTTAAATTTAATAAACCATTCGTTT  1140
TTCTGATGATCGAGC

AGAACACTAAAAGCCCATTGTTTATGGGTAAGGTTGTCAACCCAA  1200
CTCAGAAGATGTGCA

CGTGTGTCCCACCCCACCCACAGACGGCCTTCTGCAATTCCGACC  1260
TCGTCATCAGGGCCA

AGTTCGTGGGGACACCAGAAGTCAACCAGACCACCTTATACCAGC  1320
GTTATGAGATCAAGA

TGACCAAGATGTATAAAGGGTTCCAAGCCTTAGGGGATGCCGCTG  1380
ACATCCGGTTCGTCT

ACACCCCGCCATGGAGAGTGTCTGCGGATACTTCCACAGGTCCC  1440
ACAACCGCAGCGAGG

AGTTTCTCATTGCTGGAAAACTGCAGGATGGACTCTTGCACATCA  1500
CTACCTGCAGTTTCG

TGGCTCCCTGGAACAGCCTGAGCTTAGCTCAGCGCCGGGGCTTCA  1560
CCAAGACCTACACTG

TTGGCTGTGAGGAATGCACAGTGTTTCCCTGTTTATCCATCCCT  1620
GCAAACTGCAGAGTG

GCACTCATTGCTTGTGGACGGACCAGCTCCTCCAAGGCTCTGAAA  1680
AGGGCTTCCAGTCCC

GTCACCTTGCCTGCCTGCCTCGGGAGCCAGGGCTGTGCACCTGGC  1740
AGTCCCTGCGGTCCC

AGATAGCCTAGTCGAC  1756

The amino acid sequence for R-TAPI is shown in SEQ ID NO: 18 (see Table 24), in which in which amino acid 1 corresponds to an initiator methionine residue, amino acids 2–395 represent amino acids 1–394 of human AAT, amino acid 396 is a linking methionine, and amino acids 397–580 represent amino acids 1–184 of human TIMP-1.

TABLE 24

Amino acid sequence of rTAPI

MEDPQGDAAQKTDTSHHDQDHPTFNKITPNLAEFAFSLYRQLAHQSN  60
STNIFFSPVSIAT

AFAMLSLGTKADTHDEILEGLNFNLTEIPEAQIHEGFQELLRTLNQP  120
DSQLQLTTGNGLF

LSEGLKLVDKFLEDVKKLYHSEAFTVNFGDTEEAKKQINDYVEKGTQ  180
GKIVDLVKELDRD

TVFALVNYIFFKGKWERPFEVKDTEEEDFHVDQVTTVKVPMMKRLGM  240
FNIQHCKKLSSWV

LLMKYLGNATAIFFLPDEGKLQHLENELTHDIITKFLENEDRRSASL  300
HLPKLSITGTYDL

KSVLGQLGITKVFSNGADLSGVTEEAPLKLSKAVHKAVLTIDEKGTE  360
AAGAMFLEAIPMS

IPPEVKFNKPFVFLMIEQNTKSPLFMGKVVNPTQK-M-CTCVPPHPQ  418
TAFCNSDLVIRAK

FVGTPEVNQTTLYQRYEIKMTKMYKGFQALGDAADIRFVYTPAMESV  478
CGYFHRSHNRSEE

FLIAGKLQDGLLHITTCSFVAPWNSLSLAQRRGFTKTYTVGCEECTV  538
FPCLSIPCKLQSG

THCLWTDQLLQGSEKGFQSRHLACLPREPGLCTWQSLRSQIA  580

Construction of rN-TAPI rN-TAPI, a fusion of AAT plus N-TIMP-127 (aa 1–126 of N-TIMP, with a leading methionine), is the reverse of N-TAPI. The coding regions were fused with a novel Pml1 site inserted by PCR into the first 3 aa of TIMP-1 as follows. A ligation was assembled in rTAP12pHG42 Pml1/Sal1 vector with Pml1/Sal1 N-TIMP1 fragment. The Not1/Xho1 fragment was ligated into the yeast vector pKC64. Other vectors used for rNTAPI are pHG62 and pKC65.

The DNA sequence which was used in the construction of rN-TAPI is shown in SEQ ID NO: 19 (see Table 25), in which nucleotides 1–6 represent an XbaI restriction site, nucleotides 6–8 represent a ribosome binding site, nucleotides 9–11 represent an initiation codon, nucleotides 12–1193 represent the coding sequence for amino acids 1–394 of human AAT, nucleotides 1194–1196 represent a codon encoding a linking methionine residue, nucleotides 1197–1574 represent codons for amino acids 1–126 of human TIMP-1, nucleotides 1575–1577 represent a stop codon and nucleotides 1577–1582 represent a SalI restriction site.

TABLE 25

DNA sequence used in the construction of rN-TAPI

TCTAGACCATGGAAGACCCTCAAGGCGACGCCGCTCAAAAAACCG  60
ACACCAGTCATCACG

ACCAAGACCATCCGACTTTTAATAAAATTACTCCAAATTTAGCCG  120
AATTTGCTTTTTCTT

TGTATAGACAATTAGCTCATCAAAGTAATTCTACTAACATTTTTT  180
TTAGTCCTGTTTCTA

TTGCCACTGCTTTCGCCATGTTGAGTTTAGGTACTAAAGCCGATA  240
CCCATGACGAGATTT

TAGAAGGTTTAAACTTTAATTTGACCGAAATCCCAGAAGCCCAAA  300
TTCACGAGGGTTTTC

AAGAGTTGTTGAGAACTTTGAATCAACCTGATTCTCAATTGCAAT  360
TAACTACTGGTAACG

GTTTATTTTGTCTGAAGGTTTAAAATTGGTTGACAAATTCCTAG  420
AAGACGTCAAGAAAC

TATATCATAGTGAGGCTTTTACCGTTAATTTTGGTGATACTGAGG  480
AAGCTAAAAAGCAAA

TTAATGATTATGTTGAGAAAGGCACCCAGGGTAAGATCGTTGACC  540
TAGTTAAAGAATTAG

ATCGTGATACCGTCTTCGCACTAGTTAACTATATTTTTTTCAAGG  600
GTAAGTGGGAACGTC

CTTTCGAGGTTAAAGATACTGAAGAGGAAGATTTTCATGTTGATC  660
AAGTTACTACTGTCA

AAGTTCCAATGATGAAAAGACTGGGTATGTTCAATATTCAACATT  720
GCAAAAAATTAAGTT

CTTGGGTCTTATTAATGAAGTATTTAGGTAACGCTACTGCTATTT  780
TTTTTTTACCAGACG

AAGGTAAGCTTCAACATTTAGAGAATGAGTTGACTCATGACATTA  840
TTACTAAATTTTTAG

AGAACGAGGATCGTCGTAGCGCTTCTCTGCACCTGCCAAAGTTAA  900
GTATCACCGGTACTT

ACGACTTAAAATCTGTTTTAGGCCAGTTAGGTATTACCAAAGTTT  960
TTTCTAACGGTGCCG

ATTTGAGTGGTGTTACTGAAGAAGCTCCATTAAAATTGAGTAAAG  1020
CTGTTCACAAAGCCG

TABLE 25-continued

DNA sequence used in the construction of rN-TAPI

| | |
|---|---|
| TCTTAACTATTGATGAAAAGGGTACCGAGGCCGCCGGCGCTATGT TCCTGGAAGCTATTC | 1080 |
| CAATGAGCATTCCACCAGAAGTTAAATTTAATAAACCATTCGTTT TTCTGATGATCGAGC | 1140 |
| AGAACACTAAAAGCCCATTGTTTATGGGTAAGGTTGTCAACCCAA CTCAGAAGATGTGCA | 1200 |
| CGTGTGTCCCACCCCACCCACAGACGGCCTTCTGCAATTCCGACC TCGTCATCAGGGCCA | 1260 |
| AGTTCGTGGGGACACCAGAAGTCAACCAGACCACCTTATACCAGC GTTATGAGATCAAGA | 1320 |
| TGACCAAGATGTATAAAGGGTTCCAAGCCTTAGGGGATGCCGCTG ACATCCGGTTCGTCT | 1380 |
| ACACCCCCGCCATGGAGAGTGTCTGCGGATACTTCCACAGGTCCC ACAACCGCAGCGAGG | 1440 |
| AGTTTCTCATTGCTGGAAAACTGCAGGATGGACTCTTGCACATCA CTACCTGCAGTTTCG | 1500 |
| TGGCTCCCTGGAACAGCCTGAGCTTAGCTCAGCGCCGGGCTTCA CCAAGACCTACACTG | 1560 |
| TTGGCTGTGAGGAATAGTCGAC | 1582 |

The amino acid sequence for RN-TAPI is shown in SEQ ID NO: 20 (see Table 26), in which amino acid 1 corresponds to an initiator methionine residue, amino acids 2–395 represent amino acids 1–394 of human AAT, amino acid 396 is a linking methionine, and amino acids 397–522 represent amino acids 1–126 of human TIMP-1.

TABLE 26

Amino acid sequence of rN-TAPI

| | |
|---|---|
| MEDPQGDAAQKTDTSHHDQDHPTFNKITPNLAEFAFSLYRQLAHQSN STNIFFSPVSIAT | 60 |
| AFAMLSLGTKADTHDEILEGLNFNLTEIPEAQIHEGFQELLRTLNQP DSQLQLTTGNGLF | 120 |
| LSEGLKLVDKFLEDVKKLYHSEAFTVNFGDTEEAKKQINDYVEKGTQ GKIVDLVKELDRD | 180 |
| TVFALVNYIFFKGKWERPFEVKDTEEEDFHVDQVTTVKVPMMKRLGM FNIQHCKKLSSWV | 240 |
| LLMKYLGNATAIFFLPDEGKLQHLENELTHDIITKFLENEDRRSASL HLPKLSITGTYDL | 300 |
| KSVLGQLGITKVFSNGADLSGVTEEAPLKLSKAVHKAVLTIDEKGTE AAGAMFLEAIPMS | 360 |
| IPPEVKFNKPFVFLMIEQNTKSPLFMGKVVNPTQK-M-CTCVPPHPQ TAFCNSDLVIRAK | 418 |
| FVGTPEVNQTTLYQRYEIKMTKMYKGFQALGDAADIRFVYTPAMESV CGYFHRSHNRSEE | 478 |
| FLIAGKLQDGLLHITTCSFVAPWNSLSLAQRRGFTKTYTVGCEE | 522 |

Example 4

S-Linked TAPI

Another method of creating the fusion protein is by expressing N-TIMP 1–128 (Met at aa 1 plus 127 aa of mature TIMP) which contains an additional native cysteine at the carboxyl terminus (aa 128) which is free to form a disulfide bridge with a free cysteine in AAT; e.g. the single free cysteine of AAT (at position 232, see SEQ ID NO: 2). Methods of formation of intra- and intermolecular disulfide bonds are known in the art. N-TIMP 1–127, which lacks C-terminal cysteine of N-TIMP 1–128, was constructed as well. N-TIMP 1–127 serves as a positive control in assays with N-TIMP 1–128. Both N-TIMP 1–127 and N-TIMP 1–128 are useful in fusion proteins with other protease inhibitors besides AAT. N-TIMP 1–128 is useful because of its terminal cysteine, allowing reaction at the thiol group for, e.g., disulfide bridge formation with another peptide chain.

N-TIMP 1–127

N-TIMP 1–127 was assembled as 5'Xba1 and 3'Sal1 PCR fragments from TIMP-1pB1sc in pHG42 Xba/Sal vector. The DNA sequence used in the construction of N-TIMP 1–127 is shown in SEQ ID NO: 21 (Table 27), in which nucleotides 1–6 represent an XbaI restriction site, nucleotides 6–8 represent a ribosome binding site, nucleotides 9–11 represent an initiation codon, nucleotides 12–389 represent the coding sequence for amino acids 1–126 of TIMP, nucleotides 390–392 represent a stop codon and nucleotides 392–397 represent a SalI restriction site.

TABLE 27

DNA sequence used in the construction of N-TIMP 1–127

| | |
|---|---|
| TCTAGACCATGTGCACCTGTGTCCCACCCCACCCACAGACGGCCTTC TGCAATTCCGACC | 60 |
| TCGTCATCAGGGCCAAGTTCGTGGGGACACCAGAAGTCAACCAGACC ACCTTATACCAGC | 120 |
| GTTATGAGATCAAGATGACCAAGATGTATAAAGGGTTCCAAGCCTTA GGGGATGCCGCTG | 180 |
| ACATCCGGTTCGTCTACACCCCCGCCATGGAGAGTGTCTGCGGATAC TTCCACAGGTCCC | 240 |
| ACAACCGCAGCGAGGAGTTTCTCATTGCTGGAAAACTGCAGGATGGA CTCTTGCACATCA | 300 |
| CTACCTGCAGTTTCGTGGCTCCCTGGAACAGCCTGAGCTTAGCTCAG CGCCGGGCTTCA | 360 |
| CCAAGACGTATACTGTTGGCTGTGAGGAATAGTCGAC | 397 |

The amino acid sequence used in constructs containing N-TIMP 1–127 is shown in SEQ ID NO: 22 (see Table 28), in which amino acid 1 corresponds to an initiator methionine residue, and amino acids 2–127 represent amino acids 1–126 of human TIMP-1. The construct was cloned as Not1/Xho1 fragments into pKC64 Not1/Xho1 vector. Other vectors used for this construct are pHG62 and pKC65.

TABLE 28

Amino acid sequence of N-TIMP 1–127

| | |
|---|---|
| MCTCVPPHPQTAFCNSDLVIRAKFVGTPEVNQTTLYQRYEIKMTKMY KGFQALGDAADIR | 60 |
| FVYTPAMESVCGYFHRSHNRSEEFLIAGKLQDGLLHITTCSFVAPWN SLSLAQRRGFTKT | 120 |
| YTVGCEE | |

N-TIMP 1–128

N-TIMP 1–128 is assembled as 5'Xba1 and 3'Sal1 PCR fragments from TIMP-1pB1sc in pHG42 Xba/Sal vector.

The DNA sequence used in the construction of N-TIMP 1–128 is shown in SEQ ID NO: 23 (see Table 29), in which nucleotides 1–6 represent an XbaI restriction site, nucleotides 6–8 represent a ribosome binding site, nucleotides 9–11 represent an initiation codon, nucleotides 12–392 represent the coding sequence for amino acids 1–127 of TIMP, nucleotides 393–395 represent a stop codon and nucleotides 395–400 represent a SalI restriction site.

TABLE 29

N-TIMP 1–128 DNA sequence

TCTAGACCATGTGCACCTGTGTCCCACCCCACCCACAGACGGCCTTC 60
TGCAATTCCGACC

TCGTCATCAGGGCCAAGTTCGTGGGGACACCAGAAGTCAACCAGACC 120
ACCTTATACCAGC

GTTATGAGATCAAGATGACCAAGATGTATAAAGGGTTCCAAGCCTTA 180
GGGGATGCCGCTG

ACATCCGGTTCGTCTACACCCCCGCCATGGAGAGTGTCTGCGGATAC 240
TTCCACAGGTCCC

ACAACCGCAGCGAGGAGTTTCTCATTGCTGGAAAACTGCAGGATGGA 300
CTCTTGCACATCA

CTACCTGCAGTTTCGTGGCTCCCTGGAACAGCCTGAGCTTAGCTCAG 360
CGCCGGGGCTTCA

CCAAGACGTATACTGTTGGCTGTGAGGAATGCTAGTCGAC 400

The amino acid sequence of N-TIMP 1–128 is shown in SEQ ID NO: 24 (see Table 30), in which amino acid 1 corresponds to an initiator methionine residue, and amino acids 2–128 represent amino acids 1–127 of human TIMP-1.

TABLE 30

Amino acid sequence of N-TIMP 1–128

MCTCVPPHPQTAFCNSDLVIRAKFVGTPEVNQTTLYQRYEIKMTKMY 60
KGFQALGDAADIR

FVYTPAMESVCGYFHRSHNRSEEFLIAGKLQDGLLHITTCSFVAPWN 120
SLSLAQRRGFTKT

YTVGCEEC

N-TIMP 1–128 contains an additional native cysteine at the carboxyl terminus (aa 128) which is free to form a disulfide bridge with a cysteine of AAT; e.g., the single free cysteine of AAT (at position 232, see SEQ ID NO: 2). The construct is cloned as Not1/Xho1 fragments into pKC64 Not1/Xho1 vector. Other vectors used for this construct are pHG62 and pKC65. The construction of the DNA for the N-TIMP 1–128 is described in Example 2, and its DNA sequence is shown in Table 29. The amino acid sequence of N-TIMP 1–128 is shown in Table 30.

Example 5

Expression in Yeast of a Recombinant SLPI/AAT Fusion Protein

A fusion protein of SLPI and AAT (designated SLAPI, the DNA and amino acid sequence of which are shown in SEQ ID NOS: 7 and 8, respectively, prepared as described in Example 1, and AAT alone, were expressed intracellularly in a yeast vector containing the following components: The ADH2 promoter and terminator drive the expression of the recombinant protein and the URA3 gene provides a selectable marker for growth of yeast in uracil-deficient media. The yeast 2 micron sequences are required for autonomous replication of the vector in yeast. Yeast transformants harboring these plasmids were grown in YEPD medium and cell lysates were analyzed for total protein, AAT concentration by capture ELISA, and elastase inhibitory activity.

Table 31, below, shows the results of AAT and SLAPI cultures grown in 2 YEPD-based media, Difco and Red Star. Assuming the ELISA is capable of quantitating the AAT alone or as a fusion partner, the specific activity, units of anti-elastase activity per mg AAT/SLAPI, allows a direct comparison of proteins expressed at different levels in a crude lysate.

TABLE 31

Anti-elastase activities of AAT and SLAPI

| Protein/Medium | Protein concentration, mg/ml lysate | Activity, units/ml lysate | Activity, units/mg protein | AAT concentration, ELISA, mg AAT/ml | Specific activity, units/mg AAT |
|---|---|---|---|---|---|
| AAT/Difco | 4.69 | 0.459 | 0.098 | 0.714 | 0.643 |
| SLAPI/Difco | 5.42 | 0.208 | 0.038 | 0.161 | 1.292 |
| AAT/Red Star | 3.62 | 0.245 | 0.068 | 0.315 | 0.778 |
| SLAPI/Red Star | 5.63 | 0.191 | 0.034 | 0.130 | 1.469 |

Both AAT and SLAPI have detectable anti-elastase activity and specific AAT production in crude lysates. While the expression levels varied for each molecule in various media, the specific activity for SLAPI was shown to be 2.0- and 1.9-fold higher than AAT in Difco and Red Star medium, respectively. These results show that the SLAPI fusion protein has double the specific activity of AAT, indicating that the SLPI and AAT halves of the molecule each exhibit inhibitory activity against elastase.

Example 6

Assay for AAT Activity Using Porcine Pancreatic Elastase

Definitions/Abbreviations rAAT: recombinant alpha 1-antitrypsin, BSA: bovine serum albumin, DMSO: dimethyl sulfoxide, OD: optical density, PPE: porcine pancreatic elastase, % CV: coefficient of variation (100×standard deviation÷mean, as %).

Materials and Equipment

Multi-channel pipettor; BioHit Proline or Eppendorf, 5–100 μL. Multi-channel pipettor; BioHit Proline or Eppendorf, 50–1200 μL. Calibrated micropipettors for 5 to 1000 μL deliveries; Gilson Pipetman or VWR. Pipet tips; Rainin GPS-250S and Rainin GPS-1000S or VWR. Disposable reagent reservoirs for multi-channelpipetting; Costar Catalog Number 4870, non-PVC material composition, such as LabCor 730-004. Microtiter flat bottom plate; Immulon 2, Dynex Catalog Number 011-010-3855, or Nunc VWR catalog number 269620. Microplate sealers, Dynex catalog number 5701, or microplate covers, Dynex catalog number 24712-163. Orbital shaker; IKA Schuttler MTS 4, or gyrotory shaker Model g2, New Brunswick Scientific. Microplate reader; Molecular Devices SPECTRAmax 190 or SpectraMax340 or Vmax or ThermoMax. Analytical balance. pH meter.

Chemicals/Reagents

Tris-HCl, Electrophoresis Grade, Fisher catalog number BP153-1. Tris Base USP Grade, Ameresco catalog number T12007. Sodium Chloride, Certified ACS. BovineSerum Albumin (BSA), Fraction V, Protease Free; Golden West Biologicals, Inc., catalog number BA1060. Purified water, Millipore SuperQ or equivalent. Porcine Pancreatic Elastase, Boehringer Mannheim, catalog number 100 907, 3–5 Units/mg. DMSO, Sigma catalog number D8779. N-Suc-Ala-Ala-Val-Ala-pNA, Bachem catalog number L-1410. rAAT standard was provided by the inventors.

Procedure

AAT Activity Buffer, 50 mM Tris-Cl, 0.5 M NaCl, pH 8.0, 0.01% BSA: was prepared by dissolving 6.35 g Tris-HCl and 1.18 g Tris-base in 800 mL purified water. pH was adjusted to 8.0±0.05 with 0.05 M Tris-HCl or 0.05 M Tris-base. 29.22 g NaCl was added, and 0.1 g BSA, and mixed until dissolved. Purified water was added to 1 liter. The solution was filtered through a 0.2 micron pore sized filter. This solution may be stored at 2–8° C. for up to 2 months. PPE Buffer, 0.1 M Tris-Cl, pH 8.0: Was prepared by dissolving 1.37 g Tris-HCl and 0.236 g Tris-base in 80 mL purified water. The pH was adjusted to 8.0±0.05 with 0.1 M Tris-HCl or 0.1 M Tris-base. Purified water was added to 100 mL. The solution was filtered through a 0.2 micron pore sized filter. This solution may be stored at room temperature for up to 2 months. PPE Stock, 1 mg/mL: Was prepared by dissolving 25 mg Porcine Pancreatic Elastase (PPE) in 25 mL PPE Buffer. This solution may be stored at −60 to −80° C. up to six months. Do not freeze-thaw more than once. Substrate, 20 mM N-Suc-Ala-Ala-Val-Ala-pNA in DMSO: Was prepared by dissolving N-Suc-Ala-Ala-Val-Ala-pNA in DMSO, 25 mg in 2.27 mL DMSO or 100 mg in 9.08 mL DMSO. May be stored at room temperature up to two months.

Activity Assay

Prepare PPE Cocktail: Was prepared by mixing 6 µL 1 mg/mL PPE with 12 mL AAT Activity Buffer or amount needed according to the number of plates to be run. One 96-well microtiter plate requires 12 mL PPE Cocktail.

Prepare Test Samples: Samples to be tested were serially diluted with AAT Activity Buffer. 100 µL of each sample was added per well in triplicate. The dilutions were targeted to achieve 30–70% inhibition of the elastase activity. Results outside of this range were repeated. 100 µl/well of PPE cocktail was added. 100 µL/well of assay standard/control, test sample or blank (AAT activity buffer) was added, and shaken at 250–300 rpm on an orbital shaker for 30–60 seconds to mix. Plate was covered and incubated for 15 (±1) minutes at ambient temperature. 10 µL substrate was added to each well except substrate blanks, and shaken at 250–300 rpm on an orbital shaker for 30–60 seconds to mix. Plate was covered and incubated the plate for 60 (±5) minutes at 30±2° C. The cover was removed and Optical density of each well was determined within 10 minutes using a microtiter plate reader set to 400–410 nm. The data was printed and saved as text file.

Calculations

PPE enzyme activity (from manufacturer's certificate of analysis, determined using N-succinyl-L-alanyl-L-analyl-L-analine-4-nitroanilide as substrate) and test sample protein concentration are required inputs. The corrected OD for each replicate control and test sample was calculated by subtracting the average substrate blank OD. Activity for each replicate control and test sample was calculated. Inhibition was determined as follows:

Inhibition=1−(Sample OD Average uninhibited OD)

The Units PPE present in the reaction was determined:

PPE Units in reaction=elastase specific activity in Units/mg (from manufacturer's Certificate of Analysis)×Stock Concentration in mg/mL×volume stock added in mL.

For inhibition≧0.3 and ≦0.7 activity was determined in Units/mL: Activity (Units/mL)=dilution factor×Inhibition×Units PPE Present÷Total Assay Volume (mL)

Specific Activity was determined (Units/mg):

Specific Activity=(Units/mL)÷(mg/mL)

The mean specific activity was calculated, standard deviation and CV for each sample set. The mean was determined from all data in the 30–70% inhibition range.

Example 7

Porcine Pancreatic Elastase Inhibition by TAPI-1 Fusion Protein

The porcine pancreatic elastase inhibitory activity of the fusion protein, TAPI-1, which was refolded from insoluble pellet material produced by yeast, was assayed. The protocol of Example 6 was used, with the following modifications: a 5 ug/ml PPE solution was used and the elastase synthetic substrate N-Suc-Ala-Ala-Ala-pNA (6 mM), both of which were solubilized in the following assay buffer: 50 mM Tris-HCl, 500 mM Na Cl, pH 8.0, 0.01% BSA.

Conditions were as follows: 50 ul of sample or assay buffer for blank and control. 25 uL of PPE solution to samples and control or assay buffer for blank. Plates were incubated for one half hour at 30° C., then 100 uL of substrate was added. Samples were read immediately in microplate reader at 405 nm and 30° C. Inhibition was calculated as a percent of the color development in the control over a 3–5 min. time course, using the following equation:

[(Abs405control−Abs405sample)÷Abs405control× 100%]

Three independent trials were run, with samples taken at different stages of the purification process, with the results shown in Table 32.

TABLE 32

Inhibition of pancreatic porcine elastase by TAPI-1 at various stages of purification

| Sample | Conc. (mg/ml) | % inhibition |
|---|---|---|
| 1 | 0.5 | 97.5 |
| 2 | 10.0 | 96 |
| 3 | 4.0 | 98 |

These results indicate that despite alteration from its native state due to fusion protein construction, the TAPI fusion protein retains a high degree of elastase inhibitory activity.

Example 8

Assay for AAT Activity Using Human Neutrophil Elastase

Materials and Equipment
1. Human Neutrophil Elastase (HNE), Lot #EH2000-2a from Athens Research & Technology: provided as a salt-free lyophilized powder containing 100 μg protein; reconstituted with 200 μL 50 mM Na Acetate, pH5.5, with 150 mM NaCl; divided into 20 μL aliquots (16.9 μM) and stored in −20° C.
2. Suc-Ala-Ala-Pro-Val-pNA (a chromogenic substrate for HNE), from Bachem: provided as a lyophilized powder containing 50 mg peptide; reconstituted with 10 mL DMSO (8.67 mM); Divided into 500 μL aliquots and stored in −20° C.
3. Activity assay buffer: 0.1 M Tris-HCl, 0.5 M NaCl, pH 7.5, stored at room temperature
4. 96 wells Microtiter plates, Catalog No. 3474 from Costar—Ultra Low Cluster
5. Multi-channelpipettor from VWRbrand, 5–50 μL or equivalent
6. Multi-channelpipettor from VWRbrand, 50–300 μL or equivalent
7. Microtiter Plate Reader Versa$_{max}$ from Molecular Devices Methods
1. The internal temperature of the Microtiter Plate Reader was set to 30° C. and allowed to equilibrate at this temperature. Wavelength of the Reader was set at 405 nm.
2. All testing was performed in triplicate. The three results were averaged.
3. The HNE Standard Curve was constructed in the range of 2.5 nM to 20 nM reaction concentration.
4. The HNE sample was diluted in activity assay buffer to 80 nM, 40 nM, 20 nM, 10 nM (HNE Standards).
5. Substrate Solution was prepared by diluting 8.67 mM original stock to 2 mM in the activity assay buffer.

The reagents were added per well in the following sequence:

Activity assay buffer—For the plate blank, 200 μL per well of the activity assay buffer was added. For the substrate blank, 100 μL per well of the activity assay buffer was added. For the HNE Standard Curve, 50 μL per well of the activity assay buffer was added. For the HNE Unknowns, 100 μL per well of the activity assay buffer was added.

Human Neutrophil Elastase—For the HNE Standard Curve, 50 μL per well of the appropriate HNE Standard was added in descending order of the enzyme concentration, beginning with the 80 nM HNE Standard in the first row. For the HNE Unknowns, 100 μL per well of the unknown concentration sample was added in the first row only. Serial-dilution was performed by mixing the sample with the activity assay buffer and then transferring 100 μL per well of the mixture to the next row. Additional serial dilutions were performed until the unknown concentration sample exhibited activity within the defined range (1 nM–20 nM HNE)

The plate was incubated for a minimum of 15 minutes at 30° C. 100 μL per well of the 1 mM Substrate Solution was added to all wells except the plate blank. The plate was sealed and vortexed it at a setting of 5 for 1 minute. The plate was placed in the Microtiter Plate Reader, and allowed to come to 30° C. over 5 minutes. The plate was read in a kinetic mode, 1 reading per minute, for 15 minutes. The concentration of the unknown HNE sample was determined by plotting its rate of activity on the standard curve.

Figure 5:
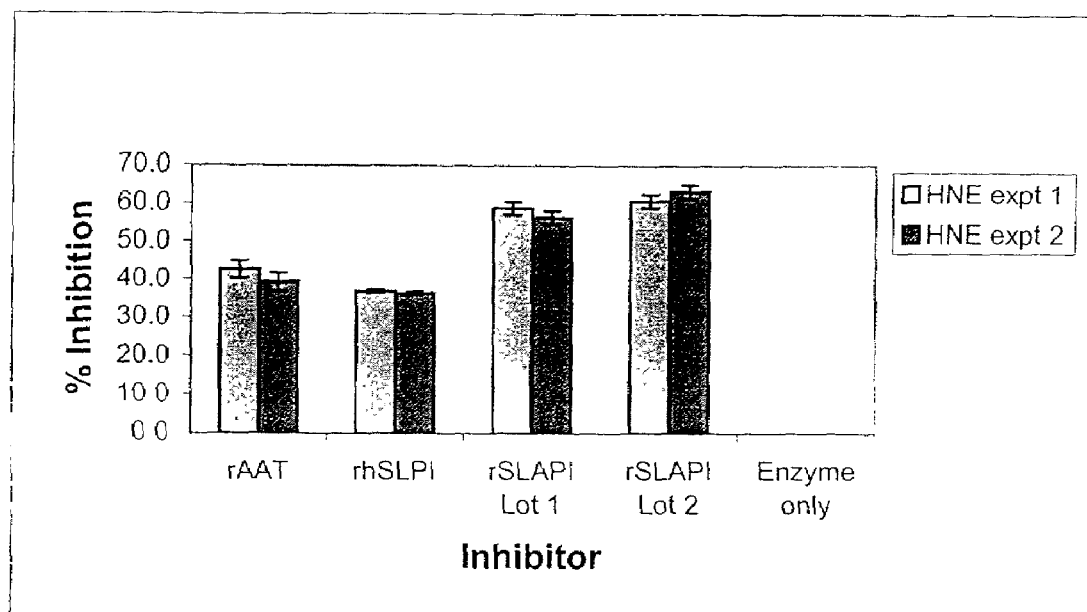
FIG. 5 shows the inhibition of human neutrophil elastase (HNE) by recombinant AAT, recombinant SLPI, and SLAPI.

The inhibitory activity of SLAPI on two different HNE preparations was assessed by the above protocol. Human neutrophil elastase, 20 nM; recombinant AAT, 10 nM; recombinant human SLPI, 10 nM; SLAPI, 10 nM; Suc-Ala-Ala-Pro-Val-pNA, 1 mM. The reagents were incubated for 15 min at 30° C. prior to adding the substrate. The results are shown in FIG. 5, in which the inhibitory activity of 10 nM recombinant AAT (rAAT), 10 nM recombinant human SLPI (rhSLPI), and a batch of SLAPI at 10 nM, run two different times (new SLAPI and old SLAPI) are compared. These results indicate that SLAPI has enhanced protease inhibitory activity on a molar basis compared to either AAP or SLPI alone.

Example 9

Tryptase Activity/Inhibition Assay by RP-HPLC and Measurement of SLAPI Activity Materials and Equipment: *Human Lung Tryptase*, Lot #996290 from Cortex Biochem: provided as a 540 μg/mL (17.4 μM) liquid in 10 mM MES, 300 mM NaCl, 0.02 mM Heparin, pH 6.1, with 0.02% Sodium Azide as a preservative; divided it into 20 μL aliquots and stored in −20° C.; Vasoactive Intestinal Peptide, Lot #Z0203, Product #H-3775 from Bachem: provided as a lyophilized powder containing 1 mg peptide; reconstituted it with 2.5 mL Assay Buffer (400 μg/mL or 120 μM); divided it into 100 μL aliquots and stored in −20° C.; Recombinant human Secretory Leukocyte Protease Inhibitor (rhSLPI), catalog #260-PI from R&D Systems: provided as a lyophilized powder containing 100 μg protein; reconstituted in 100 mM Tris-HCl, 10 mM CaCl$_2$, 0.1% HSA, pH 7.5; stored as 30 μL, 8.55 μM aliquots in −80° C.; Assay buffer: 0.1M Tris-HCl, 1.0 μg/mL heparin, 0.02% Triton X100, pH8.0; stored at room temperature; Trifluoroacetic acid; Acetonitrile, HPLC grade; Water, HPLC grade; Methanol, HPLC grade, 100%; Equivalent substitutions for the following may be used: Waters Model 2690 Separations Module, Waters Model 996 Photo Diode Array Detector, Vydac 238MS54 C-18 Reversed Phase Column, 0.45×25 cm, 300 Å, 5 μm, Vydac, Vydac 238GK54MS Guard Column/Cartridge System, 4.6 mm diameter, 5 μm, Vydac, Upchurch Model A-315 Pre-column Filter, Upchurch Model A-103X Pre-column Filter Frit, Waters Screw neck vial, 12×32 mm, Part No. 186000307, Waters 30011 μL Mandrel Point Insert with Poly String, Part No. WAT094170

Methods: Mobile phases were prepared as follows: Mobile Phase A: 0.1% TFA in water. 1 mLTFA was added to 999 mL HPLC grade water. Mobile Phase B: 0.1% TFA in acetonitrile. 1 mL TFA was added to 999 mL acetonitrile. Mobile Phase C: 100% methanol. Pre-column filter, guard column, and analytical column were attached. The column heater was set at 45° C. The wavelength of the W detector was set at 215 nm. The maximum pressure limit was set to 2000 psi and the minimum pressure limit to 200 psi. The flow rate was set to 1 mL/min throughout the run. The run was initiated with 85% Mobile Phase A and 15% Mobile Phase B. The gradient was held for a linear ramp from 15% Mobile Phase B at t=0 minute to 42% Mobile Phase B at t=10 minutes. The gradient was held at 42% Mobile Phase B for 15 minutes. The column was washed with 100% Mobile Phase C at t=30 minutes. The gradient was held for a linear ramp from 100% Mobile Phase C at t=30 minutes to 85% Mobile Phase A and 15% Mobile Phase B. The column was re-equilibrated for 5 minute at 15% Mobile Phase B.

VIP stock was diluted to the following concentrations in assay buffer: 32 µM, 16 µM, 8 µM, 4 µM, 2 µM (105.6 µg/mL, 52.8 µg/mL, 26.4 µg/mL, 13.2 µg/mL, 6.6 µg/mL, respectively). These were the assay standards. All of the standards were run at a 50 µL injection volume per sample run. If the linearity of the resulting curve ($R^2$ value) is ≧0.970 and the purity of the VIP standards was >90%, proceeded to Sample Preparation.

Tryptase was diluted to 3 nM in assay buffer. If Tryptase concentration was unknown, A280 analysis was performed to get the absorbance of the unknown solution. VIP was diluted to 39 µM in assay buffer. SLPI was diluted to 3 µM in assay buffer. The ideal molar ratio of Tryptase and rhSLPI reaction is 1 to 1000.

The reactions were run in the following manner: 1) Tryptase Activity: Negative Control (VIP only reaction): 30 µL VIP and 60 µL assay buffer were mixed. All 90 µL of the mixture was transferred into a point insert/screw neck vial apparatus. A 50 µL (injection volume) of the control was assayed. Tryptase Samples: 30 µL of 3 nM Tryptase, 30 µL of 39 µM VIP, and 30 µL assay buffer were mixed in a microcentrifuge tube; the tube was incubated for 1 hour at 37° C.; the reaction was terminated with 3% TFA. All 90 µL of the mixture was transferred into a point insert/screw neck vial apparatus. A 50 µL (injection volume) of the control was assayed.

2) Tryptase-SLPI Inhibition: Negative Control (VIP only reaction): 30 µL VIP and 60 µL assay buffer were mixed. All 90 µL of the solution was transferred into a point insert/screw neck vial apparatus. A 50 µL (injection volume) of the control was assayed. Positive Control (Tryptase-VIP only reaction): 30 µL of 3 nM Tryptase, 30 µL of 39 µL VIP, and 30 µL assay buffer were mixed in microcentrifuge tube; the tube was incubated for 1 hour at 37° C.; the reaction was terminated with 3% TFA. All 90 µL of the solution was transferred into a point insert/screw neck vial apparatus. A 50 µL (injection volume) of the control was assayed. Inhibition Reaction Samples: 30 µL of 3 nM Tryptase and 30 µL of 3 µM rhSLPI were mixed in a microcentrifuge tube; the tube was incubated for 30 minutes at 37° C.; 30 µL of 39 µM VIP was added to the solution; the tube was incubated for another 1 hour at 37° C.; the reaction was terminated with 3% TFA. All 90 µL of the mixture was transferred into a point insert/screw neck vial apparatus. A 50 µL (injection volume) of each sample was assayed.

3) Calculations: All of the measurements were based on the peak size of the residual full-length VIP against the calibration curve.

The Tryptase activity was calculated in % activity:
100×[(Residual "full-length" VIP in µg/mL from the Negative Control run—Residual "full-length" VIP in µg/mL from the Tryptase Sample run)÷Residual "full-length" VIP in µg/mL from the Negative Control run)]

The potency of SLPI or other Tryptase Inhibitors was calculated in % Inhibition:
100×[(Residual "full-length" VIP in µg/mL from the Inhibition Reaction Samples—Residual "full-length" VIP in µg/mL from the Positive Control run)÷(Residual "full-length" VIP in µg/mL from the Negative Control run—Residual "full-length" VIP in µg/mL from the Positive Control run)]

4) Example Calculations:
Data:
Residual "full-length" VIP from the Negative Control run 46.05 µg/mL Residual "full-length" VIP from the Tryptase Sample run (aka. Positive Control)=4.85 g/mL
Residual "full-length" VIP from the Inhibition Reaction Samples=19.96 µg/mL
Calculations:
Tryptase activity in % activity:
100×[(46.05 µg/mL−4.85 µg/mL)÷46.05 µg/mL]=89.5% active Tryptase
Potency of SLPI or other Tryptase Inhibitors in % Inhibition:
100×[(19.96 µg/mL−4.85 µg/mL)÷(46.05 µg/mL−4.85 µg/mL)]=36.7% Inhibition The tryptase inhibitory activity of SLAPI, SLPI, and AAT were assayed by the protocol above. Concentrations in these assays: tryptase, 1 nM; vasoactive intestinal peptide, 15 uM; Assay buffer, 0.1M Tris-Cl (pH 8.0), 1.5 ug/mL heparin, 0.02% Triton X-100; AAT, SLPI, or SLAPI was present at concentrations of 0. 500, 1000, 1500, 2000, 2500, 3000, 3500, 4000, and 4500 nM.

Figure 6:
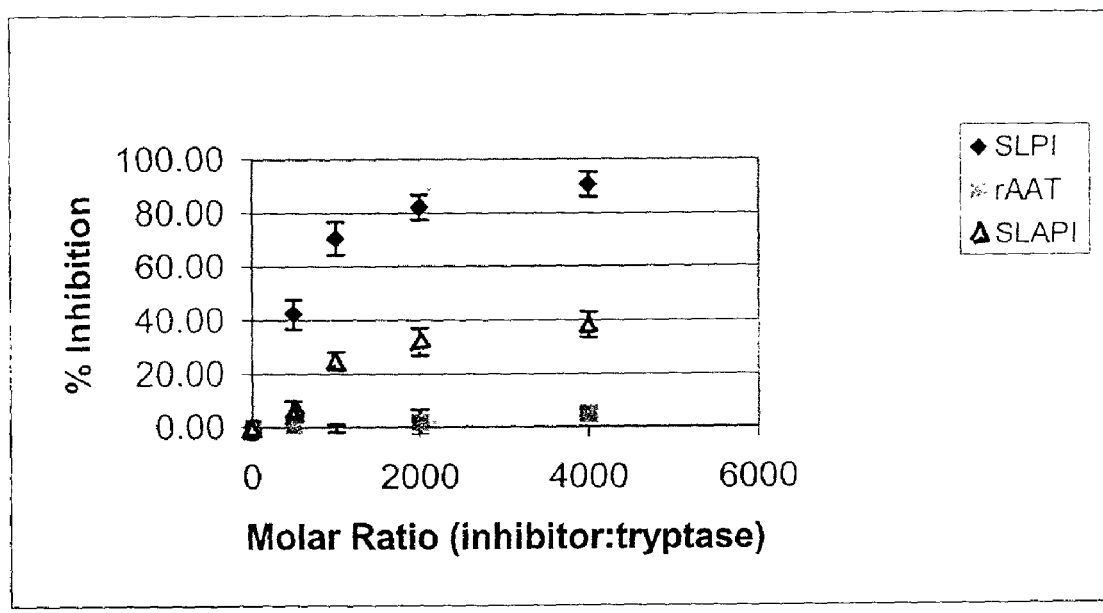
FIG. 6 shows tryptase inhibition by SLPI, SLAPI, and AAT at various molar ratios.

Results are shown in FIG. 6, in which the inhibition of tryptase by various concentrations of SLPI, AAT (recombinant AAT, rAAT) and SLAPI are compared. AAT had no tryptase-inhibiting activity, and the tryptase-inhibiting activity of SLAPI was between the tryptase-inhibiting activities of SLPI and AAT. These results indicate that despite alteration from its native state due to fusion protein construction, the SLAPI fusion protein retains a high degree of tryptase inhibitory activity. In addition, these results, combined with the results for SLAPI inhibition of porcine and human neutrophil elastase in the previous Examples, illustrate the bifunctionality of SLAPI in protease inhibition, in that it inhibits both tryptase and elastase.

Example 10

Impact of TAPI on the Pathogenesis of COPD

A/J mice are exposed to long-term cigarette smoke in the absence and presence of Ilomastat (an MMP inhibitor) or TAPI by inhalation device (Aerogen). Adult mice (12 weeks of age) are exposed to two cigarettes per day, 6 days/wk for 1 week, 3 or 6 mths.

A pilot experiment is run to determine if, after a one week exposure to aerosolized Ilomastat on a daily basis, there are detectable matrix metalloprotease (MMP) neutralizing levels of Ilomastat in the broncho-alveolar lavage (BAL) of mice. This study consists of two groups of five animals each. One group is administered nebulized PBS only (control) for 30 minutes and then smoke, the other group gets nebulized Ilomastat (in PBS) and then smoke. After one week BAL samples are taken from the mice and assessed by HPLC and MMP-9 inhibition for the presence of Ilomastat. The samples are also assayed for MMP activity using a synthetic substrate. The results from this study help refine the dose level given to the mice in the main study to ensure that the mid-high doses are at least neutralizing.

Main Study

| Group # | | Exposure time course | | |
| --- | --- | --- | --- | --- |
| | | 1 wk | 3 mths | 6 mth |
| 1 | NS (14) | 10 | 10 | 12 |
| 2 | Sm (wt, A/J, Vehicle) | 10 | 10 | 12 |
| 3 | Sm (Ilomastat dose 1) | 10 | 10 | 12 |

-continued

Exposure time course

| Group # | | 1 wk | 3 mths | 6 mth |
|---|---|---|---|---|
| 4 | Sm (Ilomastat dose 2) | 10 | 10 | 12 |
| 5 | Sm (Ilomastat dose 3) | 10 | 10 | 12 |
| | (160 mice total) | | | |
| 6 | Sm (TAPI dose 1) | 10 | 10 | 12 |
| 7 | Sm (TAPI dose 2) | 10 | 10 | 12 |
| 8 | Sm (TAPI dose 3) | 10 | 10 | 12 |
| | (96 mice total) | | | |
| | Total # of mice used in study = 256 | | | |

Two groups with highest doses of Ilomastat and TAPI beginning 3 mths after initiation of smoking are included.

Analysis

The right lung is used for fixation/inflation and paraffin embedding for morphometry—Lm (mean distance between alveolar walls, a measure of lung elasticity), $SA/V_o$ (surface area/volume); and Inflammatory cell influx: Macrophage, T cell influx are assessed by immunohistochemistry, and neutrophils by morphology The Left lung is used for BAL—for drug, MMP inhibition; and for Tissue MMP activity.

Example 11

Matrix Metalloprotease-9 (MMP-9) Assay

Materials and Equipment
1. Active MMP-9 Enzyme. Catalog #PF024-5UG from Oncogene Research Products. Provided as a 5 μg/50 μL stock; dilute to 500 μl by adding 450 μl of 50 mM HEPES, pH 7.0, 10 mM $CaCl_2$ (final concentration 10 ng/μl). Divide into 100 μl aliquots, store at −80° C.
2. Peptide Substrate. Catalog #H7145 from Bachem. Dissolve 25 mg in 1 ml of DMF (final concentration 38 mM). Store at −20° C. in glass vial.
3. Stock Reagents:
   0.5M HEPES, pH 7.0 in $ddH_2O$ (10×stock)
   0.1M $CaCl_2$ in $ddH_2O$ (10×stock)
   0.1M Ellman's Reagent in EtOH (100×stock) Store at 4° C.
4. 96-well Microtiter plates. Catalog #3474 from Costar—Ultra Low Cluster.
5. Microtiter Plate Reader. Versa$_{max}$ from Molecular Devices Inc.

Methods
1. Set internal temperature of Microtiter Plate Reader to 25° C.
2. Make up fresh Reagent Mix. For one 96-well plate make up 15 ml: 2 ml HEPES stock (50 mM final), 2 ml $CaCl_2$ stock (10 mM final), 0.5 ml Ellmans Reagent stock (2.5 mM final), 0.5 ml of substrate stock (0.85 mM final), 10 ml $ddH_2O$
3. Add 150 μl/well of reagent mix.
4. Add 50 μl/well of sample. Serially diluted samples should be diluted with 50 mM HEPES, pH 7.0, 10 mM $CaCl_2$ (dilution buffer, DB). Initially measure a 1×(undiluted) sample before proceeding with serial dilutions. The range of serial dilutions is adjusted based on activity of the 1×samples.
5. $Abs_{410}$ is read every 10–15 min for 3 hrs.

Controls
no MMP-9 blank=50 μl of DB.
+MMP-9 control=5 μl (50 ng or 0.54 pmols) of MMP-9 stock+45 μl DB. This should yield 1.0 AU in 2–3 hrs.

The assay is run at 25° C. to optimize enzyme stability. pH should be ≦7.0 to minimize non-enzymatic color development.

Example 12

Matrix Metalloprotease-9 (MMP-9) and Elastase Inhibitory Assay of N-TAPI

Protein from the insoluble fraction of N-TAPI (prepared as described in Example 2)-containing yeast cell lystaes was refolded by the method of Huang et al. FEBS Letters (1996), 384; 155–161. The method was followed exactly with the exception that dialysis to remove urea was substituted by slow dilution followed by diafiltration, 2-mercaptoethanol was substituted by glutathione, and the final purification column consisted of an anion- (Q-Sepharose) rather than a cation-exchange (CM-cellulose) resin.

The refolded N-TAPI-2 as well as three column fractions from the final purification column were subjected to the MMP-9 inhibitory assay described in Example 11. All four fractions contained 1–2 mg/ml of total protein, and 10 μL of sample (10–20 μg) was added to an assay mix containing 25 ng (0.29 pmols) of MMP-9. The four N-TAPI-2 samples yielded 93–98% inhibition of MMP-9 activity as determined by absorbance at 410 nm over a five hour period.

Elastase activity was also measured for this N-TAPI. The assay method was that of Example 6. The refolded material as well as two of the three column fractions displayed 98% or greater inhibition using the modified PPE assay.

These results demonstrate that the fusion protein N-TAPI retains both the MMP-inhibiting activity of TIMP-1 and the elastase-inhibiting activity of SLPI. Thus, this construct is truly bifunctional.

We claim:

1. A fusion protein comprising a functionally active portion of alpha 1-antitrypsin and a functionally active portion of secretory leukocyte protease inhibitor, wherein said fusion protein has alpha 1-antitrypsin protease inhibitor activity and secretory leukocyte protease inhibitor activity.

2. A fusion protein comprising
   a) amino acids from about 1 to about 394 of SEQ ID NO: 2; and
   b) amino acids from about 1 to about 107 of SEQ ID NO: 4, wherein said fusion protein has alpha 1-antitrypsin protease inhibitor activity and secretory leukocyte protease inhibitor activity.

3. A pharmaceutical composition comprising the fusion protein of claim 1, admixed with a pharmaceutically acceptable vehicle.

4. The fusion protein of claim 2 wherein the carboxy terminus of amino acids from about 1 to about 394 of SEQ ID NO: 2 is linked to the amino terminus of amino acids from about 1 to about 107 of SEQ ID NO: 4.

5. The fusion protein of claim 2 wherein the carboxy terminus of amino acids from about 1 to about 107 of SEQ ID NO: 4 is linked to the amino terminus of amino acids from about 1 to about 394 of SEQ ID NO: 2.

6. A method for inhibiting protease activity, comprising contacting the protease with the fusion protein of claims 1 or 2.

7. The method of claim 6 wherein the protease activity is associated with a disorder selected from the group consisting of emphysema, asthma, chronic obstructive pulmonary disease, cystic fibrosis, otitis media, and otitis externa.

8. The method of claim 6, wherein the protease activity is associated with HIV infection.

9. The method of claim 6, wherein the fusion protein is contacted with the protease by administering the fusion protein to an individual having the protease.

10. A method of treating an individual suffering from, or at risk for, a disease or disorder involving unwanted protease activity comprising administering to the individual an effective amount of the fusion protein of claims 1 or 2.

11. The method of claim 10, wherein the individual suffers from emphysema.

12. The method of claim 10, wherein the individual suffers from asthma.

13. The method of claim 10, wherein the individual suffers from chronic obstructive pulmonary disease.

14. The method of claim 10, wherein the individual suffers from cystic fibrosis.

15. The method of claim 10, wherein the individual suffers from otitis media or otitis externa.

16. The fusion protein of claim 2, comprising SEQ ID NO: 8.

17. The fusion protein of claim 2, comprising SEQ ID NO: 16.

18. A method for inhibiting protease activity, comprising contacting the protease with the fusion protein of claims 16 or 17.

19. The method of claim 18 wherein the protease activity is associated with a disorder selected from the group consisting of emphysema, asthma, chronic obstructive pulmonary disease, cystic fibrosis, otitis media, and otitis externa.

20. A method for inhibiting protease activity, comprising contacting the protease with the fusion protein of claim 1.

21. A method for inhibiting protease activity, comprising contacting the protease with the fusion protein of claim 2.

22. The fusion protein of claim 1, wherein said functionally active portion of alpha 1-antitrypsin an has elastase inhibitory activity and said functionally active portion of secretory leukocyte protease inhibitor has elastase inhibitory activity.

23. The fusion protein of claim 22 further comprising tryptase inhibitory activity.

24. The fusion protein of claim 1 or claim 22, wherein the specific activity of the elastase inhibitory activity of said fusion protein is double the specific activity of the elastase inhibitory activity of AAT.

25. A pharmaceutical composition comprising the fusion protein of claim 2 admixed with a pharmaceutically acceptable vehicle.

26. A pharmaceutical composition comprising the fusion protein of claim 22 admixed with a pharmaceutically acceptable vehicle.

* * * * *